(12) United States Patent
Grijpma et al.

(10) Patent No.: US 8,829,069 B2
(45) Date of Patent: Sep. 9, 2014

(54) METHOD FOR PREPARING A DEGRADABLE POLYMER NETWORK

(75) Inventors: Dirk Wybe Grijpma, Hengelo (NL); Jan Feijen, Hengelo (NL); Erhan Bat, Enschede (NL)

(73) Assignee: Medisse B.V., Ede (NL)

( * ) Notice: Subject to any disclaimer, the term of this patent is extended or adjusted under 35 U.S.C. 154(b) by 0 days.

(21) Appl. No.: 13/700,073

(22) PCT Filed: May 26, 2010

(86) PCT No.: PCT/EP2010/057269
§ 371 (c)(1),
(2), (4) Date: Jan. 22, 2013

(87) PCT Pub. No.: WO2011/147452
PCT Pub. Date: Dec. 1, 2011

(65) Prior Publication Data
US 2013/0123384 A1    May 16, 2013

(51) Int. Cl.
*C08J 3/28* (2006.01)
*C08F 2/46* (2006.01)
*C08G 61/04* (2006.01)

(52) U.S. Cl.
USPC ............ 522/163; 522/162; 522/1; 520/1

(58) Field of Classification Search
USPC ................. 522/163, 162, 1; 520/1
See application file for complete search history.

(56) References Cited

U.S. PATENT DOCUMENTS 5,410,016 A    4/1995    Hubbell et al.
6,207,767 B1    3/2001    Bennett et al.

FOREIGN PATENT DOCUMENTS

| EP | 1142596 | | 10/2001 |
|---|---|---|---|
| EP | WO 2004/041318 | * | 5/2004 |
| EP | WO 2005/002596 | * | 1/2005 |
| EP | 2 075 279 | * | 12/2007 |
| EP | 2075279 | | 7/2009 |
| WO | 0033764 | | 6/2000 |
| WO | 2004041318 | | 5/2004 |
| WO | 2005002596 | | 1/2005 |

OTHER PUBLICATIONS

Bat, Erhan, Theo G. Van Kooten, Jan Feijen, Dirk W. Grijpma, "Macrophage-mediated erosion of gamma irradiated poly(trimethylene carbonate) films", Apr. 8, 2009, Biomaterials 30, 3652-3661.*
Bat et al., "Macrophage-mediated erosion of gamma irradiated poly(trimethylene carbonate) films," Biomaterials, vol. 30, No. 22, pp. 3652-3661 (2009).

* cited by examiner

*Primary Examiner* — Ling Choi
*Assistant Examiner* — Jessica E Whiteley
(74) *Attorney, Agent, or Firm* — Edward J. Baba; Bozicevic, Field & Francis LLP

(57) ABSTRACT

The present invention relates to methods for preparing a degradable polymer network. The methods for preparing a degradable polymer network comprise a) preparing a polymer composition comprising monomers of cyclic carbonates and/or cyclic esters and/or linear carbonates and/or linear esters and/or cyclic ethers and/or linear hydroxycarboxylic acids at a temperature between 20° C. and 200° C.; b) adding a cross-linking reagent comprising at least one double or triple C—C bond and/or a cross-linking radical initiator; c) processing the polymer composition (that contains the crosslinking reagent into a desired shape; d) Crosslinking by irradiating the mixture. Further, the present invention relates to a degradable polymer network. Furthermore, the present invention relates to the use of the degradable polymer network.

20 Claims, 29 Drawing Sheets

(A)

(B)

(A)

(B)

(A)

(B)

(A)

(B)

(A)

(B)

(A)

(B)

(C)

(D)

(A)

(B)

(A)

(B)

METHOD FOR PREPARING A DEGRADABLE POLYMER NETWORK

Figure 1:
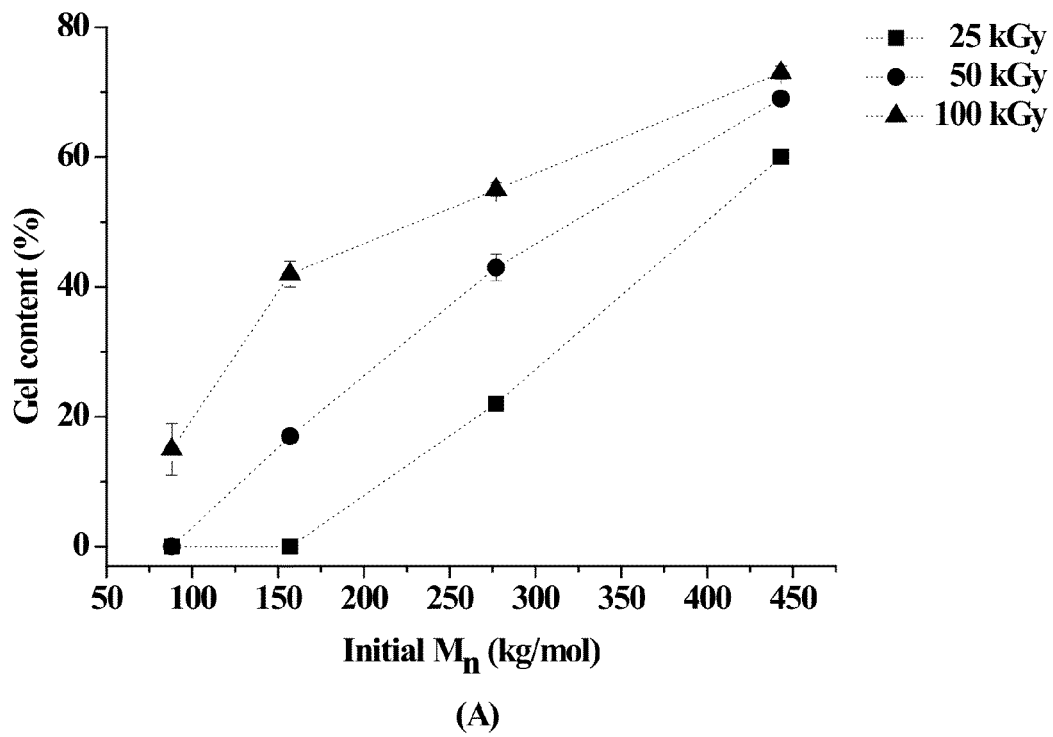
Figure 1:
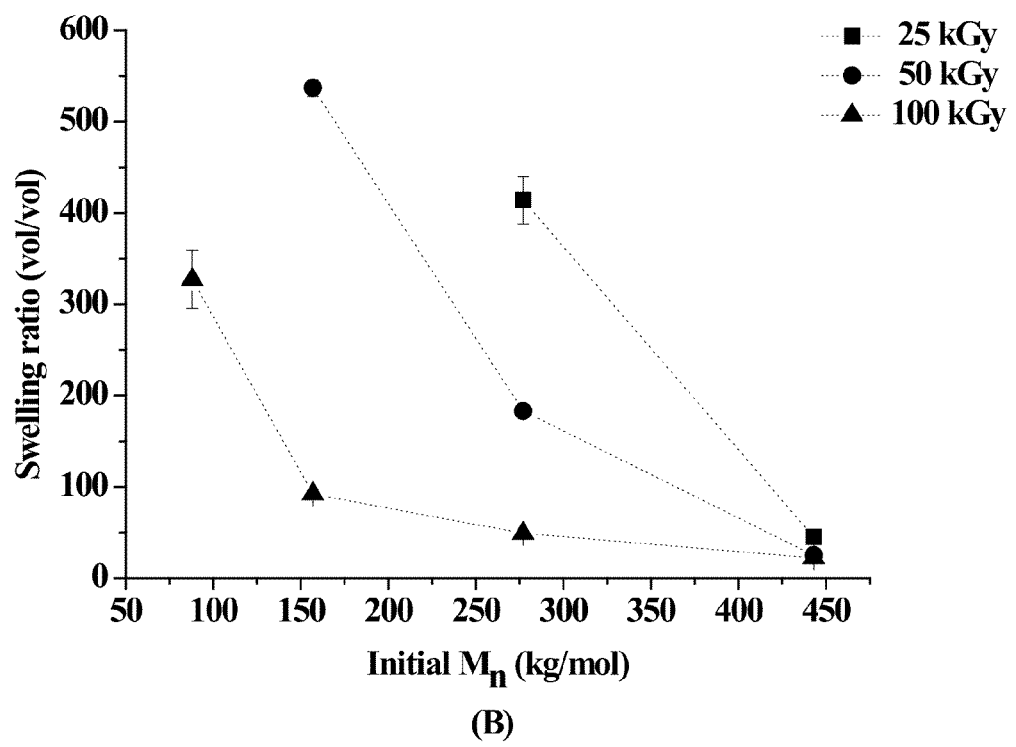

The present invention relates to methods for preparing a degradable polymer network. Further, the present invention relates to a degradable polymer network. Furthermore, the present invention relates to the use of the degradable polymer network.

Developments in the multidisciplinary field of tissue engineering have yielded a novel set of tissue replacement parts and implementation strategies. Scientific advances in biomaterials, stem cells, growth and differentiation factors, and biomimetic environments have created unique opportunities to fabricate tissues in the laboratory from combinations of engineered extracellular matrices ("scaffolds"), cells, and biologically active molecules. Physical, chemical and biological properties of these scaffold materials are therefore very important in tissue engineering. Cell behaviour is influenced by the rigidity of the substrate on which the cells are cultured. In soft tissue engineering, the scaffold should transmit mechanical stimuli to the cells and tissues, and withstand repeated dynamic loadings in vivo. Also in vitro this can be required, as mechanical stimulation of cell-seeded tissue engineering scaffolds during cell culture enhances the development of engineered tissues and their function. In this respect, both flexible and non-flexible, form-stable and resorbable elastomeric or non-elastomeric polymer networks that allow cell adhesion and proliferation are of great interest, including amorphous and semi-crystalline polymer materials. Crosslinked polymer materials that have these properties are the object of the present invention.

Poly(trimethylene carbonate) (PTMC) is a biocompatible and biodegradable polymer which has a glass transition temperature ($T_g$) of approximately −17° C. This amorphous and flexible polymer can be cross-linked by irradiation in an inert atmosphere to form a creep resistant and form-stable network. Such elastomeric polymers are especially used as scaffolding materials for the engineering of soft tissues or as depots for controlled release systems, or in the design of implants, such as anti-adhesion membranes or vascular prostheses. Creep resistance and form-stability are desired properties. In vivo, PTMC degrades relatively rapid by surface erosion without the release of acidic degradation products. To broaden the applicability of this polymer, trimethylene carbonate (TMC) based materials having tuneable low erosion rates need to be developed.

Poly(D,L-lactide) (PDLLA) is a biocompatible and biodegradable polymer used for the preparation of resorbable sutures, controlled drug release systems, and tissue engineering scaffolds. PDLLA is a glassy, non-crystalline aliphatic polyester that degrades by bulk hydrolysis in vivo. Upon irradiation, a reduction in molecular weight of PDLLA is observed. (D,L)-lactide is a monomer that can be used to prepare PDLLA.

Copolymers of TMC and DLLA present intermediate physical properties between those of PTMC and PDLLA: depending on the composition of copolymers, glass transition temperatures, elastic modulus values, tensile strengths and degradation rates can be tuned. This makes these polymers suitable for numerous biomedical applications. However, amorphous non-cross-linked co-polymers with glass transition temperatures below physiological temperatures have poor form stability at body temperature. Therefore, after crosslinking, autoclaving can be used as a method of sterilisation of medical devices prepared from these copolymers.

Polycaprolactone (PCL) is a biodegradable polyester with a low melting point of around 60° C. and a glass transition temperature of about −60° C. This polymer is often used as an additive for resins to improve their processing characteristics and their end use properties (e.g., impact resistance).

Poly(L-lactide) (PLLA) is a biodegradable, thermoplastic, aliphatic polyester derived from renewable resources, such as corn starch or sugarcanes. PLLA is the product resulting from polymerization of L,L-lactide (also known as L-lactide). PLLA has a glass transition temperature between 50-80° C. and a melting temperature between 170-200° C. PLLA is currently used in a number of biomedical applications, such as sutures, stents, dialysis media and drug delivery devices. It is also being evaluated as a material for tissue engineering. PLLA and PDLLA have been used as the hydrophobic block of amphiphilic synthetic block copolymers used to form the vesicle membrane of polymersomes. PLLA and PDLLA are sustainable alternatives to petrochemical-derived products, since the lactides from which they are ultimately produced can be derived from the fermentation of agricultural by-products such as corn starch or other carbohydrate-rich substances like maize, sugar or wheat.

Polyethylene glycol (PEG) is a polyether compound with many applications from industrial manufacturing to medicine. It has also been known as polyethylene oxide (PEO) or polyoxyethylene (POE). PEG, PEO or POE refers to an oligomer or polymer of ethylene oxide. Polyethylene glycol is produced by the interaction of ethylene oxide with water, ethylene glycol or ethylene glycol oligomers. The reaction is catalyzed by acidic or basic catalysts. It is the basis of a number of laxatives (e.g., macrogol-containing products) and of many skin creams.

Sterilization by autoclaving can be done with PTMC, amorphous and semi-crystalline poly(lactide)s, PCL and PEO polymers when they are crosslinked. This is also the case for co-polymers based on their respective monomers.

High energy radiation is known to cause chemical changes in the structure of polymers by the formation of free radicals, ions, or excited states that can allow the cross-linking of polymers. Upon irradiation cross-linking prevails for some polymers, whereas for other polymers chain scission is dominant. For biomedical applications, gamma- and electron beam irradiation have been widely used to modify the surface or bulk properties of polymeric biomaterials and to sterilise them in a cost-effective way.

Gamma irradiation is a widely used cost-effective method for the sterilisation of (polymeric) biomaterials. The high energy gamma rays can initiate free radical- or ionic reactions, which result in changes in the surface- and bulk properties of the materials being sterilised. For some polymers cross-linking is observed during gamma irradiation, whereas for others the irradiation leads to chain scission or unzipping reactions and a decrease in molecular weight. These decreased molecular weights can limit the useful life-time of resorbable polymeric implants like tissue engineering scaffolds, fracture fixation devices or sutures, due to rapid decrease in mechanical strength and disintegration of the device. Also upon implantation of drug releasing matrices prepared from biodegradable polymers, the lowering of the molecular weight can lead to early onset of mass loss and influence drug release characteristics. Gamma irradiation significantly improves the creep resistance and form-stability of PTMC. By increasing the efficiency of cross-linking of PTMC by gamma irradiation, the adverse effects of irradiation on the tensile properties of the networks can be prevented. The higher gel contents and network densities obtained will further improve creep resistance and also slow down degradation and erosion. Degradation is the process of polymer chain scission by the cleavage of bonds in the polymer backbone. This leads to a reduction of length of the polymer chains. Erosion is the mass loss of a polymer matrix which can be due to the loss of monomers, oligomers, polymer chains or parts thereof. Erosion can be the result of biological, chemical or physical effects. Accordingly, it can be understood that polymer degradation is part of the polymer erosion process.

Another type of polymerization and cross-linking is of interest: radical polymerization and cross-linking of macromers prepared from degradable oligomers. Both processes have been used to prepare resorbable polymer networks efficiently at ambient temperature.

There are continuous needs in the prior art to further develop methods for the preparation of biocompatible and degradable polymer networks.

It is a goal of the present invention, amongst others, to provide flexible, biocompatible and degradable polymer networks with amorphous structure and low glass transition temperature, specifically, degradable polymer networks which are form-stable and creep resistant materials with low glass transition temperatures and tuneable degradation properties. The present invention also aims to prepare polymer networks with different flexibilities and different elastic modulus values with increased form stability and allowing the preparation of materials suitable for sterilization by autoclaving or thermal treatment.

According to the present invention, this goal, amongst others, is met by the method for preparing a degradable polymer network comprising: a) preparing a polymer composition comprising monomers of cyclic carbonates and/or cyclic esters and/or linear carbonates and/or linear esters and/or cyclic ethers and/or linear hydroxycarboxylic acids at a temperature between 20° C. and 200° C.; b) adding a cross-linking reagent comprising at least one double or triple C—C bond and/or a cross-linking radical initiator; c) processing the polymer composition (that contains the crosslinking reagent) into a desired shape; d) Crosslinking by irradiating the mixture.

Polymer networks are polymers that have bonds that link one polymer chain to another. They can be covalent bonds or ionic bonds. The term "cross-linked polymers" can also be used for polymer networks. A polymer is a large molecule (also designated as macromolecule) composed of repeating structural units typically connected by covalent chemical bonds. The compounds, from which the polymers are prepared, are designated as monomers.

The monomers are one or more, two or more, three or more cyclic carbonates and/or cyclic esters and/or cyclic ethers and/or linear carbonates and/or linear esters and/or linear hydroxycarboxylic acids.

Carbonates are hydrocarbons with at least one carbonate group —O—C(=O)—O— in the hydrocarbon, such as one carbonate group, two carbonate groups, three carbonate groups.

Esters are hydrocarbons with at least one ester group —COO— in the hydrocarbon, such as one ester group, two ester groups, or three ester groups.

Hydroxycarboxylic acids are hydrocarbons with a carboxylic acids (organic function —COOH) comprising a second organic group, a hydroxy group (—OH).

Cyclic molecules have a ring structure, such as aryl, or aromatic rings. Linear molecules are hydrocarbon chains, such as alkanes.

The polymer composition of the invention may be prepared in step a) by reaction of the monomer or mixture of monomers under inert atmosphere. It can be nitrogen, argon or vacuum. The reaction is carried out under mechanical stirring until homogeneity. Stirring until homogeneity is stirring until forming a uniform mixture to the naked eye. Stirring can be carried out by any other type of stirring or mixing.

The degradable polymer according to the present invention is a resorbable polymer and/or a biodegradable polymer. The polymer network of the present invention can be amorphous, semi-crystalline or crystalline.

A crosslinking reagent can be a crosslinking agent or a crosslinking aid. The reagent is a crosslinking aid when it only helps to the formation a better polymer network (the network is also formed without the reagent). The reagent is a crosslinking agent when the network is only formed when the reagent is present. A better network can be a network with a higher gel content, a more creep resistant network, or a more elastic network.

The crosslinking reagent comprises at least one double or triple C—C bond, such as one or more, two or more, three or more, four or more double or triple C—C bonds.

Double or triple C—C bonds are also designated $sp^2$-$sp^2$ carbon-carbon bond or sp-sp carbon-carbon bond, respectively. A C—C bond is to be understood as carbon-carbon bond.

The crosslinking of the materials of the present invention allows the sterilization of device made of or coated with the degradable polymer networks at elevated temperatures such as by autoclaving or heat treatments.

A radical initiator is a chemical substance that can produce radical species under conditions such as exposure to irradiation, light, temperature variation, or electrochemical reaction. Particular types of radical initiator can be photo-initiators, thermal initiators or redox-initiators. They respectively are a chemical substance that produces radical species upon exposure to light, temperature changes or exposure to electrochemical reactions.

Irradiation is the process by which an item is exposed to radiation. Radiations can typically be ionizing radiation, such as electron beam processing, X-rays or gamma rays, but this term also applies to non-ionizing radiation as light radiation in the visible, ultraviolet or infrared spectral region, or microwaves. If administered at appropriate levels, all of these forms of radiation can be used to sterilize objects, namely it is a technique used in the production of medical instruments and disposables, such as syringes as well as in the disinfection and sterilization of food.

The temperature range in step a) is between 20° C. to 200° C., such as 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C. 120° C., 125° C., 130° C., 135° C., 140° C., 145° C., 150° C., 155° C., 160° C., 165° C., 170° C., 175° C., 180° C., 185° C., 190° C., 195° C., 200° C., preferably from 100° C. to 200° C.

A cross-linking reagent is a chemical compound helping the formation of the polymer network. They create bonds that link one polymer chain to another. They can be covalent bonds. The term "cross-linking" is used when it usually refers to the use of cross-links to promote a difference in the polymers' physical properties.

According to the present invention, the crosslinking reagent is chosen from the group consisting of an acrylate, a methacrylate, a multi-acrylate, multimethacrylate, a fumarate, a multifumarate, a maleate, a multimaleate, a maleic anhydride, an itaconate or multi-itaconate. Acrylates and multiacrylates contain respectively one, and several acrylate units. The acrylate unit comprises one vinyl group and one ester group. It is also designated as propenoate and has the formula $C_3H_3O_2$. Methacrylates ($CH_2$=CMeCOO—) are the salts or esters of methacrylic acid. Methacrylates contain methyl-vinyl groups, that is, two carbon atoms double bonded to each other, directly attached to the carbonyl carbon, and wherein the vinyl group is substituted with a non-terminal methyl group. A multimethacrylate compound contains several methacrylate group. A fumarate has the general formula ($O_2CCH=CHCO_2$) and can be substituted by an alkyl or acyl. A multifumarate contains several fumarate group. A maleate is the cis-isomer of a corresponding fumarate. A multi-maleate contains several maleate groups. Maleic anhydride (also designated as cis-butenedioic anhydride or toxilic anhydride or dihydro-2,5-dioxofuran) is an organic compound with the formula $C_2H_2(CO)_2O$. An itaconate is the ester of itaconic acid. Itaconic acid, or methylenesuccinic acid, is non-toxic, and readily biodegradable. An itaconate is also designated by the name 2-methylidenebutanedioate and comprises two esters (—COO—) and a $sp^2$ (double C—C bond) methyl substitution in position 2. A multi-itaconate contains several itaconate groups.

According to the present invention, the cross-linking reagent is chosen from the group consisting of acrylate-functionalized poly(trimethylenecarbonate)-based oligomer, an methacrylate-functionalized poly(trimethylenecarbonate)-based oligomer, a fumarate-functionalized poly(trimethylenecarbonate)-based oligomer, an acrylate-functionalized poly(D,L-lactide)-based oligomer, methacrylate-functionalized poly(D,L-lactide)-based oligomer, a fumarate-functionalized poly(D,L-lactide)-based oligomer, an acrylate-functionalized poly(L-lactide)-based oligomer, a methacrylate-functionalized poly(L-lactide)-based oligomer, a fumarate-functionalized poly(L-lactide)-based oligomer, an acrylate-functionalized poly(E-caprolactone)-based oligomer, a methacrylate functionalized poly($\epsilon$-caprolactone)-based oligomer, a fumarate-functionalized poly($\epsilon$-caprolactone)-based oligomer, an acrylate-functionalized poly(ethylene glycol)-based oligomer, a methacrylate-functionalized poly(ethylene glycol)-based oligomer, a fumarate-functionalized poly(ethylene glycol)-based oligomer, ethylene diacrylate, ethylene glycoldiacrylate, tetraethylene glycol diacrylate, polyethylene glycol diacrylate, trimethylolpropane triacrylate, trimethylolpropane trimethacrylate, pentaerythritol triacrylate, pentaerythritol tetra-acrylate, ethylene glycoldimethacrylate, tetraethylene glycol dimethacrylate, polyethylene glycol dimethacrylate and derivatives thereof.

Methyl methacrylate (MMA) is methyl 2-methylprop-2-enoate and has the linear formula $C_5H_8O_2$. Ethylene diacrylate has the formula $C_8H_{10}O_4$. Pentaerythritol triacrylate (PETA) is also designated as 2-propenoic acid 2-(hydroxymethyl)-2-[[(1-oxo-2-propenyl)oxy]methyl]-1,3-propanediyl ester and has the linear formula ($H_2C=CHCO_2CH_2$)$_3$ $CCH_2OH$. Irradiating PTMC films that contain pentaerythritol triacrylate as a cross-linking reagent makes the PTMC networks formed in this way not only have very high gel contents, but also excellent elastomeric properties: in tensile tests, the specimens showed low modulus values, and high strength and elongation at break. The permanent deformation upon cyclic loading was very low. In addition, cross-linking in this manner also resulted in reduced enzymatic erosion rates of the networks. Trimethylolpropane triacrylate (TMPTA) has the linear formula ($H_2C=CHCO_2CH_2$)$_3$ $CC_2H_5$. Trimethylolpropane trimethacrylate has the linear formula [$H_2C=C(CH_3)CO_2CH_2$]$_3CC_2H_5$. Pentaerythritol tetra-acrylate has the formula ($H_2C=CHCO_2CH_2$)$_4C$, ethylene glycoldimethacrylate has the formula $C_{10}H_{14}O_4$, also designated by $CH_2=C(CH_3)C(O)OCH_2CH_2OC(O)C(CH_3)=CH_2$ and tetraethylene glycol dimethacrylate has the formula $C_{14}H_{22}O_6$. Polyethylene glycol is a condensation polymers of ethylene oxide and water with the general formula $H(OCH_2CH_2)_nOH$, where n is the average number of repeating oxyethylene groups.

By derivatives thereof is understood the above-mentioned crosslinking reagents substituted by any organic group and/or an alkyl, alkenyl, alkynyl, aryl.

In a most preferred embodiment, step b) comprises 0.01 to 15 wt %, preferably 0.1% wt to 10% wt, more preferably 0.5% wt to 8% wt, most preferably 1% wt to 5% wt of the cross-linking reagent by weight percentage of the total weight of the polymer composition.

According to the methods of the present invention, the monomers in step a) are obtained from cyclic carbonates chosen from the group trimethylene carbonate, ethylene carbonate, diethylene glycol-bis-allyl-carbonate, and derivatives thereof. Trimethylene carbonate is designated as 1,3-Dioxan-2-one and has the formula $C_4H_6O_3$. Ethylene carbonate with the formula $C_3H_4O_3$ is designated as 1,3-dioxolan-2-one. Diethylene glycol-bis-allyl-carbonate has the formula $C_{12}H_{18}O_7$.

According to the methods of the present invention, the monomers in step a) are obtained from cyclic esters chosen from the group L-lactide, D-lactide, D,L-lactide, $\epsilon$-caprolactone, dioxanone, polyethylene glycol, glycolide, and derivatives thereof. L-lactide is the levogire lactide enantiomer, D-lactide is the dextrogire enantionmer and D,L-lactide is the racemic mixture. $\epsilon$-Caprolactone or simply caprolactone is a cyclic ester, a member of the lactone family, with a seven-membered ring with the formula $(CH_2)_5CO_2$. Dioxanone is a dioxane derivative (carbonyl instead of the methylene group) and has the formula $C_4H_6O_3$. Glycolide, 1,4-dioxane-2,5-dione and has the formula $C_4H_4O_4$.

According to the methods of the present invention, the monomers in step a) are obtained from linear carbonates chosen from the group diethyl carbonate or diphenylcarbonate. Diethyl carbonate has the formula $C_5H_{10}O_3$ and diphenylcarbonate $C_{13}H_{10}O_3$.

According to the methods of the present invention, the monomers in step a) are obtained from linear esters chosen from the group fumaric acid monoethyl ester, fumaric acid diethylester, dimethylterephtalate, diethylterephtalate. Fumaric acid monoethyl ester is also designated by dimethyl (E)-butenedioate and has the formula $C_6H_8O_4$. Fumaric acid diethylester is also designated by (E)-2-Butenedioic acid diethyl ester has the formula $C_8H_{12}O_4$. Dimethylterephtalate and diethylterephtalate have respectively the formulas $C_{12}H_{14}O_4$.

According to the methods of the present invention, the monomers in step a) are obtained from linear ethers chosen from the group polyethylene glycol and derivatives thereof. Polyethylene glycol (PEG) is also known as polyethylene oxide (PEO) or polyoxyethylene (POE), refers to an oligomer or polymer of ethylene oxide.

By derivatives thereof is to be understood as substituted monomers at any position, by an alkyl, alkenyl, alkynyl, acyl, cycloalkyl, cycloalkynyl. The substituent may carry an organic group.

Resorbable polymer networks and amorphous oligomers with low glass transition temperatures ($T_gs$), can be based on trimethylene carbonate (TMC), D,L-lactide (DLLA), and $\epsilon$-caprolactone (CL) monomers and poly(glycerol sebacate) and have been developed by several groups and show elastomeric properties. End-functionalization of these relatively low molecular weight polymers with (meth)acrylate- or fumarate groups allows network formation upon UV irradiation in the presence of a photoinitiator, or by thermal or redox initiation of the radical polymerization. The ultimate tensile strengths and elongation at break values of flexible networks obtained in this manner significantly increase with increasing macromer molecular weights and molecular weights between cross-links.

According to the methods of the present invention, the polymer composition in step a) comprises a cyclic or linear carbonate monomer content in mol percentage of the total copolymer, of 40% mol to 85% mol, preferably 50% mol to 70% mol, more preferably 60% mol to 70% mol. The carbonate can be trimethylene carbonate.

According to the methods of the present invention, the crosslinking radical initiator is chosen from the group photo-initiator, thermal initiator, redox initiator. The radical initiator can be any commercially available initiator.

In a more preferred embodiment of the present invention, the methods comprise in step b) 0.001% wt to 0.1% wt, preferably 0.005% wt to 0.075% wt, more preferably 0.01% wt to 0.05% wt, most preferably 0.025% wt of the radical initiator by weight percentage of the total weight of the polymer composition.

In yet another preferred embodiment of the present invention, step b) comprises a solvent being acetone, dichloromethane, chloroform, carbontetrachloride, ethylene carbonate, propylene carbonate, dimethylsulfoxide, toluene, benzene, tetrahydrofuran or 1,4-dioxane. Acetone has the formula $CH_3COCH_3$ Dichloromethane has the formula $CH_2Cl_2$, chloroform $CHCl_2$, carbontetrachloride $CCl_4$. Ethylene carbonate and propylene carbonate are and ester of ethylene glycol or propylene glycol, respectively, and carbonic acid. They have the formula $C_3H_4O_3$ and $C_4H_6O_3$. Dimethylsulfoxide (DMSO) is an organosulfur compound with the formula $(CH_3)_2SO$. Benzene and toluene are aromatic hydrocarbons with the formula $C_6H_6$ and $C_7H_8$, respectively. Tetrahydrofuran (THF) has the formula $C_4H_8O$. 1,4-dioxane has the formula $C_4H_8O_2$.

According to the methods of the present invention, the irradiation in step d) is ultraviolet, visible, infrared microwave, or gamma irradiation. Ultraviolet irradiation has a wavelength between 1 and 400 nm, visible irradiation between 400 and 800 nm, and infrared irradiation between 0.8 μm and 300 μm. Microwave irradiation has the frequencies between 300 MHz (0.3 GHz) and 300 GHz.

In a preferred embodiment of the present invention, the gamma irradiation comprises a radiation of 10 to 150 kGy, preferably 20 to 120 kGy, more preferably 25 to 100 kGy. KGy means KiloGray (radiation unit of measure). The source can be cobalt$^{60}$, or any other gamma-source.

According to the methods of the present invention, the desired shape of the polymer composition in step c) is obtained by compression molding, extrusion, injection molding or casting at a temperature from 20° C. to 200° C., preferably 100° C. to 180° C., more preferably 130° C. to 150° C., most preferably 140° C. A polymer film can be obtained by compression molding, a method of molding in which the molding material, generally preheated, is first placed in an open, heated mold cavity. The mold is closed with a top force or plug member, pressure is applied to force the material into contact with all mold areas, while heat and pressure are maintained until the molding material has cured. Extrusion is a process used to create objects of a fixed cross-sectional profile. A material is pushed or drawn through a die of the desired cross-section. The two main advantages of this process over other manufacturing processes are its ability to create very complex cross-sections and work materials that are brittle, because the material only encounters compressive and shear stresses. It also forms finished parts with an excellent surface finish. Injection molding is a manufacturing process for producing parts of polymer materials. The material is fed into a heated barrel, mixed, and forced into a mold cavity where it cools and hardens to the configuration of the mold cavity. After a product is designed, molds are made in usually either steel or aluminium, and precision-machined to form the features of the desired part. Injection molding is widely used for manufacturing a variety of parts. Casting can be by solvent casting. Solvent casting is a process for forming thermoplastic articles by dipping a male mold into a solution or dispersion of the resin and drawing off the solvent to leave a layer of plastic film adhering to the mold.

According to the methods of the present invention, the desired shape of the polymer composition in step c) is a film which has a thickness of 1 μm to 1000 μm, preferably 10 μm to 750 μm, more preferably 50 μm to 600 μm.

In a preferred embodiment, the preparation of the polymer composition comprises ring-opening polymerization and/or a polycondensation.

Ring-opening polymerization is a form of addition polymerization, in which the terminal end of a polymer acts as a reactive center, where further cyclic monomers join to form a larger polymer chain through propagation. The treatment of some cyclic compounds with initiators and catalysts brings about cleavage of the ring followed by polymerization to yield oligomers or polymers. The reaction is commonly carried out under inert conditions (argon, nitrogen or vacuum) and under heating.

Polycondensation is a chemical condensation leading to the formation of a polymer by the linking of molecules of a monomer and the releasing of a small molecule such as water.

In a more preferred embodiment, the preparation of the polymer composition in the methods of the present invention is carried out at a temperature between 100° C. and 160° C., more preferably between 120° C. and 150° C.

According to another aspect, degradable polymer networks are obtainable by the methods of the present invention.

According to yet another aspect of the present invention, the degradable polymer network is used for coating surfaces, as a protective layer for thermal insulation and/or for anti-oxidation insulation, for the manufacture of packaging materials.

According to still another aspect of the present invention, the degradable polymer network is used for preparing implants, in tissue engineering, cell culturing, or drug delivery.

The present invention is further described by the figures and Examples herewith. The figures and Examples illustrate the present invention and do not aim to limit its scope.

FIGURES

In the examples, reference is made to the appended figures wherein:

FIG. 1. Effect of initial polymer molecular weight and irradiation dose on gel content (A) and swelling ratio in chloroform (B) of PTMC films cross-linked by gamma irradiation in vacuo.

Figure 2:
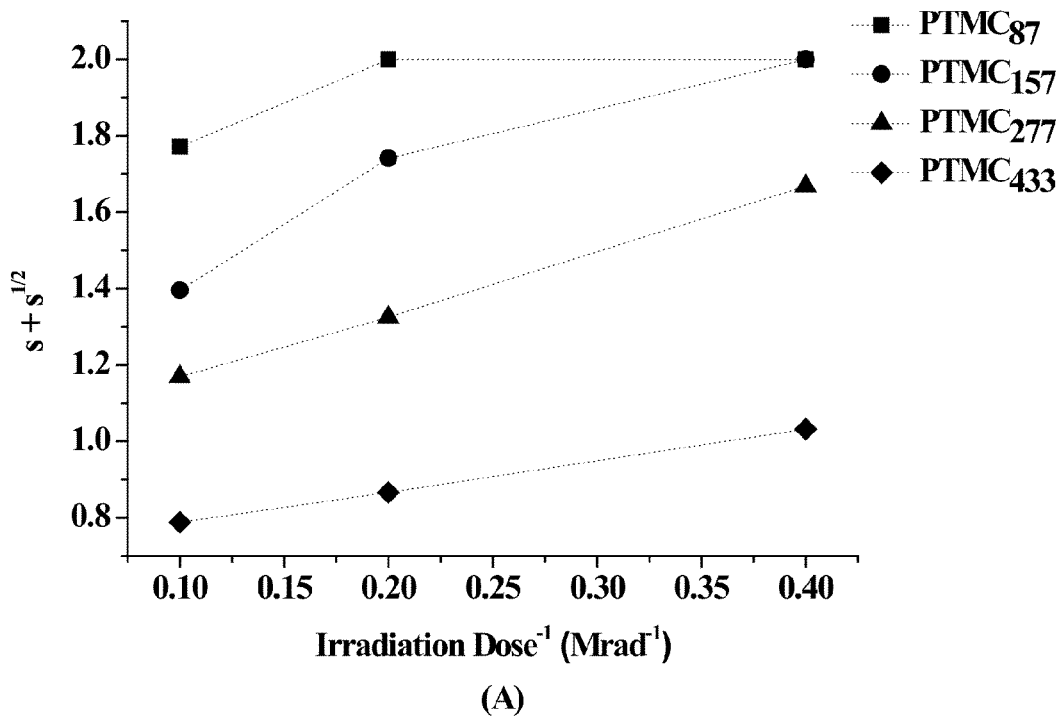
Figure 2:
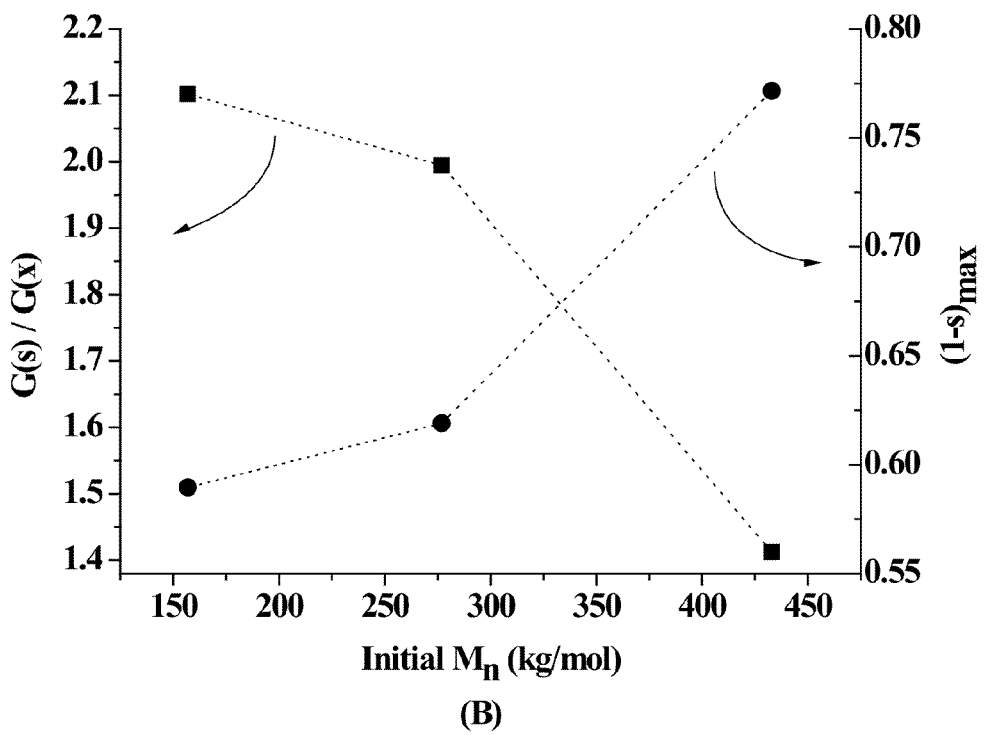

FIG. 2. Charlesby-Pinner plots for networks prepared by gamma-irradiation of PTMC films of different initial molecular weights (A), and the effect of initial polymer molecular weight on the ratio of the radiation chemical yield of chain scission to cross-linking $((G(s)/G(x))$ and on the maximum gel percentage that can be obtained $(1-s)_{max})$ (B).

Figure 3:
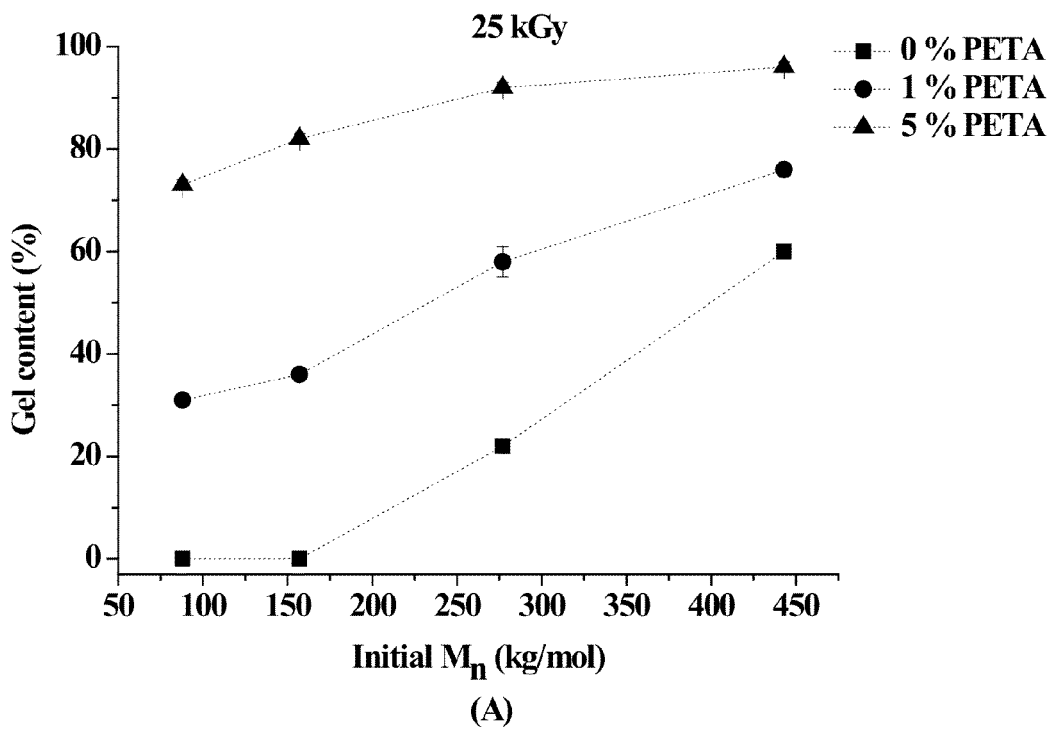
Figure 3:
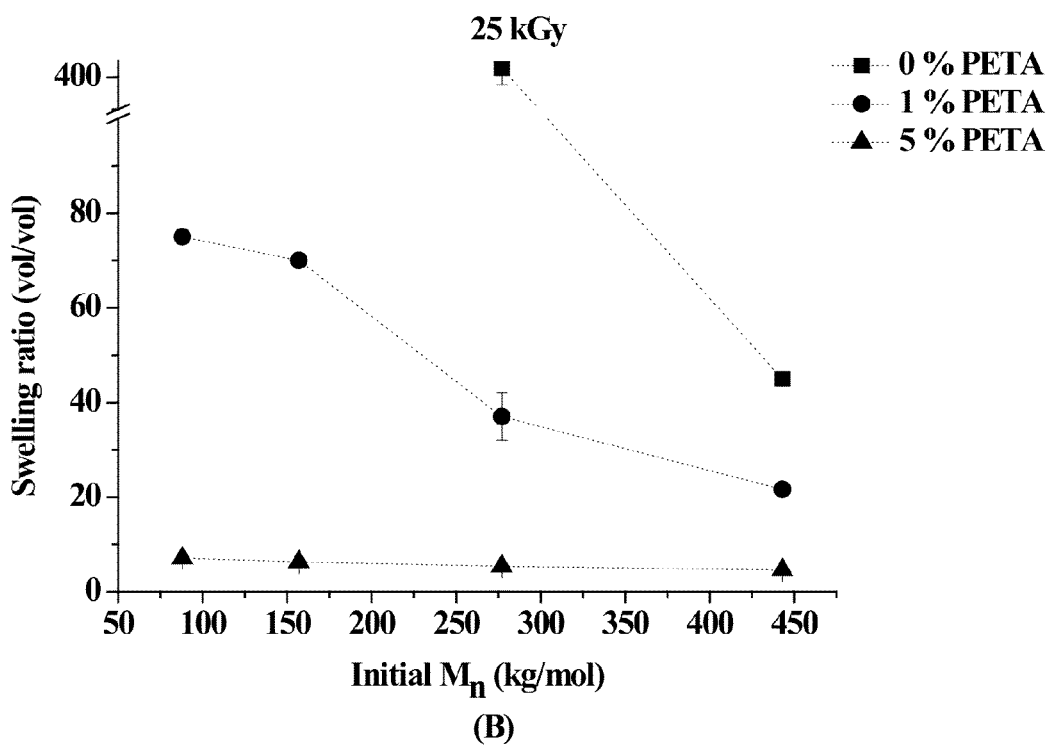

FIG. 3. The effect of incorporating PETA on gel content (A) and equilibrium swelling ratio in chloroform (B) of PTMC networks formed upon irradiation of PTMC polymers of different initial molecular weights at 25 kGy.

Figure 4:
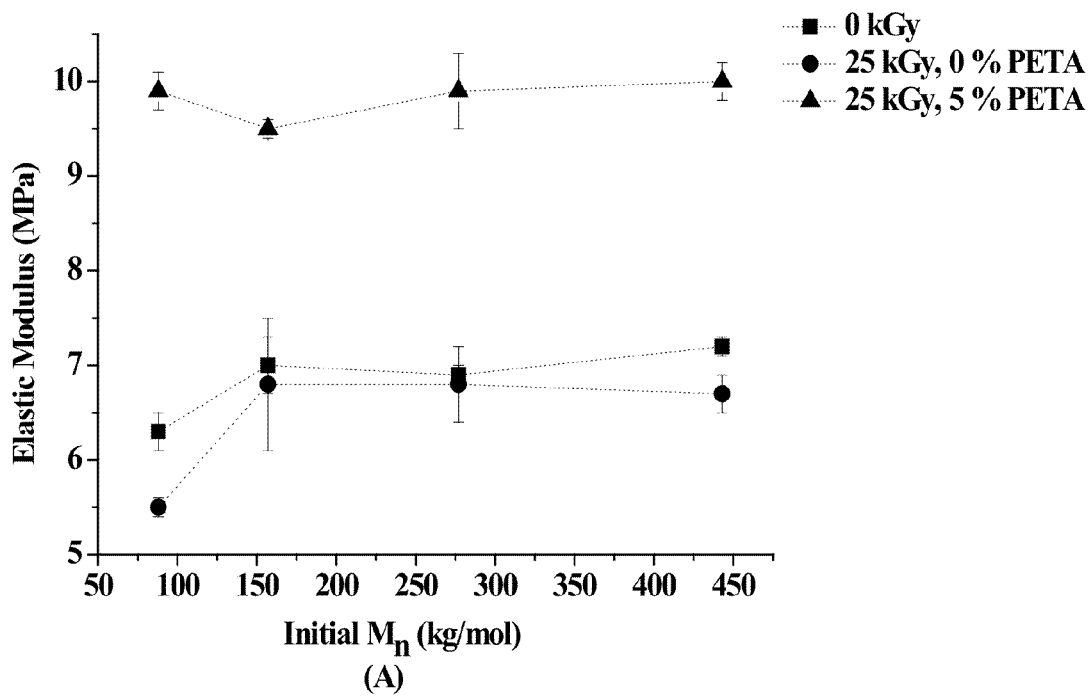
Figure 4:
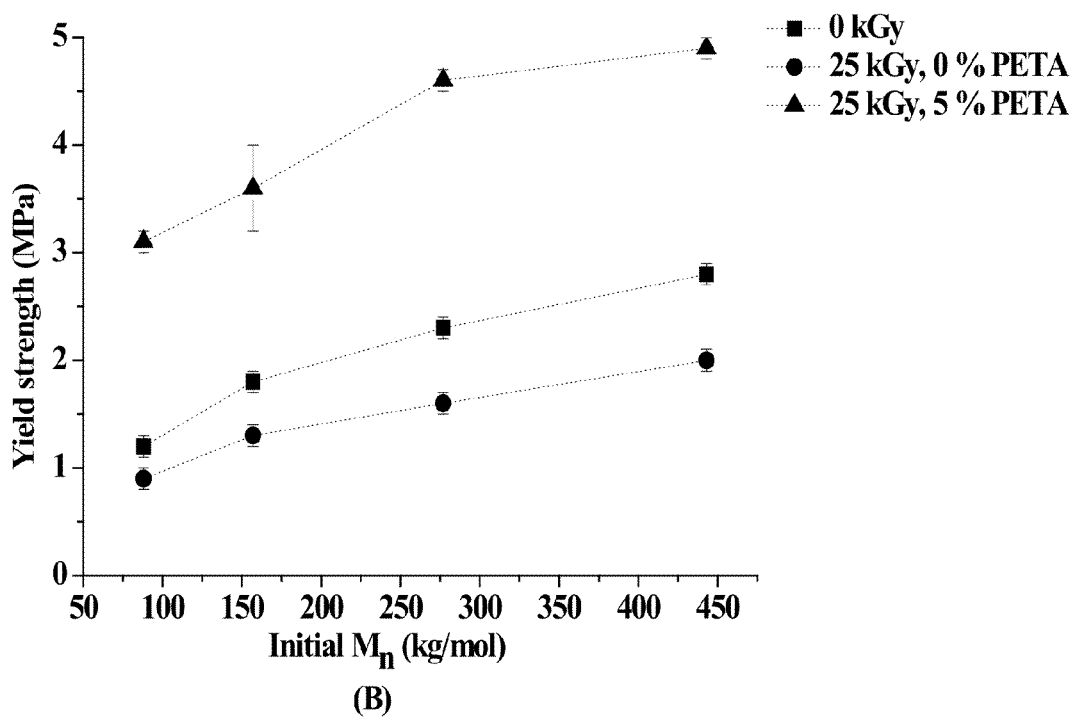
Figure 4:
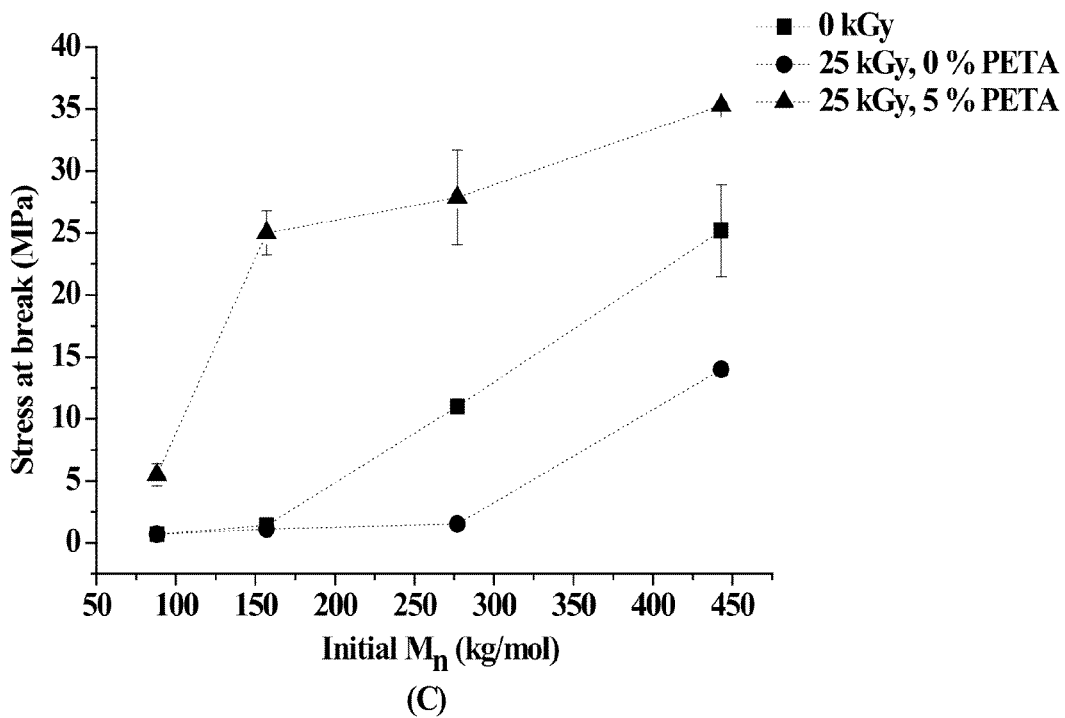
Figure 4:
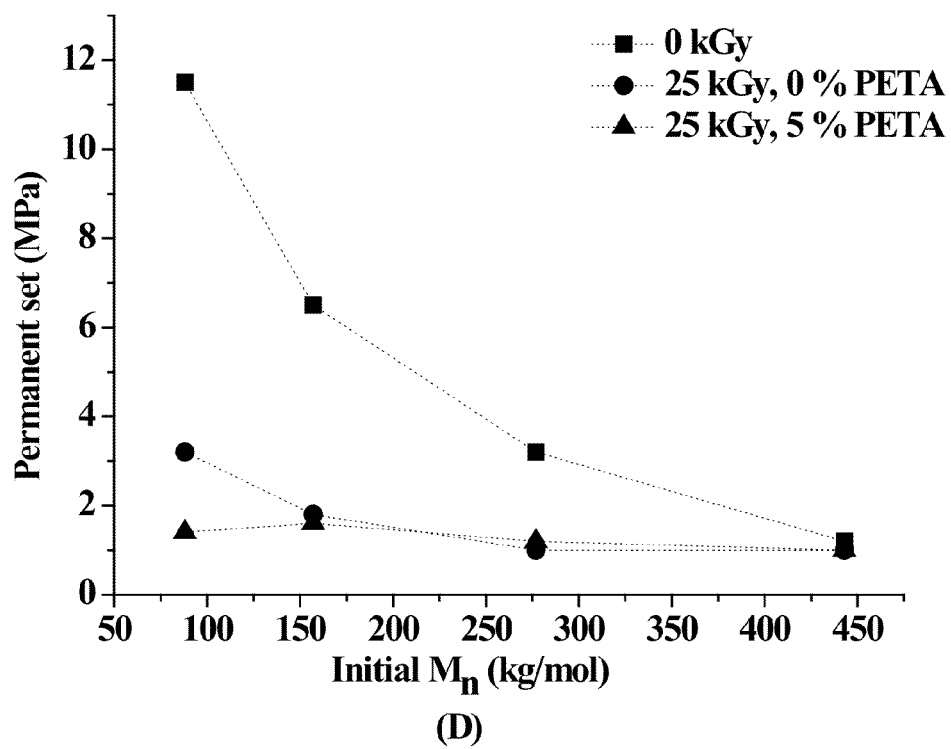

FIG. 4. Effect of initial molecular weight, irradiation dose, and PETA content on elastic modulus (A), yield strength (B), stress at break (C), and permanent set (D) values of PTMC films.

Figure 5:
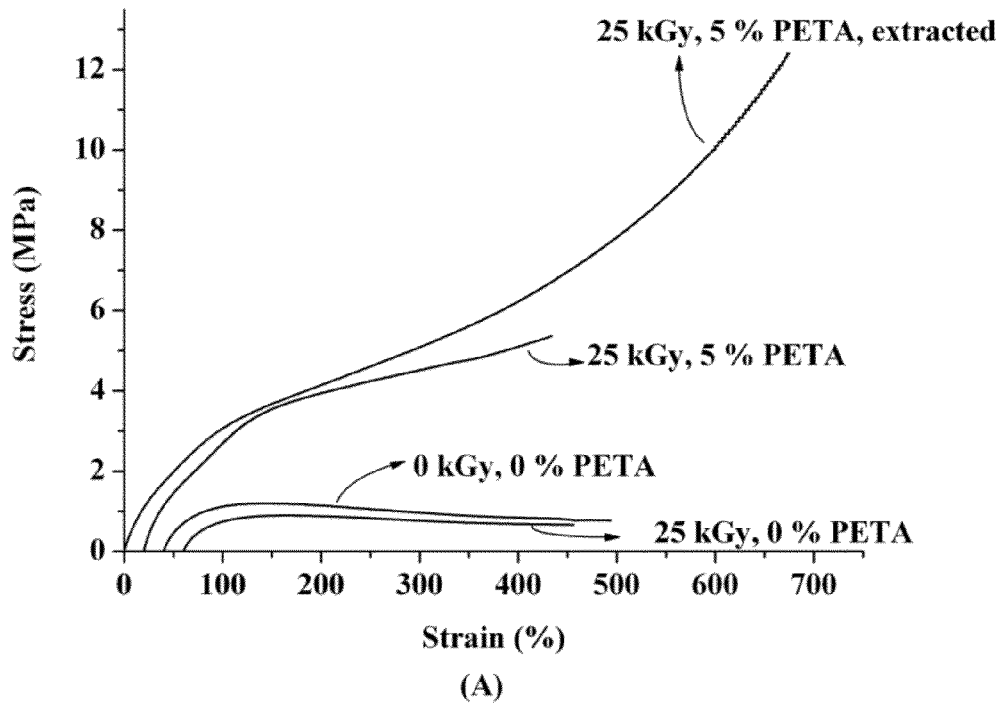
Figure 5:
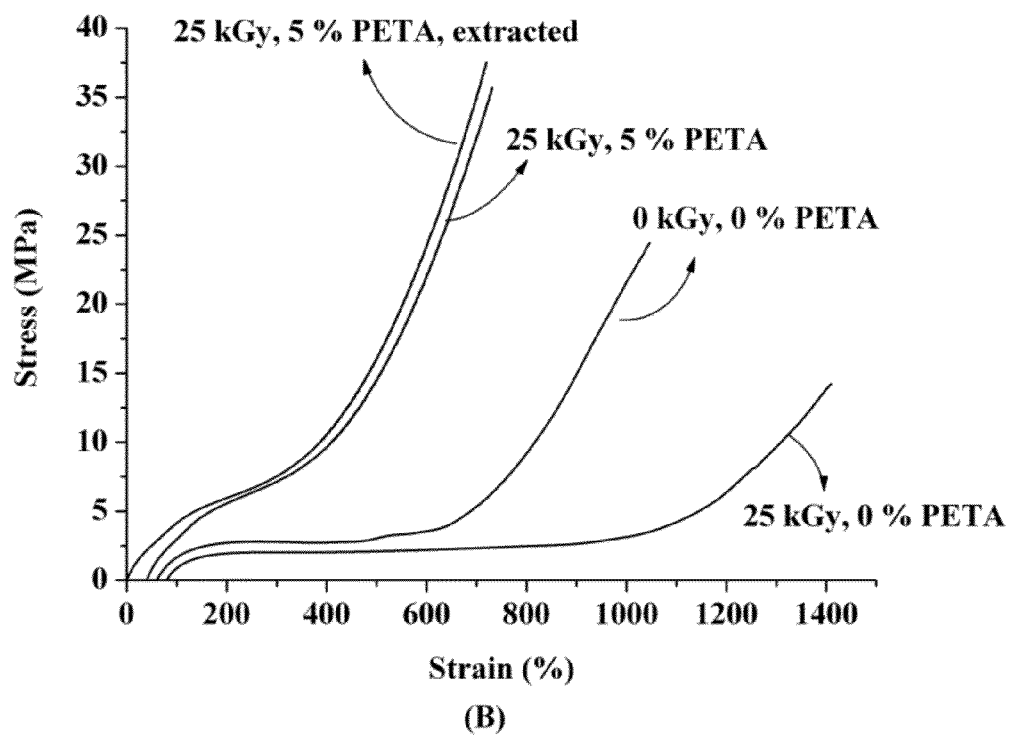

FIG. 5. Effect of gamma irradiation, PETA content, and ethanol extraction on stress-strain behaviour of $PTMC_{88}$ (A) and $PTMC_{443}$. (B) (curves are offset for clarity)

Figure 6:
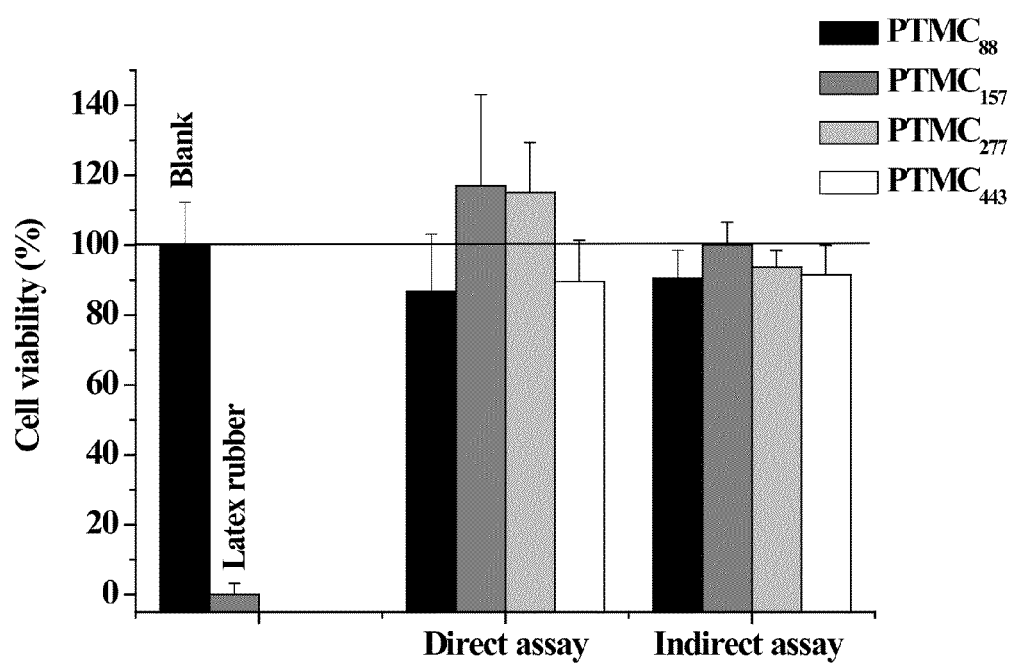

FIG. 6. The viability of fibroblasts cultured in direct- or indirect contact with PTMC networks. The networks were prepared by irradiating films of PTMC of different molecular weights in the presence of 5 wt % PETA. The first two bars indicate cell viability of the blank (culture medium only) and positive controls, respectively.

Figure 7:
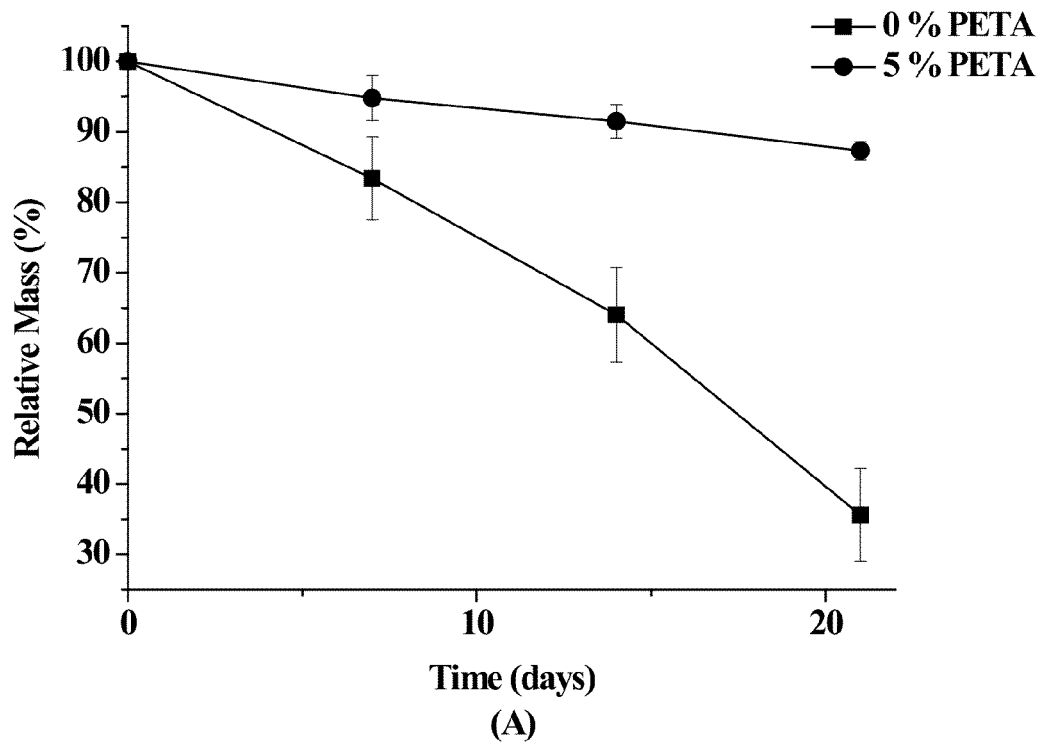
Figure 7:
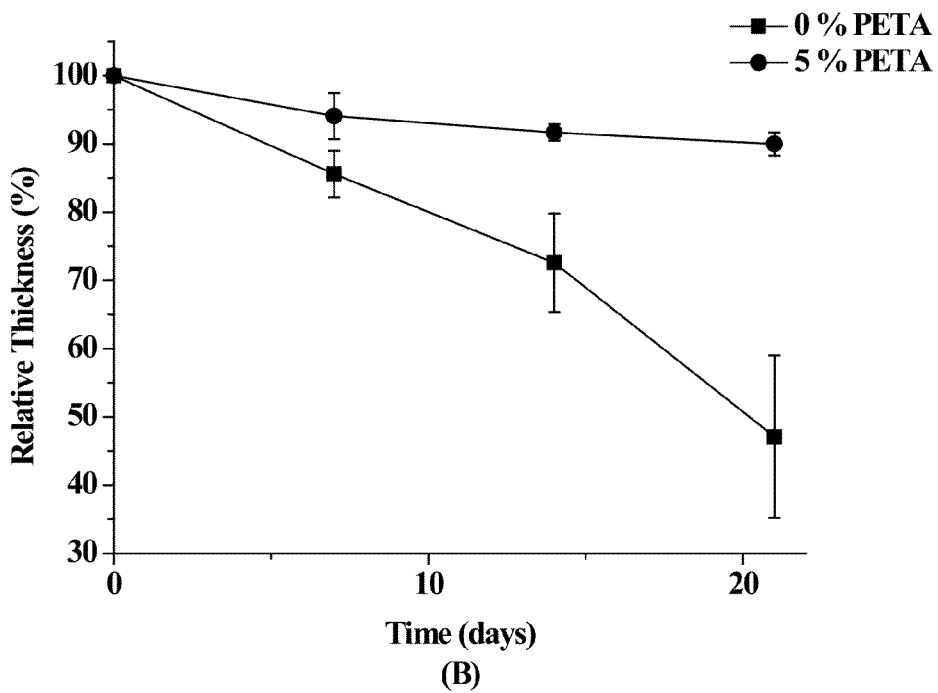
Figure 7:
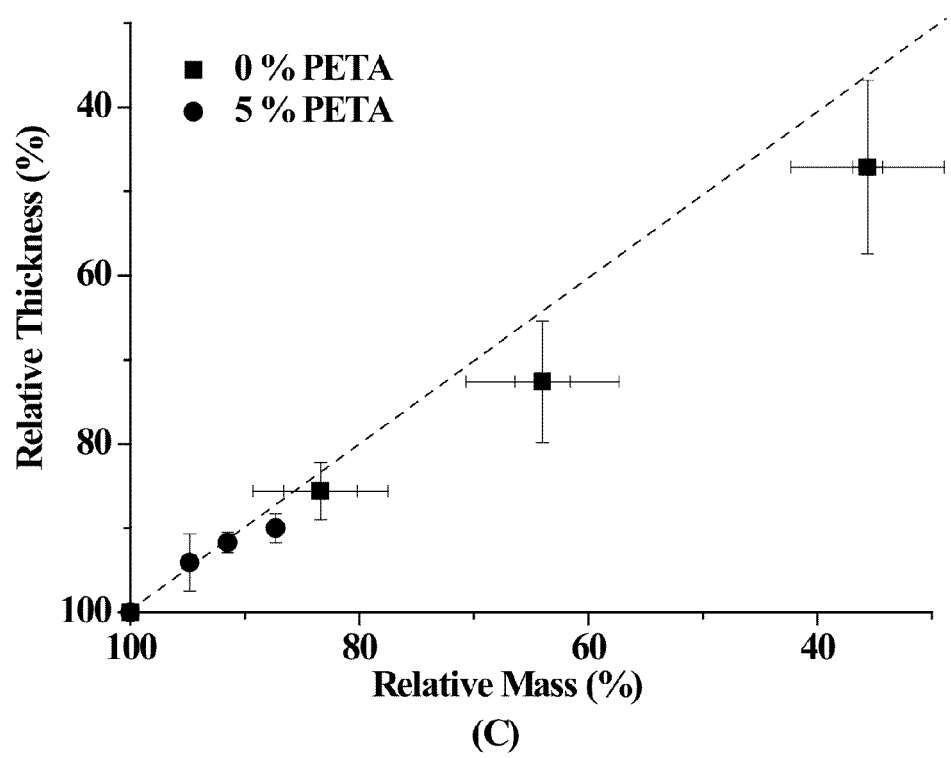

FIG. 7. Erosion in aqueous solutions of cholesterol esterase (CE) of $PTMC_{443}$ films gamma-irradiated in the presence (5 wt %) and absence of PETA. The figure shows the relative thickness (A) and relative mass (B) in time and the relationship between the relative thickness and relative mass (C).

Figure 8:
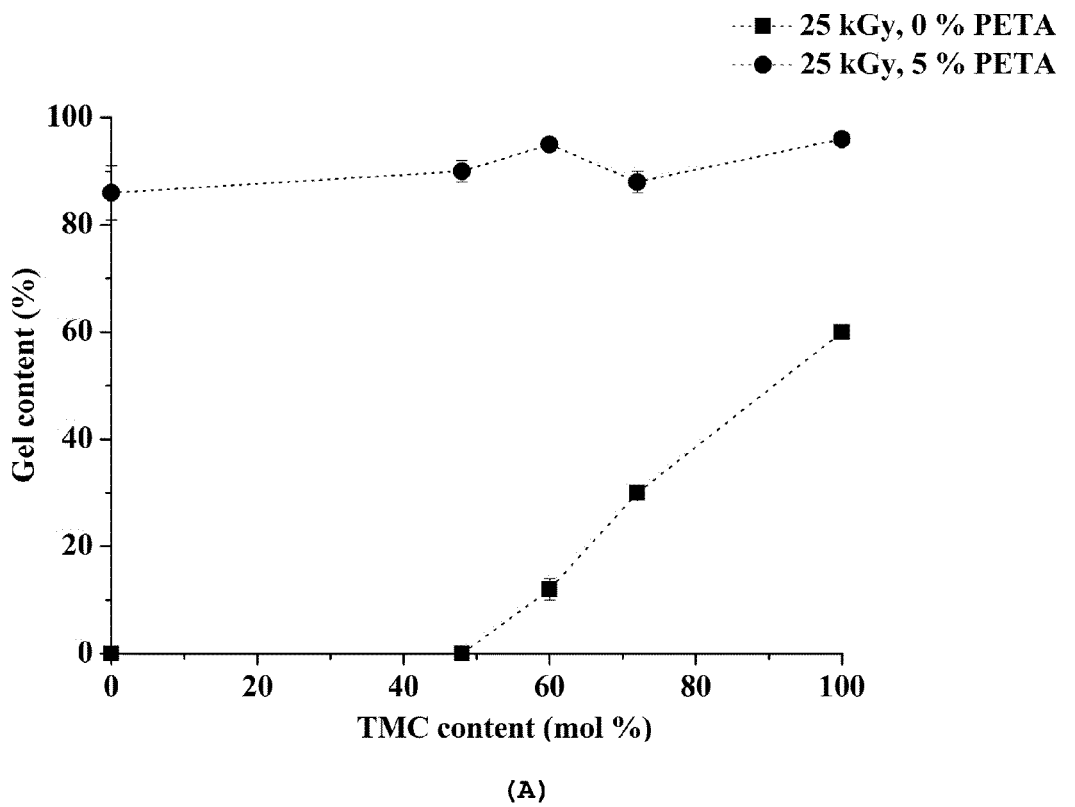
Figure 8:
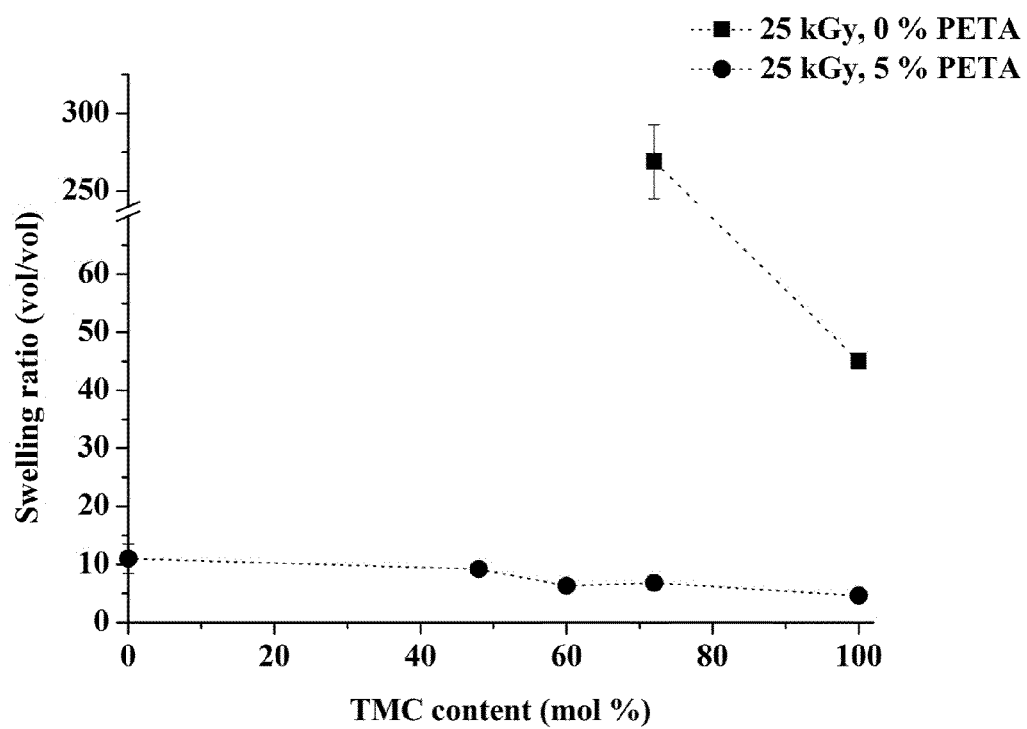

FIG. 8. Effect of the copolymer composition and the incorporation of PETA on the gel content (A) and swelling ratio (B) of networks formed by gamma irradiation (25 kGy) of P(TMC-DLLA) co-polymer films.

Figure 9:
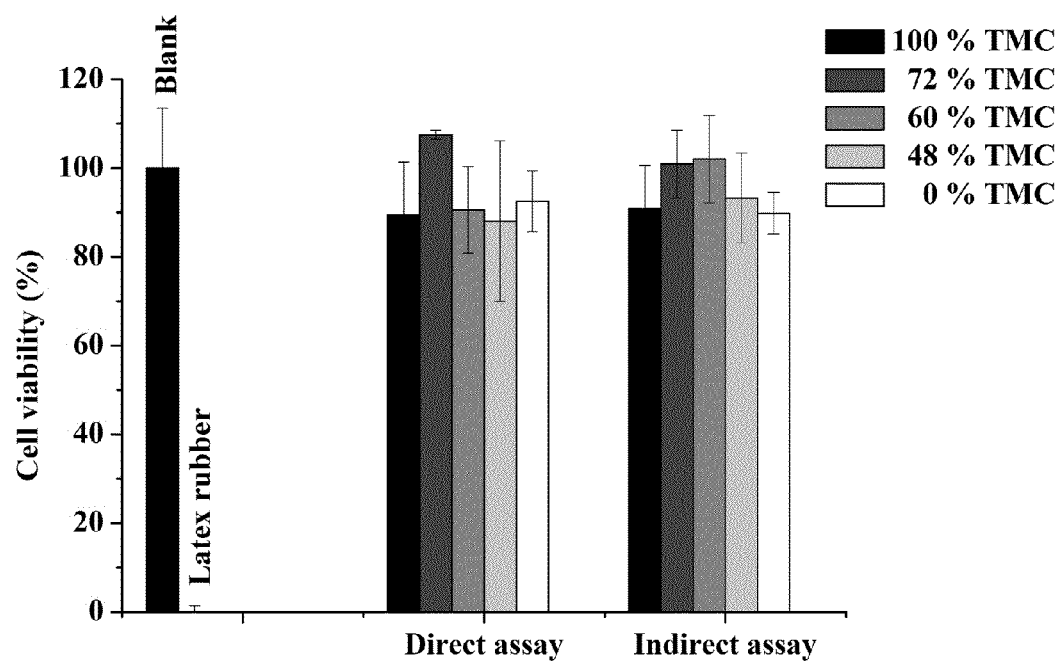

FIG. 9. The viability of fibroblasts cultured in direct- or indirect contact with non-extracted co-polymer networks. The networks were prepared by irradiating films of co-polymers in the presence of 5 wt % PETA at 25 kGy. The first two bars indicate the cell viability of the blanks (culture medium only, negative controls) and positive controls, respectively.

Figure 10:
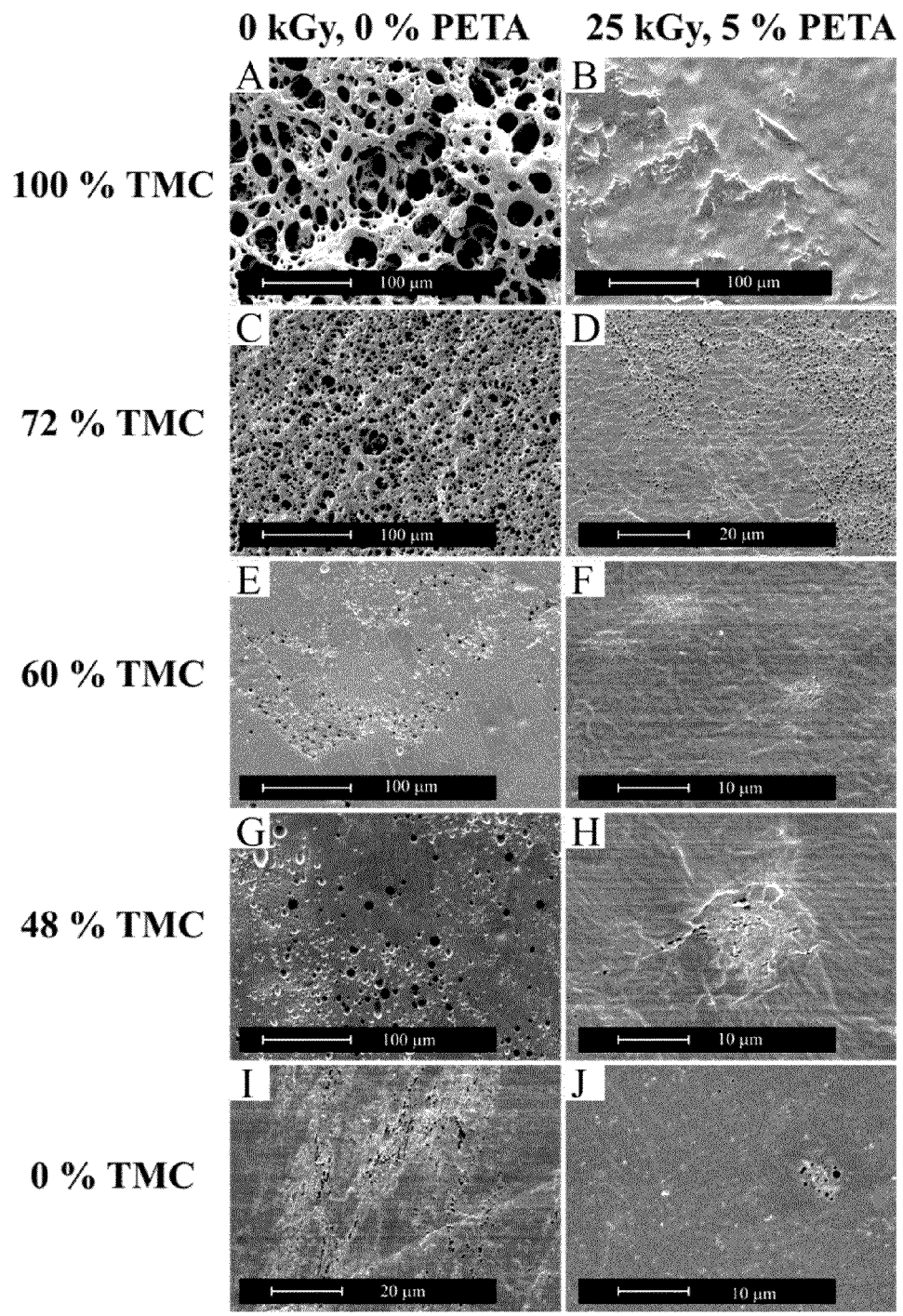

FIG. 10. SEM micrographs showing the macrophage-mediated erosion of non-irradiated P(TMC-DLLA) co-polymer films (A,C,E,G,I), and non-extracted network films prepared by gamma irradiating co-polymer films containing 5% PETA (B,D,F,H,J) after 15 days of culture.

Figure 11:
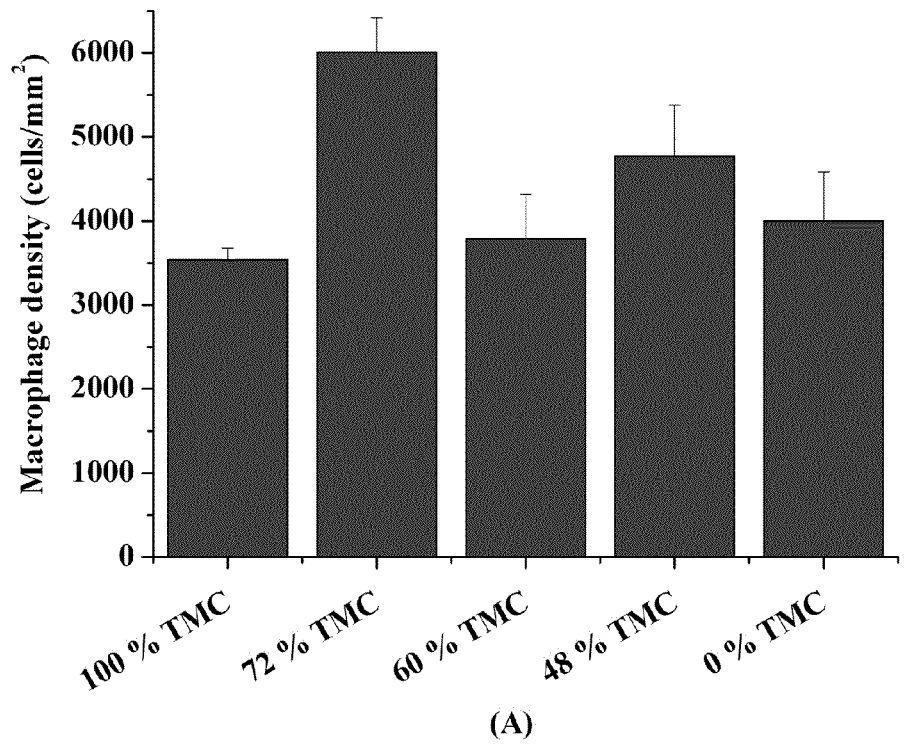
Figure 11:
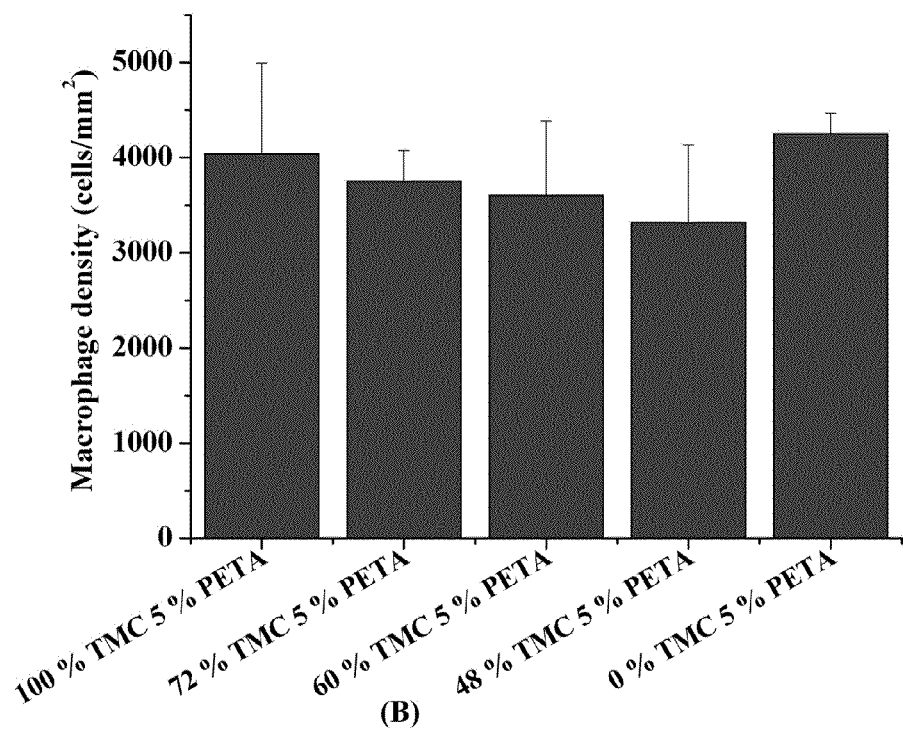

FIG. 11. Density of macrophages on different non-irradiated P(TMC-DLLA) co-polymer films (A), and non-extracted network films prepared by gamma irradiating co-polymer films containing 5% PETA (B) after 14 days of culture.

Figure 12:
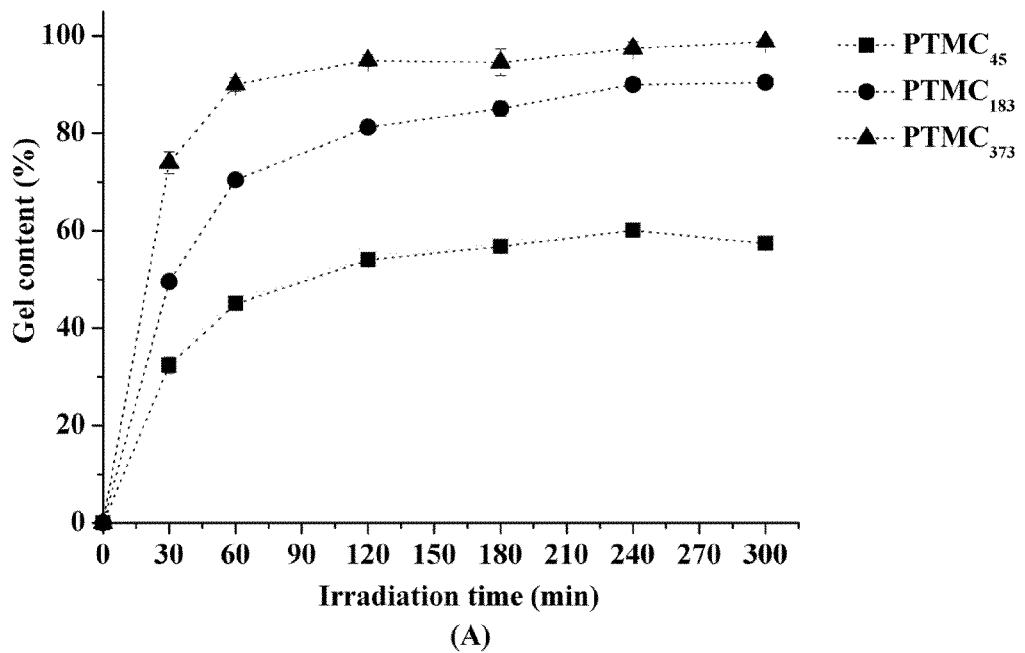
Figure 12:
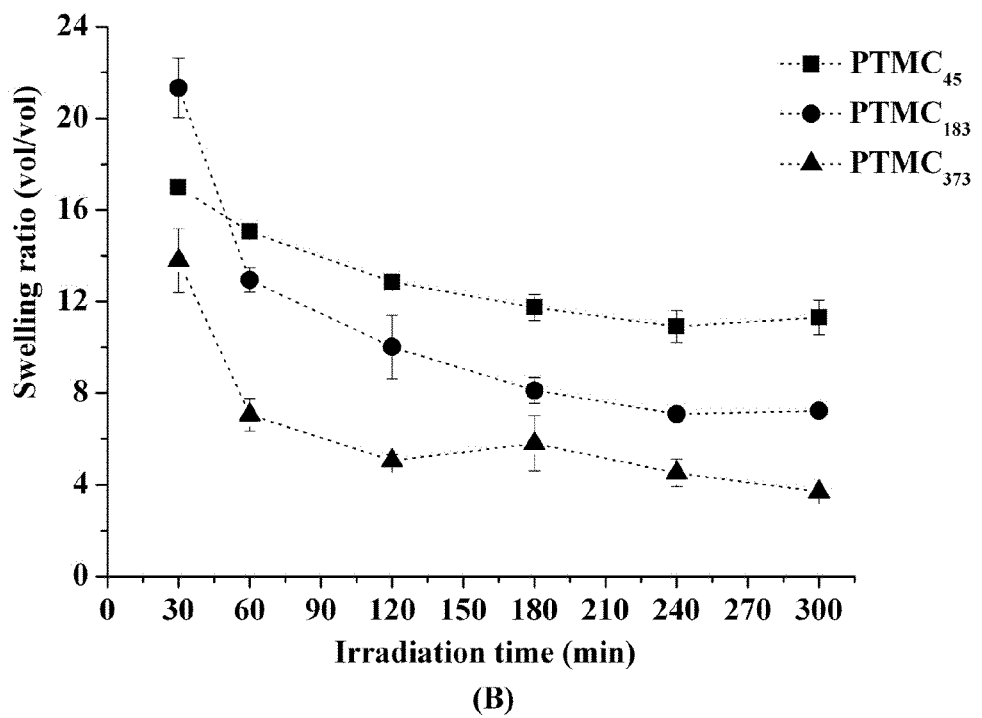

FIG. 12. Effect of UV-irradiation time and initial polymer molecular weight on gel content (A) and swelling ratio in chloroform (B) of PTMC homopolymer films that contain 5 wt % PETA and 0.025 wt % photoinitiator and exposed to 254 nm UV light. Values are expressed as mean±standard deviation, (n=3).

Figure 13:
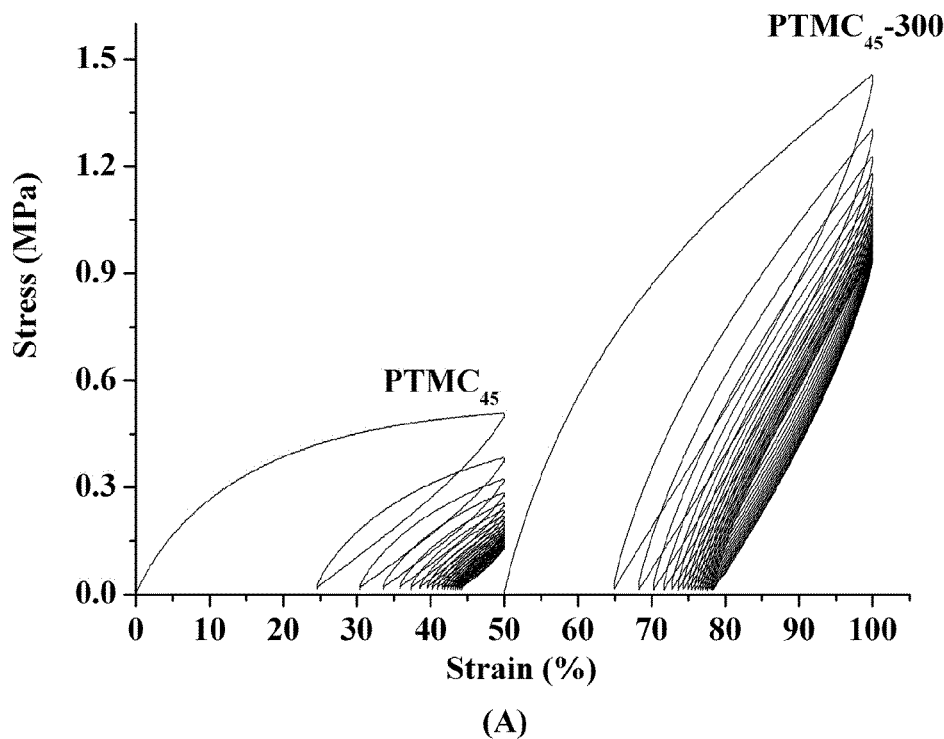
Figure 13:
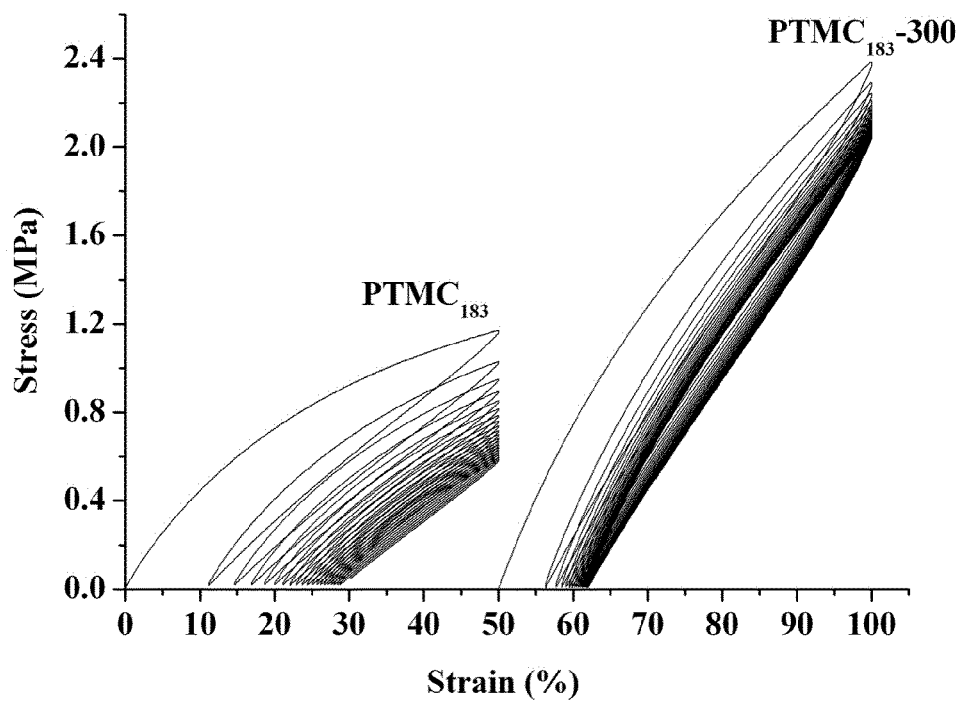
Figure 13:
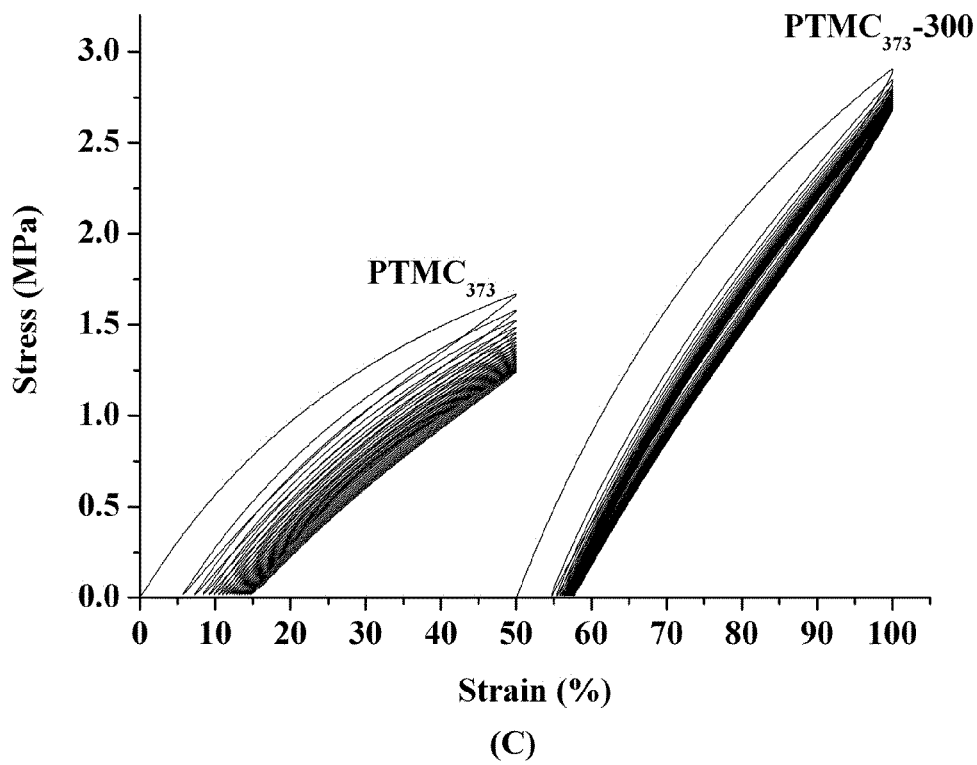
Figure 13:
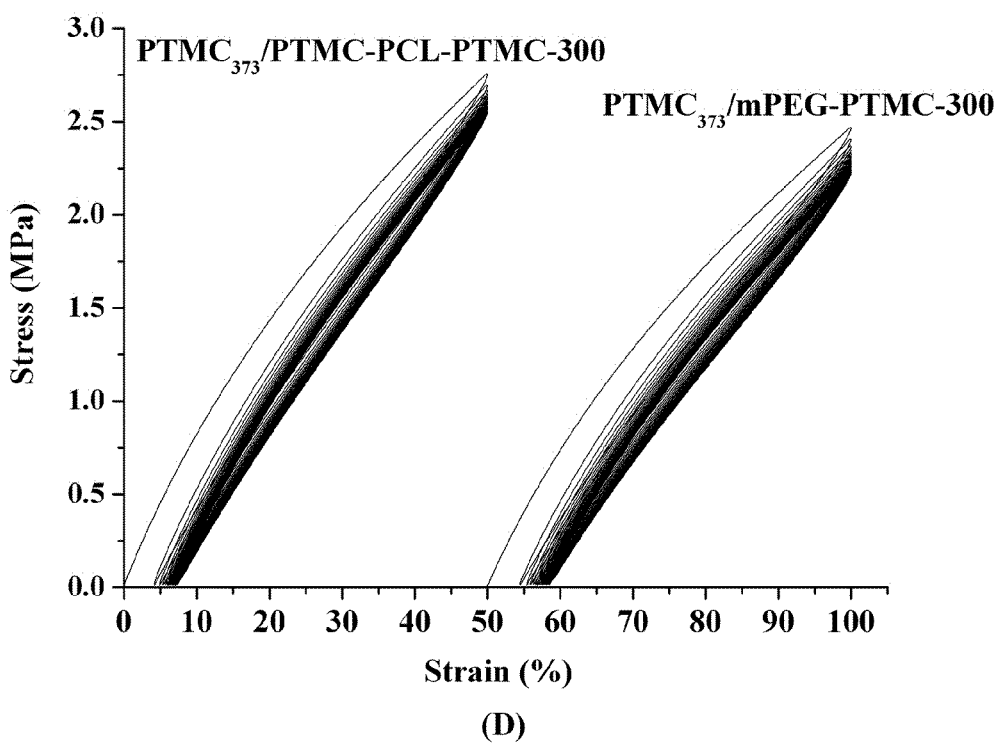

FIG. 13. Effect of photocross-linking on the hysteresis behaviour of PTMC polymers and networks in cyclic tensile tests. The curves show repetitive (20 cycles) application of 50% strain on PTMC homopolymers of different molecular weights before ($PTMC_x$) and after photocross-linking in the presence of PETA and photoinitiator by 300 minutes of UV exposure (A,B,C). FIG. D shows the behaviour of photocross-linked blends under dynamic loading.

Figure 14:
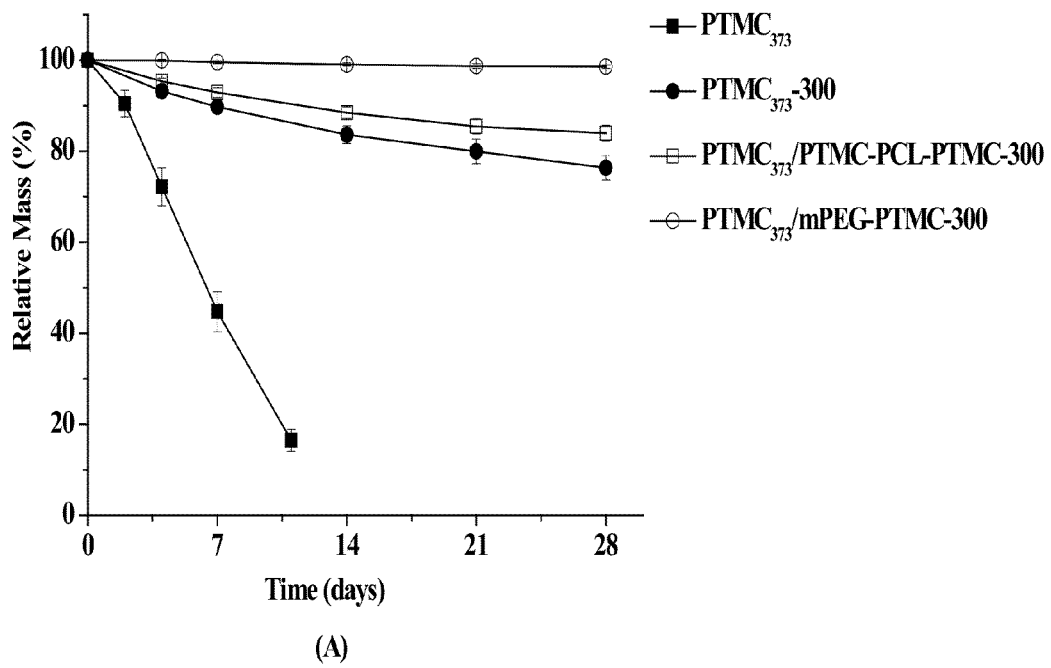
Figure 14:
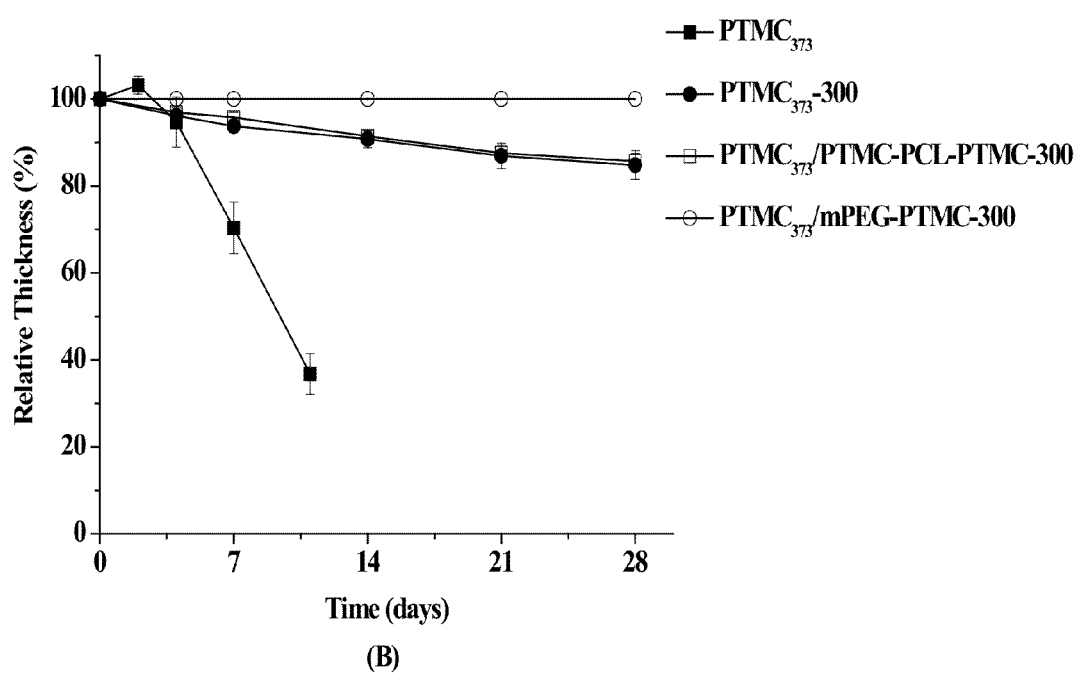

FIG. 14. Effect of photocross-linking and blending with block copolymers on in vitro enzymatic erosion of $PTMC_{373}$-based networks: Decrease in relative mass in time (A) and decrease in relative thickness in time (B).

Figure 15:
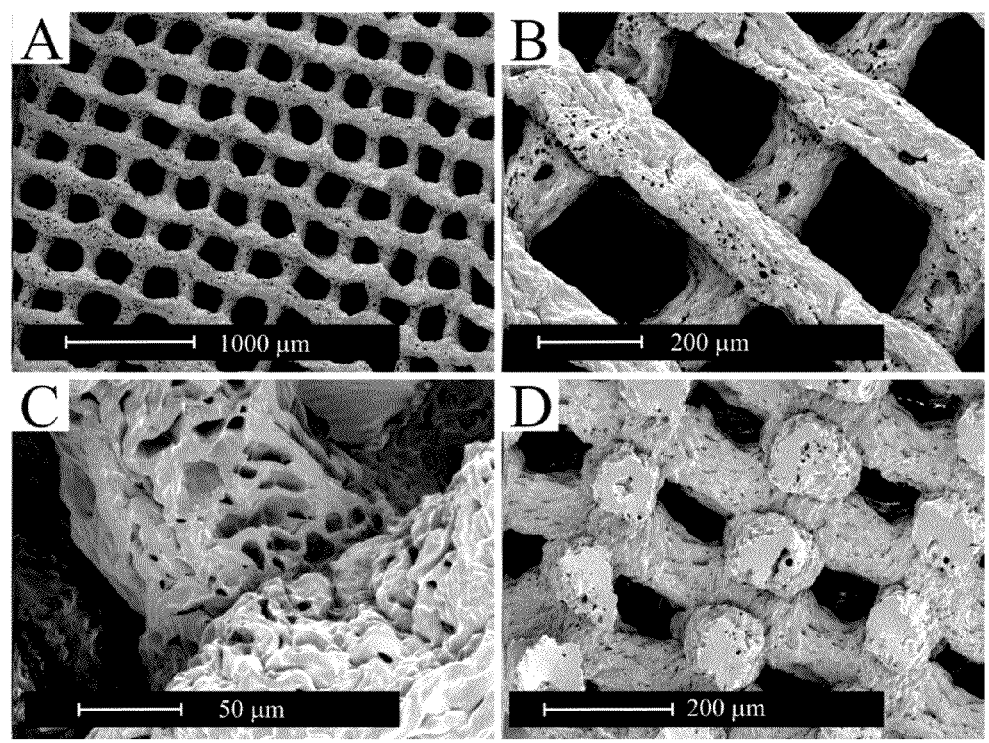

FIG. 15. SEM micrographs of the photocross-linked porous scaffolds prepared from $PTMC_{373}$. A and B show the top view of a scaffold. Microporosity of the fibres is illustrated in C. A cross section of a scaffold is given in D.

Figure 16:
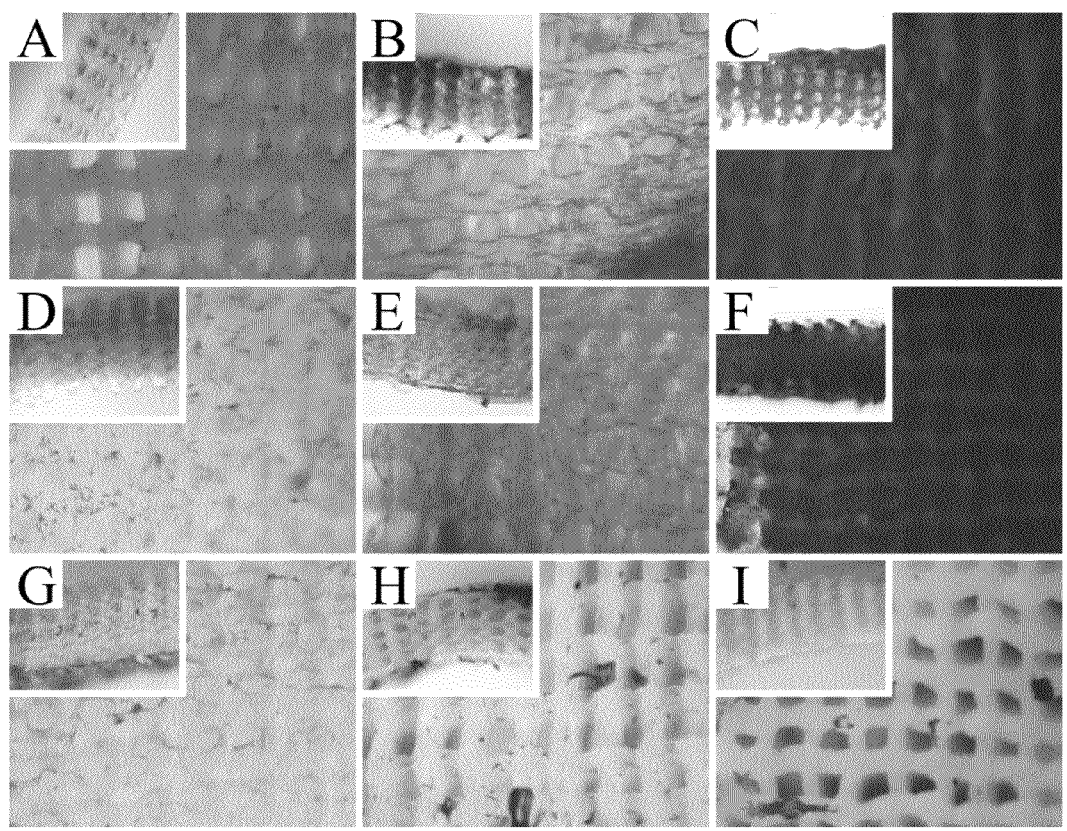

FIG. 16. Micrographs showing the viable cells on/in 3D fabricated and photocross-linked scaffolds prepared from $PTMC_{373}$ (A,B,C), $PTMC_{373}$/PTMC-PCL-PTMC (D,E,F), $PTMC_{373}$/mPEG-PTMC (G,H,I) after cell seeding (A, D, G), and after 5 days (B, E, H) and 10 days (C, F, I) of hMSC culturing. A cross-section of each scaffold is shown in insets.

Figure 17:
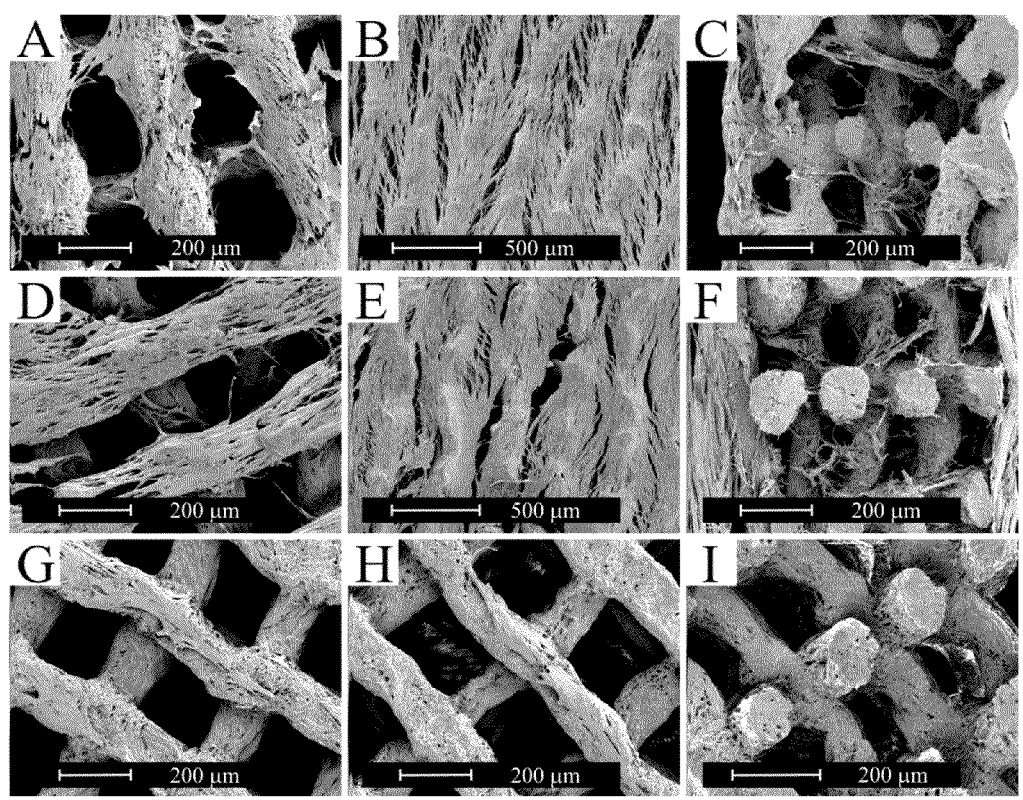

FIG. 17. SEM micrographs showing hMSCs on/in the 3D fabricated and photocross-linked scaffolds prepared from $PTMC_{373}$ (A,B,C), $PTMC_{373}$/PTMC-PCL-PTMC (D,E,F), $PTMC_{373}$/mPEG-PTMC (G,H,I) after 5 days (A,D,G) and 10 days (top-view B,E,H, cross section (C,F,I) of hMSC culturing.

Figure 18:
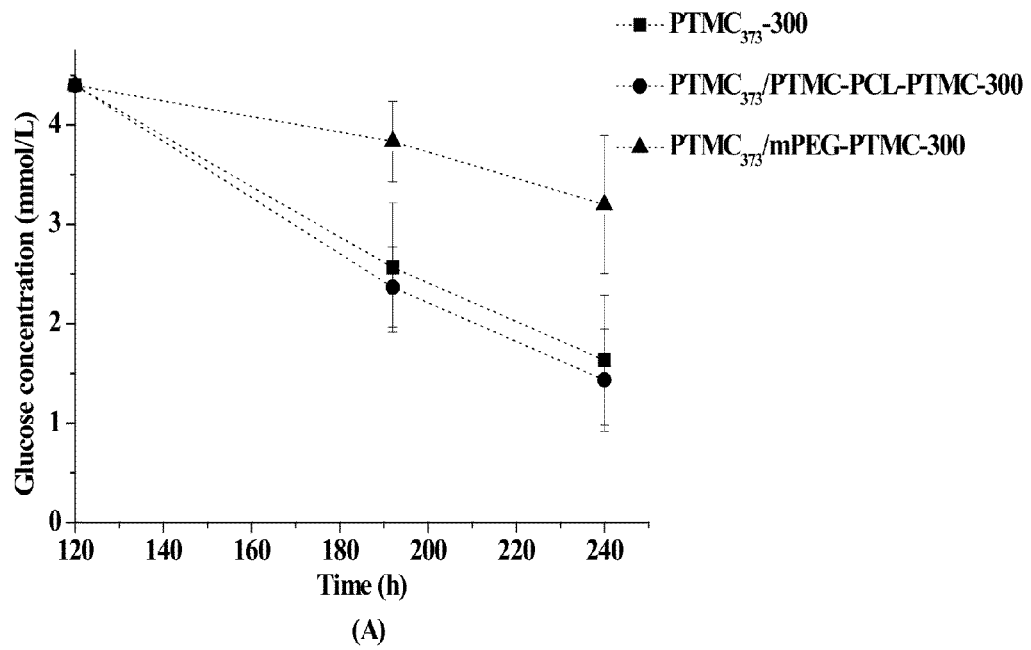
Figure 18:
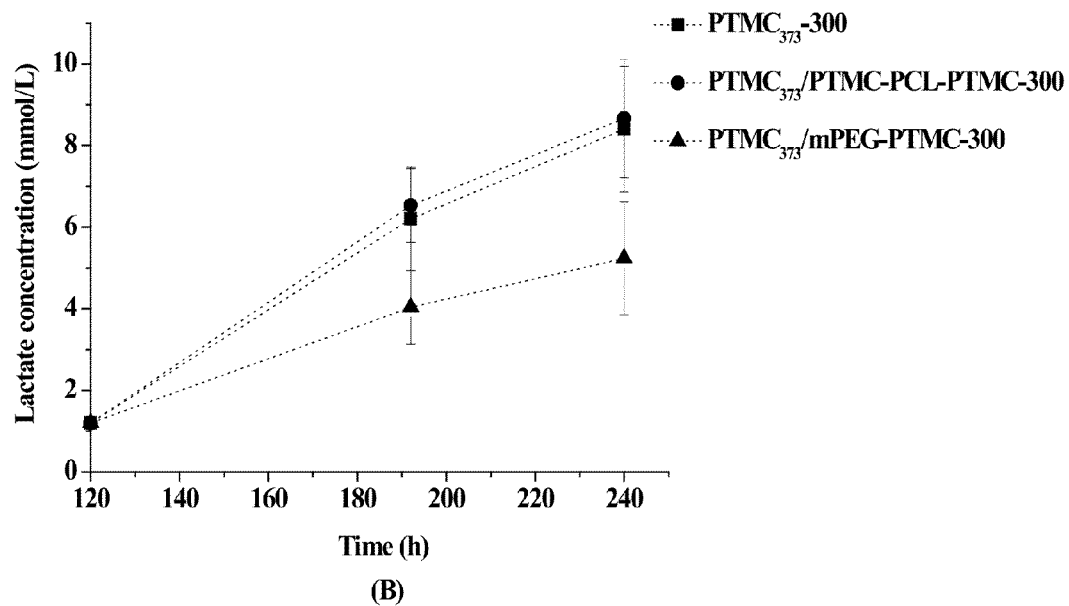
Figure 19:
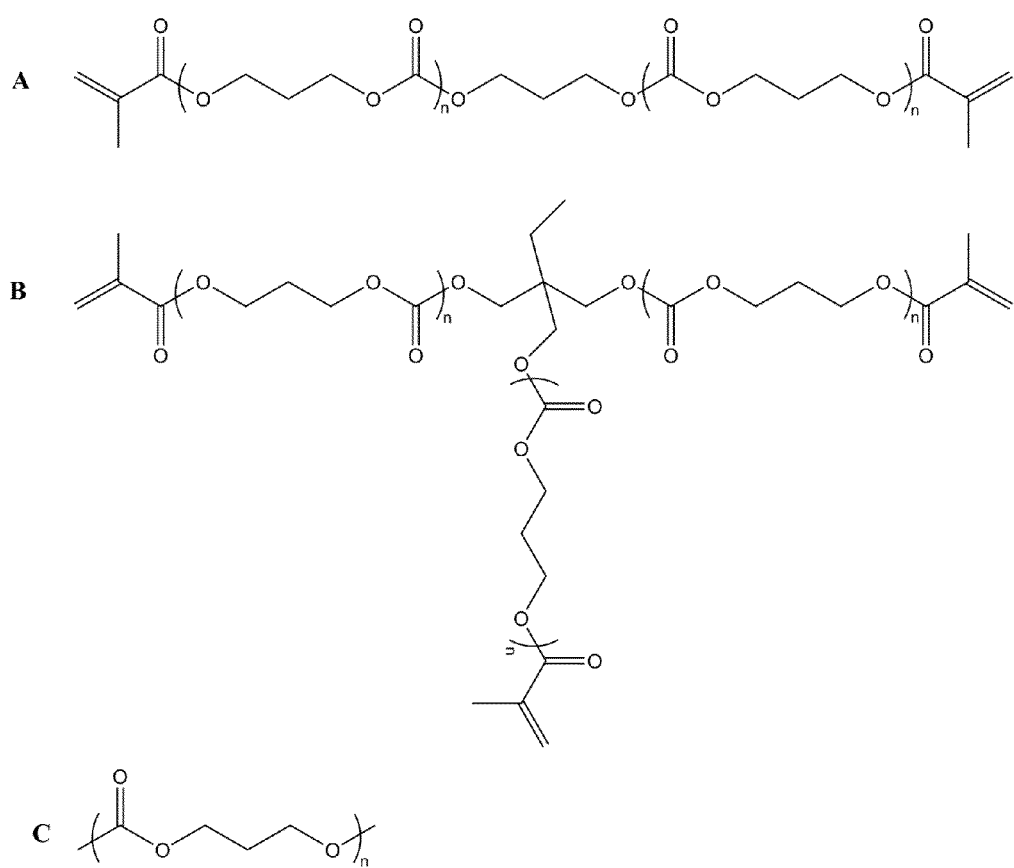

FIG. 18. Glucose consumption and lactate production of hMSCs cultured in 3D fabricated and photocross-linked PTMC-based scaffolds FIG. 19. Chemical structures of the synthesized two-armed PTMC macromer (DMAC) (A), three-armed PTMC macromer (TMAC) (B), and linear PTMC polymer (C).

Figure 20:
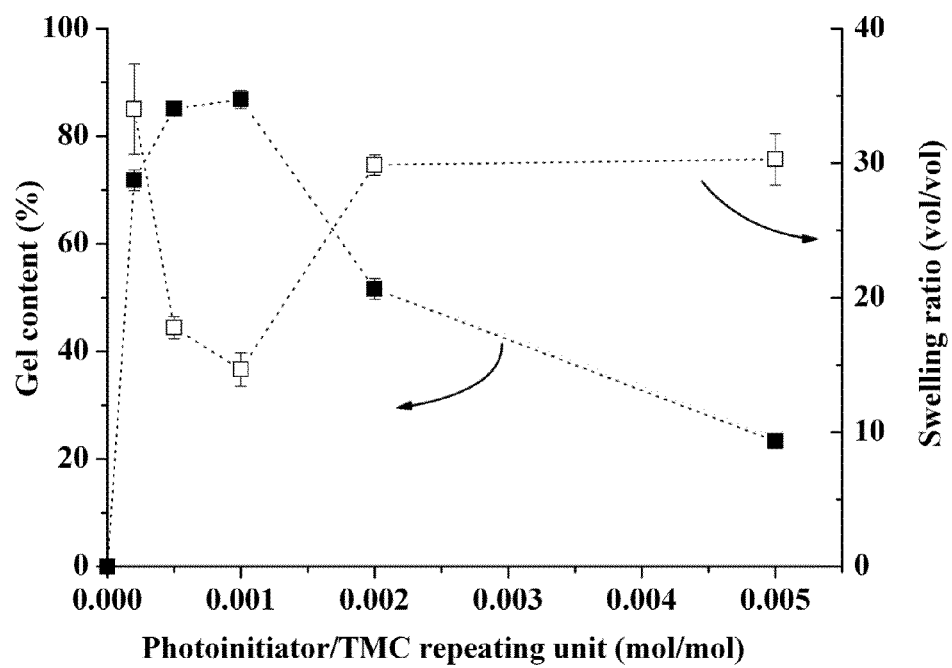

FIG. 20. Effect of Irgacure® 2959 photoinitiator concentration on the gel content and swelling ratio of networks obtained by UV irradiation of PTMC films for 120 min.

Figure 21:
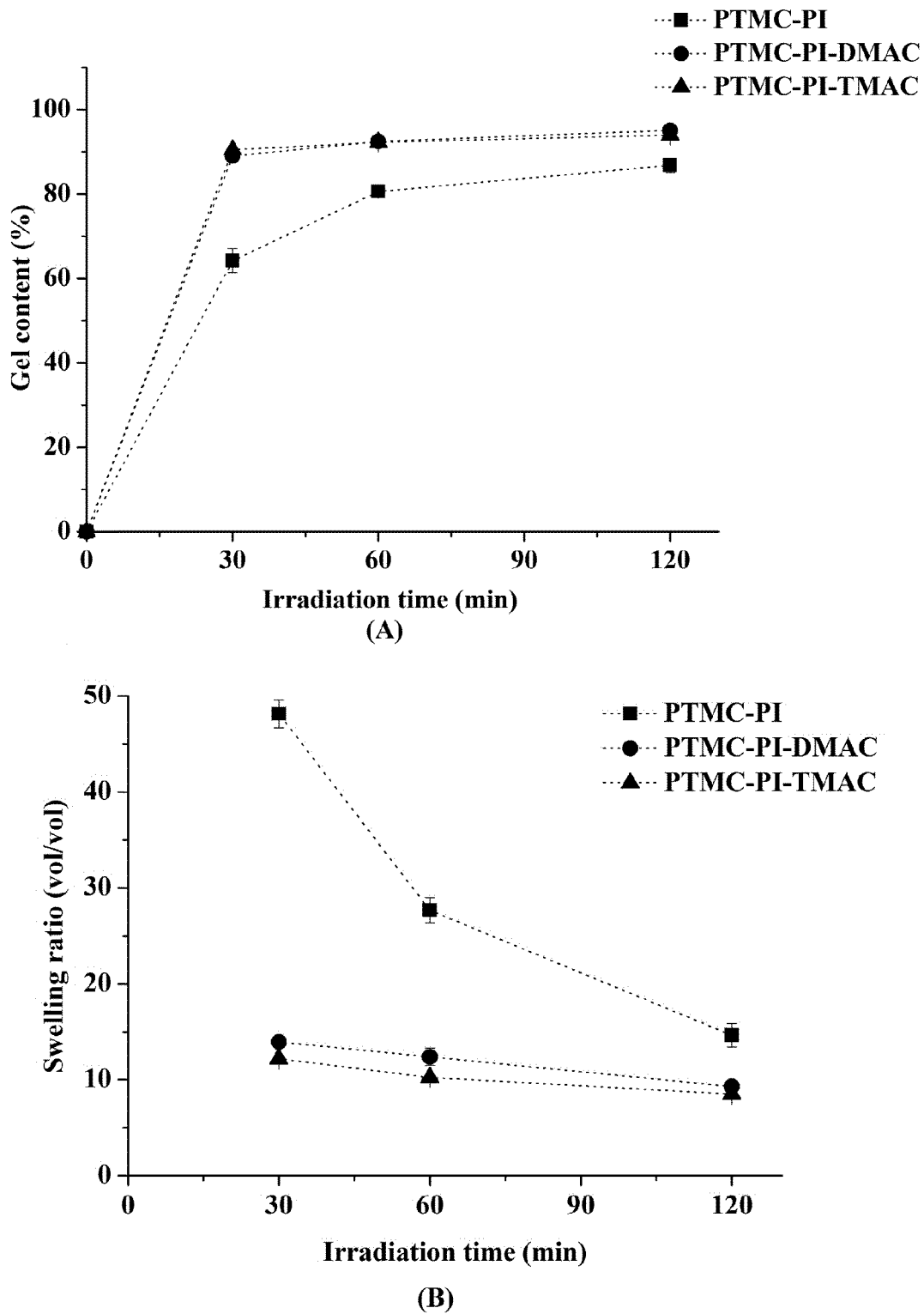

FIG. 21. Effect of irradiation time and cross-linking reagent used on gel content (A), and swelling ratio (B) of photocross-linked PTMC networks. In all PTMC films, the PI/(TMC repeating unit in the polymer) ratio was 1/1000. PTMC-PI films contain only photoinitiator and no PTMC macromer. For PTMC films containing DMAC and TMAC, the methacrylate/(TMC repeating unit in the polymer) ratio was 1/50.

Figure 22:
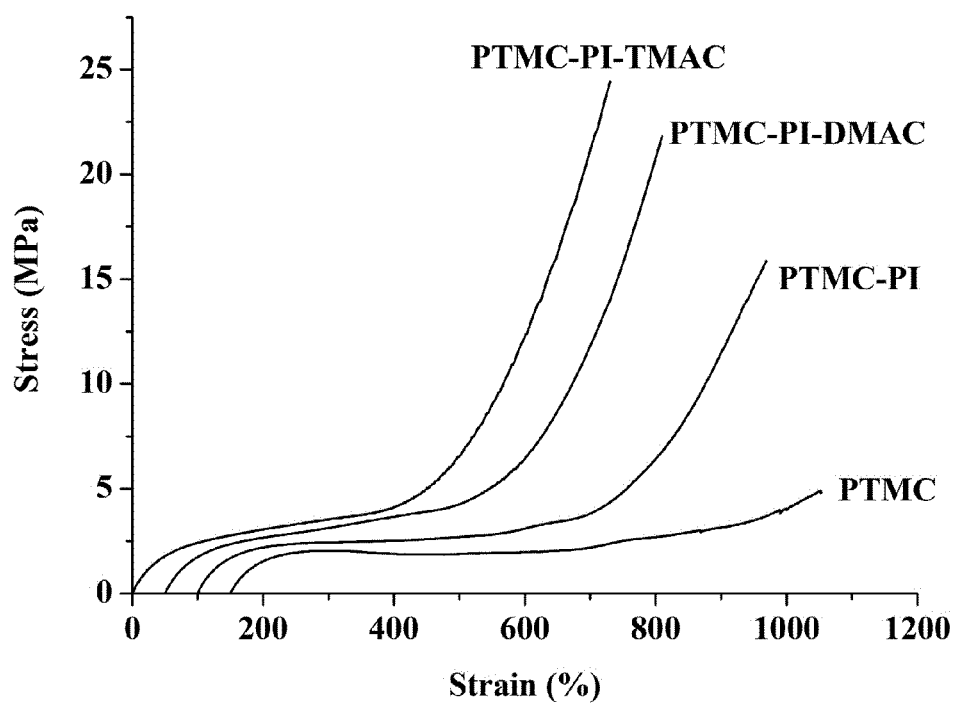

FIG. 22. Representative curves showing the stress-strain behaviour of linear and photocross-linked extracted PTMC network films. In all PTMC films, the PI/(TMC repeating unit in the polymer) ratio was 1/1000. PTMC-PI films contain only photoinitiator and no PTMC macromer. For PTMC films containing DMAC or TMAC, the methacrylate/(TMC repeating unit in the polymer) ratio was 1/50. Curves are offset for clarity.

Figure 23:
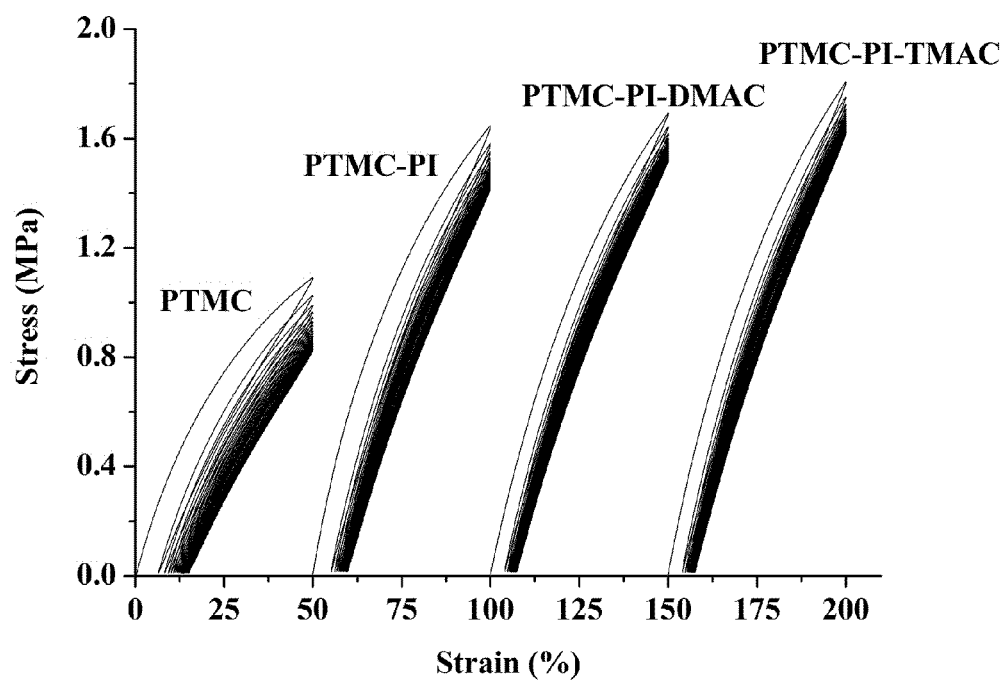

FIG. 23. Hysteresis behaviour of linear PTMC and UV-cross-linked (120 min) extracted PTMC network films containing only photoinitiator or photoinitiator and PTMC macromers. In all PTMC network films, the PI/(TMC repeating unit in the polymer) ratio was 1/1000. PTMC-PI network films contain only photoinitiator and no PTMC macromer. For PTMC network films containing DMAC or TMAC, the methacrylate/(TMC repeating unit in the polymer) ratio was 1/50. Curves are offset for clarity.

Figure 24:
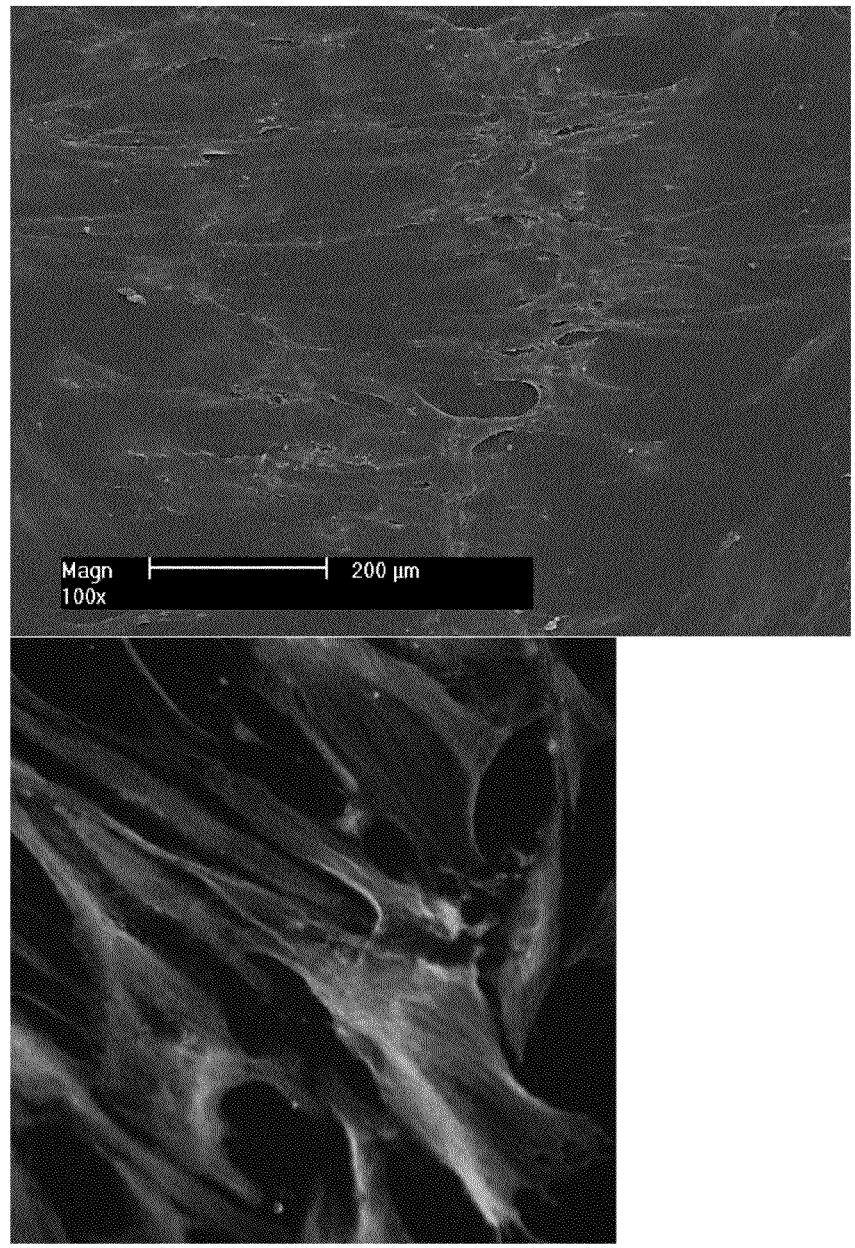

FIG. 24. SEM (left) and CLSM (right) micrographs showing hMSCs after 28 days of culturing on PTMC-PI-TMAC (1/50 methacrylate/TMC repeating unit in the polymer) films cross-linked by UV-irradiation for 120 min. The ratio of PI to TMC repeating unit in the polymer was 1/1000. In the figure, the nuclei are stained blue and the actin cytoskeleton is stained green.

Figure 25:
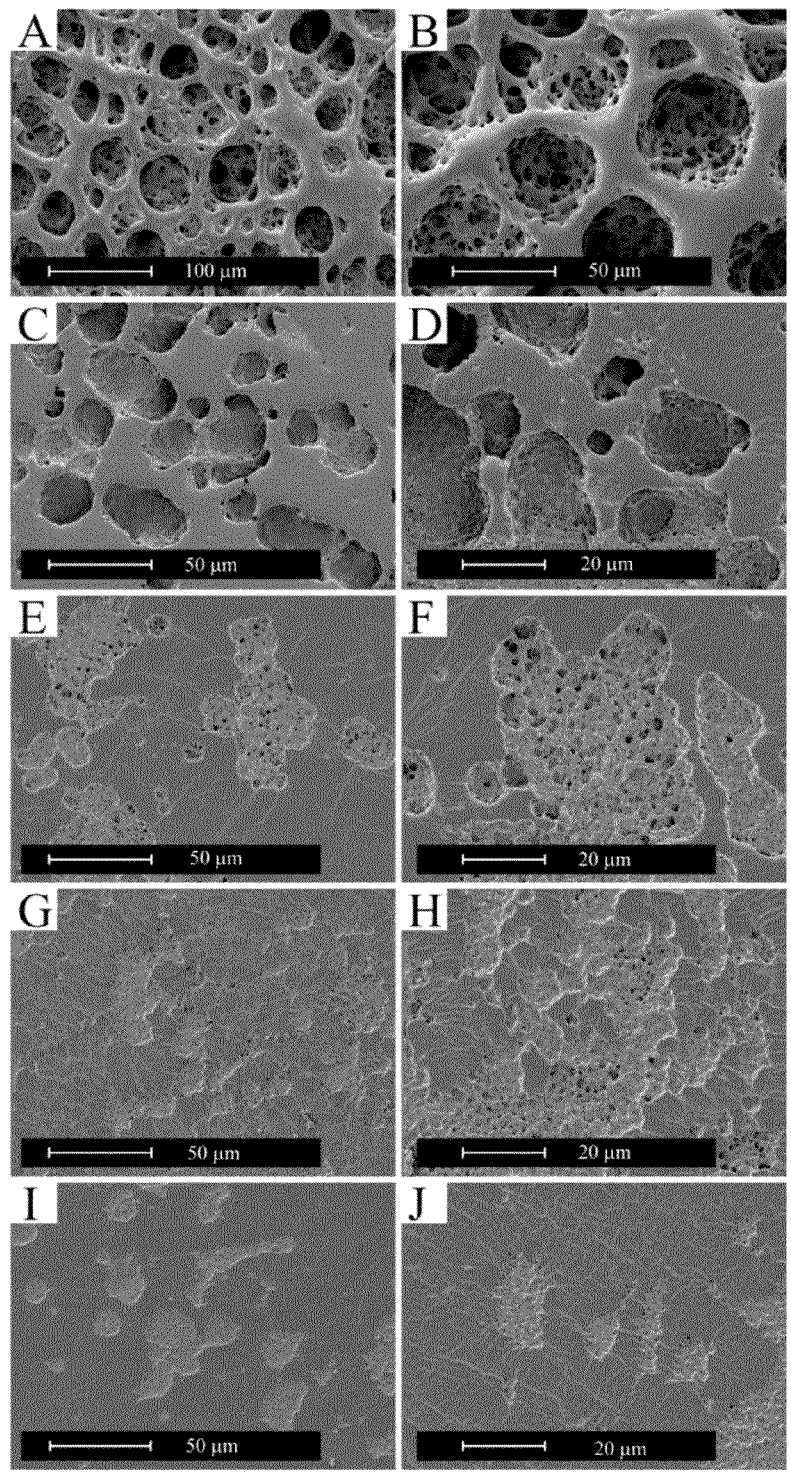

FIG. 25. SEM micrographs showing the macrophage-mediated erosion of films prepared from linear PTMC (A,B), and photocross-linked (120 min) extracted films having different ratios of methacrylate/(TMC repeating unit in the polymer): PTMC-PI (C,D), PTMC-PI-TMAC (1/200) (E,F), PTMC-PI-TMAC (1/100) (G,H), PTMC-PI-TMAC (1/50) (I,J) network films. In all PTMC network films, the ratio of PI/(TMC repeating unit in the polymer) was 1/1000. PTMC-PI network films contain only photoinitiator and no PTMC macromer.

Figure 26:
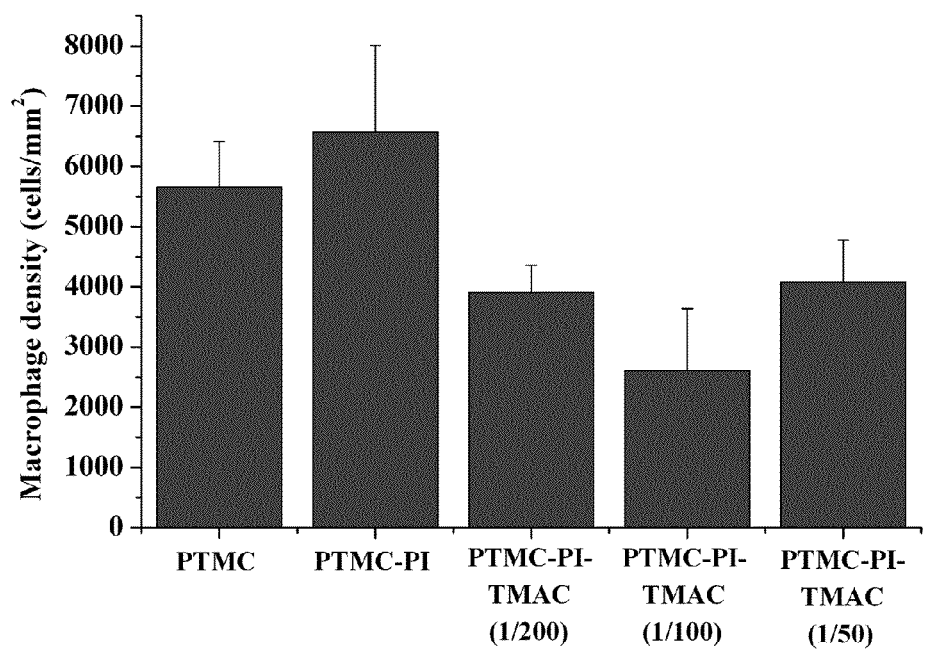

FIG. 26. Density of macrophages after 14 days of culturing on films prepared from linear PTMC, and photocross-linked (120 min) extracted network films having different ratios of methacrylate/(TMC repeating unit in the polymer). In all PTMC network films, the ratio of PI/(TMC repeating unit in the polymer) was 1/1000. PTMC-PI films contain only photoinitiator and no PTMC macromer.

EXAMPLES

Example 1

Materials

Polymer grade 1,3-trimethylene carbonate (TMC, Boehringer Ingelheim, Germany), and stannous octoate (Sigma, U.S.A.) were used as received. Pentaerythritol triacrylate (PETA, Aldrich, U.S.A.) was used as received. Solvents (Merck, Germany or Biosolve, The Netherlands) were of analytical grade.

Polymer Synthesis

Poly(1,3-trimethylene carbonate) (PTMC) homopolymers were synthesized by ring opening polymerization of the TMC monomer under vacuum at 130° C. for three days using stannous octoate as catalyst. To control molecular weight, different amounts of hexanediol were used as initiator. The polymers were purified by dissolution in chloroform and precipitation into ethanol, washing with fresh ethanol and drying at room temperature under vacuum.

Polymer Characterisation

Monomer conversion was determined by proton nuclear magnetic resonance ($^1$H-NMR) spectroscopy (300 MHz, Varian Innova, U.S.A.) using $CDCl_3$ (Merck, Germany).

Number average- and weight average molecular weights ($\overline{M}_n$ and $\overline{M}_w$, respectively), polydispersity indices (PDI) and intrinsic viscosities ([η]) of the purified polymers were determined by gel permeation chromatography (GPC, Viscotek U.S.A.). The setup was equipped with ViscoGEL I-guard-0478, ViscoGEL I-MBHMW-3078, and ViscoGEL I-MBLMW-3078 columns placed in series and a TDA 302 Triple Detector Array with refractometer-, viscometer-, and light scattering detectors, allowing the determination of absolute molecular weights. All determinations were performed at 30° C., using chloroform as the eluent at a flow rate of 1.0 ml/min.

Preparation of PTMC Films

Purified polymers were compression moulded at 140° C. using 500 μm thick stainless steel moulds using a laboratory press (Fonteijne THB008, The Netherlands). The films were moulded at approximately 25 kg/cm² and quenched to room temperature using cold water. To cross-link PTMC films in the presence of PETA, purified polymers and PETA (1 or 5 wt % of the polymer) were dissolved in dichloromethane to achieve good mixing. After evaporation of the solvent, compression moulded films were prepared in the same way as the purified polymers. These PETA-containing PTMC films were completely soluble in chloroform, confirming that no cross-linking had occurred under these conditions.

Gamma Irradiation, Network Formation and Network Characterization

The compression moulded films were sealed under vacuum in laminated polyethylene/polyamide bags (Revel Vacuum B.V., The Netherlands) and exposed to 25, 50 or 100 kGy gamma irradiation from a $^{60}$Co source (Isotron B.V., Ede, The Netherlands).

To determine equilibrium swelling ratios and gel contents, disk-shaped specimens (500 μm thick, 10 mm in diameter) were punched out from the irradiated films and placed in 30 mL $CHCl_3$ for 1 week, the solvent was refreshed once after 3 days. This procedure ensured complete removal of the sol fraction. Then the swollen gels were weighed, dried to constant weight at room temperature in vacuo and weighed again.

The gel and the sol fractions were calculated according to equations (1) and (2) respectively:

$$\text{Gel fraction (\%)} = \frac{m_d}{m_0} \times 100 \quad (1)$$

$$\text{Sol fraction (\%)} = \left(1 - \frac{m_d}{m_0}\right) \times 100 \quad (2)$$

where $m_d$ is the mass of dried (extracted) samples and $m_0$ is the mass of the specimens before swelling.

The swelling ratio (q) was calculated according to equation (3).

$$q = 1 + \rho_p \times \left(\frac{m_s}{m_d \times \rho_s} - \frac{1}{\rho_s}\right) \quad (3)$$

where $m_s$ is the mass of the extracted and swollen samples, and $\rho_s$ and $\rho_p$ are the densities of chloroform (1.48 g/cm³) and PTMC (1.31 g/cm³), respectively.

Thermal and Mechanical Properties

Glass transition temperatures ($T_g$) of the different PTMC films were determined by differential scanning calorimetry (DSC). The films containing 0 or 5 wt % PETA were irradiated at 0 or 25 kGy. $T_g$s of PETA containing irradiated films were also determined after extraction of the sol fraction using ethanol. Samples (5-10 mg) were analyzed at a heating rate of 10° C./min in a temperature range of −50 to 200° C. using a PerkinElmer Pyris 1 DSC. After the first scan, samples were quenched to −50° C. at 300° C./min and a second scan was recorded after 5 minutes. The reported values were determined from the second scan. Indium, lead, and cyclohexane were used as standards for temperature calibration of the instrument.

The mechanical properties of melt pressed and irradiated PTMC films were determined in triplicate according to ASTM-D 882-91. A Zwick 2020 tensile tester (Ulm, Germany) equipped with a 500 N load cell was operated at a crosshead speed of 50 mm/min. The initial grip-to-grip separation was 50 mm and a preload of 0.01 N was applied. The specimen deformation was derived from the grip-to-grip separation; therefore the presented values of Young's modulus (calculated from the initial slope of the stress-strain curves) give only an indication of the stiffness of the polymers.

To assess their behaviour under dynamic loading conditions, the specimens (n=1) were repetitively (20×) elongated to 50% strain at 50 mm/min in cyclic tests. After a 2 h recovery period, the permanent deformation was estimated from the stress-strain diagram of the $21^{st}$ cycle. In these experiments a preload of 0.01 N was applied, the deformation was derived from the grip to grip separation. The error in the values is approximately 0.5% strain.

The tear strength of films was determined according to ASTM 1938 using trouser shaped specimens (n=3). The dimensions of the specimens were 75×25×0.5 mm with a 50 mm long cut halfway through the width of the specimens. Measurements were performed in triplicate at a speed of 250 mm/min. The reported maximum tear strengths are normalized to the thickness of the specimens and expressed in N/mm. For comparison, the mechanical properties of silicone elastomer (Sylgard® 184, Dow Corning, U.S.A.) films were also determined as described above. Silicone elastomer films with a thickness of approximately 500 μm were cast and thermally cured according to the instructions of the manufacturer.

Cell Viability Assay

Possible cytotoxicity of the gamma irradiated and non-extracted PTMC films containing 5 wt % PETA was evaluated using a direct and an indirect MTS [3-(4,5-dimethylthiazol-2-yl)-5-(3-carboxymethoxyphenyl)-2-(4-sulfophenyl)-2H-tetrazolium] assay. Briefly, mouse skin fibroblasts (NIH 3T3 cell line) were cultured using a 96 wells plate (5000 cells/well) and Dulbecco's modified Eagle's medium (DMEM). The cells were incubated at 37° C. and 5% $CO_2$ for three days. For the indirect cytotoxicity evaluations, non-extracted disks (n=3, diameter 8 mm, thickness 500 μm) of each film were incubated at 37° C. and 5% $CO_2$ with 500 μl DMEM for 24 hours to extract any leachable components. After the three day period of cell culturing, the medium was replaced by the leachables-containing DMEM medium. In the direct cytotoxicity assays, non-extracted discs (n=3) were placed directly on the cells in culture. In both assays, the absorbance of formazan, which is soluble in the culture medium, was measured after another two days of culture. The mean value obtained for cell cultures incubated with DMEM medium only (negative control) was standardized as 100% cell viability. Latex rubber (Hilversum Rubber Factory, Hilversum, The Netherlands) was used as positive control.

In Vitro Enzymatic Erosion Studies

Cholesterol esterase (CE) from porcine pancreas was used to study the enzymatic hydrolysis of gamma irradiated PTMC films. Aqueous CE enzyme solutions were prepared at a concentration of 20 μg/mL using phosphate buffered saline (PBS, pH=7.4) containing 0.02 wt % $NaN_3$ (Sigma, U.S.A.) as a bactericide. Non-extracted, disk-shaped films (10 mm diameter, approximately 500 μm thickness, n=3 per time point) were placed in vials containing 1 ml of enzyme solution and conditioned at 37° C. The medium was refreshed once every two days. Control experiments without enzyme were performed using PBS (pH 7.4, n=1 per time point). At predetermined time points, the mass and thickness of wet specimens were determined after rinsing and blotting their surfaces. The measurements were performed again after drying the specimens to constant weight in vacuo at room temperature.

Results

The effect of initial polymer molecular weight and pentaerythritol triacrylate content on gamma irradiation cross-linking behaviour and on the physical properties of the resulting PTMC networks was evaluated. By varying the initiator concentration from 0 to 0.1 mol %, PTMC polymers having molecular weights in the range of 80-450 kg/mol were synthesized (See table 1, the molecular weight is given in indices for each polymer). Monomer conversions were higher than 99% in all cases. The molecular weights of the obtained polymers were lower than could be expected from the monomer to initiator ratios assuming each hydroxyl group initiates a growing polymer chain. This is probably due to initiation of the polymerisation from hydroxyl group containing impurities such as water. After compression moulding, slightly lower $\overline{M}_n$ values and higher polydispersity indices were obtained.

TABLE 1

Characteristics of the synthesized PTMC homopolymers before and after compression moulding. The values for compression moulded polymers are given between brackets.

| Polymer | Initiator content (mol %) | $\overline{M}_n{}^a$ (kg/mol) | $\overline{M}_w{}^a$ (kg/mol) | $PDI^a$ | $[\eta]^a$ (dl/g) |
|---|---|---|---|---|---|
| $PTMC_{88}$ | 0.1 | 88 (79) | 139 (143) | 1.58 (1.81) | 1.7 (1.8) |
| $PTMC_{157}$ | 0.05 | 157 (144) | 228 (217) | 1.45 (1.51) | 2.6 (2.6) |
| $PTMC_{277}$ | 0.025 | 277 (230) | 407 (382) | 1.47 (1.66) | 4.4 (4.3) |
| $PTMC_{443}$ | 0 | 443 (436) | 620 (698) | 1.48 (1.60) | 6.6 (7.1) |

$^a$Determined by GPC at 30° C. using chloroform as the eluent

Cross-Linking of PTMC by Gamma Irradiation

Compression moulded PTMC films having different molecular weights were gamma irradiated under vacuum at doses of 25, 50 or 100 kGy. Gel contents and equilibrium swelling ratios in chloroform are given in FIGS. 1A and 1B. The figures show that at a given irradiation dose, networks with higher gel contents and lower swelling ratios are obtained with increasing initial PTMC molecular weight. At 25 kGy, $PTMC_{88}$ and $PTMC_{157}$ did not cross-link at all, whereas $PTMC_{277}$ and $PTMC_{443}$ had relatively low gel contents of 22±1 and 60±1%, respectively. For the range of polymer molecular weights investigated the gel contents varied between 15±4% and 73±1%, with swelling ratios varying between 327±32 and 22±1 at an irradiation dose of 100 kGy.

In FIGS. 1A and 1B, it can also be seen that for a given molecular weight gel contents increased and swelling ratios decreased with increasing irradiation doses. Increasing the irradiation dose had a larger effect on PTMC of the lower molecular weights. For instance, increasing the dose from 25 to 100 kGy during irradiation of $PTMC_{443}$ increased the gel content from 60±1 to 73±1%, whereas the gel content increased from 0 to 42±2% for $PTMC_{157}$. At the same time swelling ratios decreased from 45±1 to 22±1 for $PTMC_{443}$ and from 537±9 (50 kGy) to 92±4 for $PTMC_{157}$. It can be concluded that the gel content and density of PTMC networks can be increased either by increasing the initial molecular weight of the polymer or by increasing the gamma irradiation dose.

The cross-linking behaviour of PTMC polymers of different initial molecular weights was evaluated according to Equation 4 which relates to the irradiation dose (r) to the sol fraction (s) of the formed network assuming that both chain scission and cross-linking events occur at random and that their number is proportional to the irradiation dose:

$$s + \sqrt{s} = \frac{G(s)}{2G(x)} + \frac{1}{2.08 \times 10^{-6} \times G(x) \times \overline{M}_n \times r} \quad (4)$$

where G(s) and G(x) are the radiation chemical yields of scission and cross-linking, respectively, and are defined as the number of scission and cross-linking events per 100 eV. As each cross-link involves two chains, the ratio of chain scission density to cross-link density is G(s)/2G(x) For polymers with random, monomodal molecular weight distributions, a linear relationship between $s+\sqrt{s}$ and the reciprocal of the irradiation dose is obtained. In FIG. 2A, such plots are given for the PTMC polymers used in this study. Extrapolation of $s+\sqrt{s}$ to infinite irradiation dose, allows determination of the ratios of the radiation chemical yield of scission to cross-linking given in equation 4. The ratios G(s)/G(x) determined for $PTMC_{443}$, $PTMC_{277}$, and $PTMC_{157}$ are 2.1, 2.0, and 1.4, respectively.

Extrapolation of the plots to zero gel contents (s+√s=2), the minimum gelation dose can be estimated. The minimum gelation doses for PTMC$_{443}$, PTMC$_{277}$ and PTMC$_{187}$ were determined to be 6.3, 16.7 and 36.3 kGy, respectively. The maximum gel fraction ((1-s)$_{max}$) that can be obtained, can be determined using the expression:

$$(1-s)_{max} = \frac{1}{2} \times \left[1 - \frac{G(s)}{G(x)} + \left(1 + \frac{2G(s)}{G(x)}\right)^{1/2}\right] \quad (5)$$

In FIG. 2B, it can be clearly seen that the G(s)/G(x) ratio decreased, whereas (1-s)$_{max}$ increased with increasing initial molecular weight of the PTMC polymers. The polymer with the highest molecular weight, PTMC$_{443}$, had the lowest ratio of chain scission to cross-linking (1.4) and the highest obtainable gel content (77%).

The nature of radicals formed by irradiation of polyethylene and linear aliphatic polyesters has been investigated by electron spin resonance (ESR). For polyethylene, alkyl radicals formed upon hydrogen abstraction can combine to form a crosslink although main chain scission can also occur. Therefore, irradiation can simultaneously lead to the formation of polymer networks, branched structures and polymer chains of lower molecular weight. Alkyl radicals are also formed upon irradiation of poly(ε-caprolactone) and poly(glycolide). However, the observed formation of gaseous products (carbon monoxide, carbon dioxide and hydrogen) suggests that C-O bonds are also broken upon irradiation. When irradiating PTMC$_{88}$ and PTMC$_{157}$ at 25 kGy, respective $\overline{M}_n$ values decreased to 45 and 127 kg/mol, while $\overline{M}_w$ values increased to 173 and 394 kg/mol. The respective polydispersity indices (PDI) increased from 1.81 and 1.51 to 3.84 and 3.10, which indicate the formation of branched PTMC structures. Upon irradiation at 50 kGy, the PDI value of PTMC$_{88}$ increased even further to 6.99.

Cross-Linking of PTMC by Gamma Irradiation in the Presence of Pentaerytritol Triacrylate (PETA)

PTMC cross-links upon gamma irradiation, but to reach high gel contents polymers of very high molecular weight are required. In case of the highest molecular weight PTMC polymer we synthesized (443 kg/mol), gamma irradiation at 100 kGy resulted in a network with a gel content of 73%.

Theoretically, estimations show that a maximum gel percentage of 77% can be expected (FIGS. 1A, 2B and Equation 5).

In general, the gel percentage of networks formed can be increased by irradiation in the presence of cross-linking reagent that reduced the ratio of chain scission to cross-linking events. To enhance network formation of PTMC upon gamma irradiation, PETA was used as a cross-linking reagent. By itself, PETA yielded gel percentages of 99.8±0.1% upon gamma irradiation at 25 kGy.

FIGS. 3A and 3B show the gel contents and the equilibrium swelling ratios of networks prepared by gamma-irradiating PTMC of different initial molecular weights containing different amounts of PETA (0, 1, 5 wt %) at 25 kGy. The effect of the incorporation of PETA can clearly be seen: The resulting PTMC networks had greatly increased gel contents and decreased swelling ratios. The effect was most pronounced when PETA was added to PTMC of relatively lower molecular weight. For PTMC$_{88}$ that contained 0, 1, and 5 wt % PETA, the gel content of the networks after irradiation at 25 kGy increased from 0% to 31±1% and 73±1%, respectively. For PTMC$_{443}$ the respective values were 60±1%, 76±1%, and 96±1%. Incorporation of PETA also resulted in more densely cross-linked PTMC networks. After irradiating PTMC$_{443}$ at 25 kGy, the swelling ratios of networks were respectively 45±1, 22±1, and 4.6±0.2 for films that contained 0, 1, and 5 wt % PETA.

For the range of PTMC polymer molecular weights investigated, the gel contents of networks formed upon irradiation at 25 kGy ranged from 31±1 to 76±1% and from 73±1 to 96±1% for films that contained 1 and 5% PETA respectively. The corresponding swelling ratios in chloroform ranged from 75±1 to 22±1 and from 7.1±0.1 to 4.6±0.2. This shows that by incorporating PETA, the extent of PTMC cross-linking by gamma irradiation was greatly enhanced. The gel content and network density of the networks could readily be varied by adjusting the PETA content.

Irradiating PTMC films containing 5 wt % PETA at higher irradiation doses of 50 or 100 kGy, led to lower gel contents of the formed networks. The gel content of networks formed using PTMC$_{443}$ decreased from 96% to 87% upon increasing the irradiation dose from 25 kGy to 100 kGy. It is likely that already at 25 kGy all PETA had been consumed and no further enhancement of the cross-linking efficiency can be expected. Indeed, NMR spectra of extracts of PETA-containing gamma irradiated PTMC films did not reveal the presence of compounds containing unreacted show acrylate groups.

The swelling ratios of the different PTMC networks prepared by gamma irradiation in the presence of 5 wt % PETA ranged from 4.6 to 7.1. These values are comparable to those of the previously mentioned photocross-linked networks prepared from three-armed PTMC macromers with molecular weights of 1500 and 17200 g/mol, which had swelling ratios of 3.3±0.4 and 9.8±0.4, respectively. As a crude approximation, the molecular weight between cross-links of networks prepared by irradiating PTMC in the presence of 5 wt % PETA can be expected to range from approximately 1500 to 3600 g/mol.

Thermal and Mechanical Properties of Gamma Irradiated PTMC Networks

All PTMC polymers were amorphous with glass transition temperatures (T$_g$) below room temperature. The T$_g$s of compression moulded, non-irradiated PTMC films were independent of polymer molecular weight and varied from −17.7 to −18.5° C. When PETA was not added to the polymer, gamma irradiation at 25 kGy did not have a significant effect on the T$_g$s of the films. Incorporation of 5 wt % PETA did increase the glass transition temperature of gamma irradiated PTMC films. This could be due to denser network formation. Before extraction, the T$_g$ values of these films were between −16.2 and −16.7° C., while the values were somewhat higher (−14.7 to 15.1° C.) after extraction with ethanol. Thermal analysis of the films only showed a single T$_g$ in the investigated temperature range (−50 to 200° C.), indicating that PETA was homogeneously incorporated into the PTMC networks.

The effect of initial molecular weight and network formation on elastic modulus (E-modulus), yield strength and stress at break values of PTMC films are given in FIGS. 4A, 4B and 8C, while representative stress-strain curves of PTMC$_{88}$ and PTMC$_{443}$ are given in FIGS. 5A and 5B, respectively. In the non-cross-linked state, E-modulus, yield strength and stress at break values increased with increasing polymer molecular weight. All PTMC films were flexible; E-modulus and yield strength values for PTMC$_{88}$ were 6.3±0.2 and 1.2±0.1 MPa, respectively, whereas for PTMC$_{443}$ these values were 7.2±0.1 and 2.8 MPa, respectively (FIGS. 4A and 4B). The stress at break increased from 0.7±0.1 MPa for PTMC$_{88}$ to 25.2±3.7 MPa for PTMC$_{443}$. This dependence of mechanical properties on molecular weight of PTMC has been observed before. Upon gamma-cross-linking the different PTMC films at 25 kGy, the E-modulus and yield strength values decreased to values ranging from 5.5±0.1 to 6.7±0.2 MPa and 0.9±0.1 to 2.0±0.1 MPa, respectively (FIGS. 4A and 4B). Similarly, the stress at break of these non-extracted networks were lower (values ranging from 0.7±0.1 to 14±0.4 MPa) than those of non-cross-linked films (FIG. 4C and also FIG. 5A, 5B). These values are close to those of silicone elastomer films which had an E-modulus of 2.6±0.2 MPa and a stress at break tensile strength 7.3±0.5 MPa.

Increasing the irradiation dose, further decreased the E-modulus and yield strength of the PTMC films. At 100 kGy, the E-modulus and yield strength of the films ranged from 2.9±0.2 to 4.6±0.2 MPa and from 0.5 to 1.2 MPa, respectively. The stress at break values were also lower ranging from 0.5±0.1 to 2.7±0.2 MPa. Although increasing the irradiation dose yields higher gel content and network density, it also leads to lower strength and stiffness. This is likely due to the chain scission that simultaneously occurs with cross-linking during gamma-irradiation.

By incorporating PETA into the network structure, the decrease in E-modulus and stress at break can be prevented. In FIGS. 4 and 5 it can also be seen that all gamma irradiated (non-extracted) PTMC networks containing 5 wt % PETA were still very flexible and rubber-like. The E-modulus and yield strength values ranged from 9.5±0.6 to 10.7±0.2 MPa (FIG. 4A) and from 3.1±0.1 to 4.9±0.1 (FIG. 4B), respectively. Large increases in the stress at break of PTMC networks were observed upon irradiation in the presence of PETA. The stress at break of $PTMC_{157}$ increased very significantly from 1.4±0.1 MPa to 25.0±1.8 MPa upon irradiation at 25 kGy in the presence of 5 wt % PETA (FIG. 4C). Films of $PTMC_{443}$ gamma irradiated in the presence of 5 wt % PETA had an exceptionally high maximum tensile strength of 35.3±0.3 MPa. This allows its utilization in applications where high strengths are required, such as in the tissue engineering of ligaments. Extraction of the sol fraction of PTMC networks prepared in the presence of 5 wt % PETA with ethanol further improved the maximum tensile strength. The stress at break of $PTMC_{88}$ increased from 5.5±0.9 to 12.4±2.9 MPa (FIGS. 4C and 5A) and that of $PTMC_{443}$ to 37.7±1.3 MPa (FIGS. 4C and 5B). The E-modulus and yield strength values of extracted networks were comparable to those of non-extracted ones. The creep resistance of PTMC films was evaluated in cyclic deformation experiments, as described in the experimental part. FIG. 4D shows that the permanent set of non-cross-linked PTMC films is mainly determined by the polymer molecular weight and varied from 11.2% to 1.2%. The highest molecular weight polymers are the most resistant to creep. Gamma irradiation at 25 kGy lowered the permanent set of all polymers. Irradiated non-extracted films of $PTMC_{443}$, and $PTMC_{277}$ had permanent set values which were the same as of silicone rubber (1.0% strain), showing the excellent creep resistance of these biodegradable elastomers. When $PTMC_{88}$ was irradiated at 25 kGy, the non-extracted films also had a much lower permanent set (3.2%) than that of non-irradiated films (11.2%), even though no gel formation was observed. Upon gamma irradiation at 25 kGy in the presence of 5 wt % PETA, the permanent set values of non-extracted $PTMC_{88}$ and $PTMC_{157}$ further decreased to 1.4 and 1.6% strain, respectively. This implies that even in the case of PTMC polymers of relatively low initial molecular weights, networks with excellent creep resistance can be obtained by gamma irradiation. Upon extraction with ethanol, the permanent set of all PETA-containing networks was even lower (0.9-1.2%).

The effect of gamma irradiation on the tear propagation resistance of $PTMC_{443}$ was evaluated. Non-irradiated $PTMC_{443}$ films had a maximum tear strength of 1.9±0.2 N/mm, already this value was much higher than that of silicone elastomer films (0.21±0.01 N/mm). Upon gamma irradiation in the presence of 5 wt % PETA, the tear resistance of the PTMC networks significantly increased to values of 4.2±0.2 N/mm. After extraction with ethanol, the tear strength increased even further to 9.3±2.0 N/mm.

Viability of Cells in Contact with Gamma Irradiated PTMC Networks

Possible cytotoxicity of (non-extracted) PTMC films gamma irradiated at 25 kGy was assessed in the presence of 5 wt % PETA by direct and an indirect cell viability assay (FIG. 6). In both assays, no adverse effect on the morphology of the cells was observed. When fibroblasts were in direct contact with the films, cell viability values were very high with values ranging from 87±16 to 117±26%. Also in the indirect assay, cell viabilities were very high with values ranging from 91±8 to 100±7%. It is therefore confirmed that cross-linking in the presence of 5 wt % PETA did not have an adverse effect on cell viability.

In vitro Enzymatic Erosion of Gamma Irradiated PTMC Networks

The in vitro enzymatic erosion of non-extracted $PTMC_{443}$ films irradiated at 25 kGy was investigated using cholesterol esterase (CE), as this enzyme probably plays an important role in the erosion of PTMC. FIGS. 7A, 7B and 7C show the changes in mass and thickness of films incubated in aqueous CE solutions as a function of time. Irradiated PTMC films containing 5 wt % PETA eroded much slower than those that did not contain PETA. After three weeks the mass loss of films that did not contain PETA was approximately 64%, whereas films containing 5% PETA had lost approximately 13% of their mass. The decrease in thickness of 5 wt % PETA containing films was also much lower than that of the films that did not contain PETA (FIG. 7B). The corresponding erosion rates in this enzyme solution were respectively 12.0±2.9 μm/day and 3.0±1.6 μm/day. For both polymer films, the decrease in mass occurred simultaneously with a decrease in thickness (FIG. 7C), which implies a surface erosion process. In FIG. 7C, the decrease in thickness seems to be somewhat lower than the decrease in mass, especially at the later time points. This can be the result of errors in determining the thickness of the films due to roughening of the surface during degradation.

These results show that cross-linking of PTMC in the presence of PETA is an effective manner of reducing the erosion rate of PTMC networks. This can be due to the higher gel contents and network densities of $PTMC_{443}$ films containing PETA. Also the higher water uptake of PETA-containing PTMC networks, as a result of the hydroxyl group present in PETA, can play a role. After 21 days of incubation in aqueous CE solutions, the water uptake of the PETA containing-films was 3.4±0.6%, while $PTMC_{443}$ networks that did not contain PETA took up 1.7±0.4% water. It is known that this enzyme is most activated upon adsorption to hydrophobic substrates.

Conclusion

Flexible PTMC networks with high gel contents and high network densities can be obtained by gamma irradiation of compression moulded PTMC films in the presence of pentaerythritol triacrylate (PETA). The incorporation of this cross-linking reagent also leads to networks with high tensile strengths and excellent tear- and creep resistance. Moreover, the enzymatic erosion rates of PTMC networks can be decreased in this manner. Based on direct and indirect assays, these networks do not have any adverse effect on the viability of fibroblasts. It can therefore be concluded, that gamma irradiation in the presence of PETA is a very effective method to obtain biodegradable PTMC networks with elastomeric properties. These rubber-like biodegradable PTMC networks are well-suited for medical applications such as the engineering of soft- and cardiovascular tissues, and controlled release.

Example 2

Materials

Polymer grade 1,3-trimethylene carbonate (TMC, Boehringer Ingelheim, Germany), polymer grade D,L-lactide (DLLA, Purac Biochem, The Netherlands), stannous octoate (Sigma, U.S.A.), and pentaerythritol triacrylate (PETA, Aldrich, U.S.A.) were used as received. Solvents (Merck, Germany or Biosolve, The Netherlands) were of analytical grade. J774A macrophages (ATCC-TIB-67) were obtained from the American Type Culture Collection. Culture media, fetal bovine serum, Glutamax™ and penicillin-streptomycin were obtained from Invitrogen (Gibco, U.S.A.). Culture disposables were from Nunc (U.S.A.) and Greiner (Germany).

Polymer Synthesis

Poly(1,3-trimethylene carbonate), poly(D,L-lactide) homopolymers and copolymers of TMC with DLLA were synthesized by ring opening polymerization of the corresponding monomers (50, 60, and 70 mol % TMC) under vacuum at 130° C. for three days using stannous octoate as catalyst. The polymers were purified by dissolution in chloroform and precipitation into ethanol or isopropanol, washing with fresh alcohol and drying at room temperature under vacuum. co-polymers with DLLA were further dried at 80° C. under nitrogen until constant weight.

Polymer Characterisation

Monomer conversion and copolymer compositions were determined by proton nuclear magnetic resonance ($^1$H-NMR) spectroscopy (300 MHz, Varian Innova, U.S.A.) using CDCl$_3$ (Merck, Germany). Number average- and weight average molecular weights ($\overline{M}_n$ and $\overline{M}_w$, respectively), polydispersity indices (PDI) and intrinsic viscosities ([η]) of the co-polymers were determined by gel permeation chromatography (GPC, Viscotek U.S.A.). The setup was equipped with ViscoGEL I-guard-0478, ViscoGEL I-MBHMW-3078, and ViscoGEL I-MBLMW-3078 columns placed in series and a TDA 302 Triple Detector Array with refractometer-, viscometer-, and light scattering detectors, allowing the determination of absolute molecular weights. All determinations were performed at 30° C., using chloroform as the eluent at a flow rate of 1.0 ml/min.

Preparation of Polymer Films

Purified polymers were compression moulded at 140° C. in 500 micrometer thick stainless steel moulds using a laboratory press (Fonteijne THB008, The Netherlands). The films were moulded at approximately 25 kg/cm$^2$ and quenched to room temperature using cold water. For the cross-linking experiments of polymer films containing PETA (see below), purified polymers and PETA (5 wt % of the polymer) were dissolved in dichloromethane to achieve homogeneous mixing. After evaporation of the solvent compression moulded films were prepared in the same way as the purified polymers.

Gamma Irradiation, Network Formation and Network Characterization

The compression moulded films were sealed under vacuum in laminated polyethylene/polyamide bags (Revel Vacuum B.V., The Netherlands) and exposed to 25 kGy gamma irradiation from a $^{60}$Co source (Isotron B.V., Ede, The Netherlands). To determine equilibrium swelling ratios and gel contents, disk-shaped specimens (500 μm thick, 10 mm in diameter) were punched out from the irradiated films and placed in 30 mL CHCl$_3$ for 1 week, the solvent was refreshed once after 3 days. This procedure ensured complete removal of the sol fraction. Then the swollen gels were weighed, dried to constant weight at room temperature in vacuo and weighed again. The gel and the sol fractions were calculated according to equations (1) and (2) respectively:

$$\text{Gel fraction (\%)} = \frac{m_d}{m_0} \times 100 \quad (1)$$

$$\text{Sol fraction (\%)} = \left(1 - \frac{m_d}{m_0}\right) \times 100 \quad (2)$$

where $m_d$ is the mass of dried (extracted) samples and $m_0$ is the mass of the specimens before swelling. The volume degree of swelling (q) was calculated according to equation (3):

$$q = 1 + \rho_p \times \left(\frac{m_s}{m_d \times \rho_s} - \frac{1}{\rho_s}\right) \quad (3)$$

where $m_s$ is the mass of the extracted and swollen samples and $\rho_s$ and $\rho_p$ are the densities of chloroform (1.4832 g/cm$^3$) and the co-polymers respectively. The densities of the copolymers were determined by measuring the mass and dimensions of compression moulded films. The densities of TMC and DLLA copolymers containing 100%, 72%, 60%, 48%, and 0% TMC were 1.31, 1.29, 1.27, 1.26, and 1.25 g/cm$^3$, respectively.

Thermal and Mechanical Properties

The mechanical properties of melt pressed and irradiated (0 kGy, 25 kGy) co-polymers containing PETA (0 wt %, 5 wt %) were determined in triplicate according to ASTM-D 882-91. The measurements were performed on extracted as well as on non-extracted specimens that measured 0.5×10×0.05 cm$^3$. Extraction of the leachable components was performed with ethanol. A Zwick 2020 tensile tester (Ulm, Germany) equipped with a 500 N load cell was operated at a crosshead speed of 500 mm/min. The initial grip to grip separation was 50 mm and a preload of 0.01 N was applied. The specimen deformation was derived from the grip-to-grip separation; therefore, the presented values of elastic modulus (calculated from the initial slope of the stress-strain curves) give an indication of the stiffness of the polymers. The tear strength of films was determined according to ASTM 1938 using trouser shaped specimens (n=3). The dimensions of the specimens were 75×25×0.5 mm with a 50 mm long cut halfway through the width of the specimens. Measurements were performed in triplicate at a speed of 250 mm/min. The reported maximum tear strengths are normalized to the thickness of the specimens and expressed in N/mm. Glass transition temperatures ($T_g$) and melting temperatures of purified polymers and irradiated polymer films were determined by differential scanning calorimetry (DSC). Samples (5-10 mg) were analyzed at a heating rate of 10° C./min in a temperature range of −100 to 200° C. using a PerkinElmer Pyris 1 DSC. After the first scan, samples were quenched to −100° C. at 300° C./min and a second scan was recorded after 5 minutes. The reported values were determined from the second heating scan. Indium, lead, and cyclohexane were used as standards for temperature calibration.

Cell Viability Assay

Possible cytotoxicities of gamma irradiated, non-extracted co-polymer films containing 5 wt % PETA were evaluated using a direct and an indirect MTS [3-(4,5-dimethylthiazol-2-yl)-5-(3-carboxymethoxyphenyl)-2-(4-sulfophenyl)-2H-tetrazolium] assay. Briefly, mouse skin fibroblasts (NIH 3T3 cell line) were cultured using a 96 wells plate (5000 cells/well) and Dulbecco's modified Eagle's medium (DMEM). The cells were incubated at 37° C. and 5% $CO_2$ for three days.

For indirect cytotoxicity evaluations, non-extracted disks (n=3, diameter 8 mm, thickness 500 μm) of each film were incubated at 37° C. and 5% $CO_2$ with 500 μl DMEM for 24 hours to extract any leachable components. After the three day period of cell culturing, the medium was replaced by the leachables-containing DMEM medium. In the direct cytotoxicity assays, non-extracted discs (n=3) were placed directly on the cells in culture. In both assays, the absorbance of formazan, which is soluble in the culture medium, was measured after another two days of culture. The mean value obtained for cell cultures incubated with DMEM medium only (negative control) was standardized as 100% cell viability. Latex rubber (Hilversum Rubber Factory, Hilversum, The Netherlands) was used as positive cytotoxic control.

Macrophage-Mediated Erosion Studies

J774A macrophages were maintained in DMEM containing 4.5 g/L D-glucose, pyruvate, 10% fetal bovine serum, 100 U/mL penicillin, 100 μg/mL streptomycin and 100 μg/mL 2 mM Glutamax™. Cells were passaged every 4 to 7 days by scraping.

Macrophage-mediated erosion of non-irradiated co-polymer films that did not contain PETA as well as gamma irradiated, non-extracted co-polymer films that contained 5 wt % PETA was investigated by directly culturing J774A macrophages on the surfaces of the films. The test specimens were 15 mm in diameter and approximately 500 μm in thickness. The seeding density was approximately $8 \times 10^4$ cells/$cm^2$. Fresh aliquots of cells were added to each well at days 7 and 10. Medium was exchanged three times a week. Cells were cultured on six disks of each material.

After 14 days of culturing, three specimens of each material were first placed in Milli-Q water to lyse the cells, and then thoroughly rinsed and weighed. After drying the films to constant weight in vacuo at room temperature, the samples were weighed again. The surfaces of the specimens were sputter-coated with gold and then analysed by scanning electron microscopy (SEM, Philips XL 30 ESEM-FEG, The Netherlands) at an operating voltage of 5 kV.

The remaining disks of each material (n=3) were fixed with 3.7% para-formaldehyde in cytoskeletal stabilizing (CS) buffer (0.1 M piperazine-1,4-bis(2-ethanesulfonic acid) (PIPES) buffer, 1 mM ethylene glycol tetraacetic acid (EGTA), pH=6.9) for 15 min and then transferred to PBS. The specimens were used for fluorescence staining of cell nuclei using 4',6-diamidino-2-phenylindole (DAPI) and of the actin cytoskeleton using tetramethylrhodamine iso-thiocyanide-phalloidin (TRITC-phalloidin). These specimens were then analysed by confocal laser scanning microscopy (LEICA TCS SP2, with a fully water-immersed 40× objective (NA 0.80)).

Results

High molecular weight copolymers of trimethylene carbonate (TMC) and D,L-lactide (DLLA), and PTMC and PDLLA homopolymers were synthesized by ring opening polymerization. The conversion of monomers was higher than 95%, and (co)-polymers having monomer compositions close to the charged compositions were obtained after purification by precipitation (Table 2). After compression moulding the molecular weights of the co-polymers remained very high, although the molecular weights of co-polymers with high DLLA contents had decreased somewhat upon compression moulding. Polymers with high molecular weights are desired, as it was shown that the efficiency of cross-linking by gamma irradiation increased with increasing polymer molecular weight. The synthesized TMC containing co-polymers are rubbery at physiological temperatures, as their glass transition temperatures ranged from −17.9 to 16.5° C.

TABLE 2

Characteristics of the synthesized and purified P(TMC-DLLA) co-polymers before- and after compression moulding. Values given between brackets are for compression moulded specimens.

| TMC content[a] (mol %) | DLLA content[a] (%) | $\overline{M}_n$[b] (kg/mol) | $\overline{M}_w$[b] (kg/mol) | PDI[b] | $[\eta]$[b] (dl/g) | $T_g$[c] (° C.) |
|---|---|---|---|---|---|---|
| 100 | 0 | 443 | 620 | 1.5 | 6.6 | −17.9 |
|  |  | (436) | (698) | (1.6) | (7.1) |  |
| 72 | 28 | 399 | 624 | 1.6 | 5.0 | 0.1 |
|  |  | (385) | (586) | (1.5) | (4.6) |  |
| 60 | 40 | 404 | 633 | 1.6 | 4.7 | 10.4 |
|  |  | (384) | (593) | (1.5) | (4.4) |  |
| 48 | 52 | 285 | 429 | 1.5 | 2.8 | 16.5 |
|  |  | (232) | (361) | (1.6) | (2.8) |  |
| 0 | 100 | 283 | 375 | 1.3 | 3.2 | 52.1 |
|  |  | (208) | (336) | (1.6) | (2.8) |  |

[a] Determined by $^1$H-NMR on specimens purified by precipitation
[b] Determined by GPC at 30° C. using chloroform as the eluent.
[c] Determined by DSC(second heating scan) using compression moulded films.

Cross-Linking of P(TMC-DLLA) Co-Polymers by Gamma Irradiation

The cross-linking behaviour of compression moulded co-polymer films by gamma irradiation under vacuum was first investigated in the absence of PETA. The gel contents and swelling ratios of the resulting co-polymer networks are given in FIG. 8. Upon irradiation at 25 kGy, the 48% TMC-containing copolymer and PDLLA did not cross-link. This is in agreement with the previous studies. In the case of PDLLA, $\overline{M}_n$, $\overline{M}_w$, values had decreased to 78 kg/mol, 117 kg/mol, respectively, whereas for the copolymer the respective values were 60 kg/mol, 111 kg/mol. The copolymers with higher TMC contents (60% and 72%) could be cross-linked by gamma irradiation to yield networks with 12±2%, and 30±1% gel contents. The very high swelling ratios in chloroform indicate the low cross-link densities of these copolymer networks. Gamma irradiated PTMC films had the highest gel content of 60±1%.

FIG. 8 also clearly shows that incorporation of a small amount of PETA into the co-polymer films significantly increased the gel percentage of the formed networks, likely by increasing the ratio of cross-linking- to chain scission events that occur during the gamma irradiation process. At 25 kGy, transparent and form-stable co-polymer networks with high gel contents ranging from 86±5 to 96±1% were obtained. Interestingly, even PDLLA could be cross-linked efficiently during gamma irradiation by using PETA as a cross-linking agent. The formed networks were densely cross-linked with swelling ratios in chloroform ranging from 4.6±0.2 to 11.0±2.5 vol/vol. This indicates the possibility of sterilizing these co-polymers by gamma irradiation without significant chain scission and loss in mechanical properties.

In these experiments, PETA was homogeneously mixed and with the co-polymers in solution. This allowed us to obtain very high gel contents with a multi-acrylate cross-linking agent. The potential of PETA as a cross-linking reagent in the network formation was also investigated using co-polymers of TMC and ε-caprolactone (five co-polymers with ε-caprolactone contents of 41 to 100 mol %, all having $\overline{M}_n$ values above 200 kg/mol). PETA was also very effective in cross-linking these co-polymers: At 25 kGy, networks with gel contents ranging from 88 to 93% and swelling ratios ranging from 5.4 to 7.0 vol/vol were obtained with PETA contents of 5 wt %. This shows that this enhanced cross-linking method can be applied to other resorbable polymers as well.

Thermal- and Mechanical Properties of Gamma Irradiated P(TMC-DLLA) Co-Polymer Networks In the noncross-linked state, all P(TMC-DLLA) co-polymers were amorphous materials with glass transition temperatures ($T_g$) ranging from −17.9 to 52.1° C. (Table 3). The $T_g$ values decreased with increasing TMC content and could readily be tuned by adjusting the copolymer composition. Gamma irradiation in the absence of PETA seemed to lower $T_g$ values slightly, probably due to formation of relatively short chains by chain scission events. Upon irradiation in the presence of PETA, $T_g$ values increased owing to formation of a dense network compare FIG. 8B). The glass transition temperatures further increased upon removal of low molecular weight leachables from the networks using ethanol, and range from 14.9 to 53.7° C. The PETA-containing networks showed a single $T_g$, indicating that the co-polymers were homogeneously incorporated into the PETA network.

Table 3 also gives an overview of the tensile properties of P(TMC-DLLA) co-polymers and networks. It can be seen that by adjusting the copolymer composition, nonirradited films having elastic modulus values ranging from 5.1±0.1 to 2780±112 MPa can be obtained. Upon gamma irradiation in the absence of PETA, the elastic modulus and stress at break values of the co-polymer films decreased somewhat due to chain scission. The deterioration the mechanical properties of the co-polymers during gamma irradiation could be prevented by irradiating in the presence of PETA. Network films with higher elastic modulus, yield strength, and stress at break values are obtained, probably due to the prevention of chain scission and dense network formation. For the same reasons, the elongation at break values and yield strain values were lower for PETA-containing networks than for irradiated films that did not contain PETA. In tensile tests, the cross-linked specimens returned essentially to their original dimensions. Considering their glass transition temperatures to be below physiological temperatures the TMC containing networks might be useful in minimally invasive surgery where use of materials with shape memory is advantageous.

Removal of the low molecular weight compounds that might have formed during gamma irradiation by extraction with ethanol, further increased the elastic modulus and stress at break values of the network films. While retaining their high tensile strength, the elastic modulus values of PETA-containing gamma irradiated films were also found to depend on the copolymer composition. This indicates that the mechanical properties of these co-polymer networks can be tailored to suit any intended application.

An important characteristic of the network films is their resistance to tearing, as sutured polymeric biomaterials usually experience dynamic environments in vivo. The determined maximum tear strength of linear PTMC films was 1.9±0.2 N/mm. By gamma irradiation in the presence of PETA and by increasing the DLLA content of the copolymers, the tear propagation resistance of the formed networks could significantly be improved. The tear strengths of PETA-containing networks prepared from 100, 72, 60, and 48% TMC containing co-polymers were respectively 4.2±0.2, 10.6±1.0, 13.7±1.2 and 38.9±6.4 N/mm.

TABLE 3

Thermal- and mechanical properties of P(TMC-DLLA) co-polymers before and after gamma irradiation in the absence or presence of PETA. Values are expressed as mean ± standard deviation, (n = 3).

| TMC content (mol %) | Irradiation dose (kGy) | PETA content (wt %) | $T_g$ (° C.) | E (MPa) | $\sigma_{yield}$ (MPa) | $\epsilon_{yield}$ (%) | $\sigma_{break}$ (MPa) | $\epsilon_{break}$ (%) |
|---|---|---|---|---|---|---|---|---|
| 100 | 0 | 0.0 | −17.9 | 7.2 ± 0.1 | 2.8 ± 0.1 | 180 ± 20 | 25.2 ± 3.7 | 974 ± 45 |
| 100 | 25 | 0.0 | −18.1 | 6.7 ± 0.2 | 2.0 ± 0.1 | 190 ± 15 | 14.0 ± 0.4 | 1330 ± 40 |
| 100 | 25 | 5.0 | −16.4 | 10.7 ± 0.2 | 4.9 ± 0.1[a] | 110 ± 10[a] | 35.3 ± 0.3 | 580 ± 30 |
| 100[b] | 25 | 5.0 | −14.9 | 10.8 ± 0.3 | 4.9 ± 0.1[a] | 120 ± 15[a] | 37.7 ± 1.3 | 570 ± 15 |
| 72 | 0 | 0.0 | 0.1 | 5.1 ± 0.1 | 1.9 ± 0.1 | 120 ± 15 | 5.5 ± 1.4 | 1323 ± 108 |
| 72 | 25 | 0.0 | −1.9 | 4.8 ± 0.4 | 1.5 ± 0.1 | 250 ± 25 | 1.5 ± 0.1 | 1330 ± 174 |
| 72 | 25 | 5.0 | 1.8 | 32.4 ± 0.5 | 2.1 ± 0.1[a] | 25 ± 10[a] | 12.5 ± 1.2 | 523 ± 18 |
| 72[b] | 25 | 5.0 | 3.2 | 35.6 ± 0.2 | 2.2 ± 0.1[a] | 25 ± 10[a] | 15.4 ± 0.8 | 588 ± 36 |
| 60 | 0 | 0.0 | 10.4 | 14.5 ± 1.1 | 2.0 ± 0.1 | 130 ± 15 | 21.8 ± 2.0 | 1047 ± 25 |
| 60 | 25 | 0.0 | 9.4 | 10.6 ± 1.0 | 1.8 ± 0.1[a] | 150 ± 10[a] | 19.7 ± 4.7 | 1384 ± 28 |
| 60 | 25 | 5.0 | 11.7 | 34.8 ± 2.8 | 2.5 ± 0.1[a] | 40 ± 10[a] | 20.2 ± 2.0 | 593 ± 36 |
| 60[b] | 25 | 5.0 | 13.1 | 40.2 ± 2.8 | 2.4 ± 0.1[a] | 40 ± 10[a] | 18.5 ± 1.3 | 535 ± 24 |
| 48 | 0 | 0.0 | 16.5 | 195 ± 17 | 2.0 ± 0.1 | 55 ± 15 | 13.4 ± 1.7 | 804 ± 100 |
| 48 | 25 | 0.0 | 13.8 | 61 ± 11 | 1.6 ± 0.3[a] | 100 ± 25[a] | 6.2 ± 1.6 | 733 ± 111 |
| 48 | 25 | 5.0 | 20.0 | 630 ± 120 | 5.8 ± 1.1 | 4.2 ± 2.7 | 18.8 ± 3.6 | 378 ± 111 |
| 48[b] | 25 | 5.0 | 21.9 | 936 ± 88 | 10.3 ± 1.2 | 3.6 ± 2.1 | 23.8 ± 2.6 | 419 ± 26 |
| 0 | 0 | 0.0 | 52.1 | 2780 ± 112 | 55.5 ± 1.1 | 2.6 ± 0.1 | 48.8 ± 1.6 | 5.5 ± 0.8 |
| 0 | 25 | 0.0 | 51.1 | 2610 ± 101 | 49.9 ± 1.4 | 2.4 ± 0.1 | 42.2 ± 1.3 | 5.9 ± 1.6 |
| 0 | 25 | 5.0 | 52.6 | 2860 ± 84 | 59.1 ± 1.5 | 2.6 ± 0.1 | 58.1 ± 2.2 | 2.7 ± 0.2 |
| 0[b] | 25 | 5.0 | 53.7 | 2970 ± 117 | 59.9 ± 2.7 | 2.5 ± 0.1 | 59.3 ± 2.2 | 2.6 ± 0.2 |

[a]Estimated from the intersection of tangents to stress-strain diagrams as a distinct yield point could not be observed.
[b]Measurements were performed on gamma irradiated specimens after extraction of leachable components with ethanol.

Compatibility of Gamma Irradiated Co-Polymer Network Films with Fibroblasts

The compatibility of PETA containing gamma irradiated non-extracted networks with fibroblasts was investigated using a direct and an indirect assay. FIG. 9 shows the percentage of viable fibroblasts when incubated with different co-polymer network films. For all co-polymer networks the percentage of viable fibroblasts was comparable to that obtained for negative controls (100±13.5%). The cell viabilities in the direct assay ranged from 88±18 to 108±1% whereas in indirect assay the values ranged from 90±5 to 102±10. The results of both assays confirmed that these PETA-containing networks are not cytotoxic. In addition, these results showed that the solvents used for purification and for mixing PETA could be effectively removed from the polymer matrix.

In Vitro Erosion of Co-Polymer Films and Networks in Macrophage Cultures

In vivo, macrophages play an important role in the tissue response to biomaterials and in their degradation by secreting numerous substances. Superoxide anion radicals that can be secreted by macrophages can degrade linear PDLLA and PTMC networks. Cholesterol esterase, a hydrolytic enzyme that is also secreted by macrophages, has been shown to erode PTMC networks and P(TMC-DLLA) copolymers as well. As an initial assessment of the effect of macrophages on their erosion behaviour in vivo and of their biocompatibility, macrophages were directly cultured on gamma irradiated and on non-irradiated co-polymer films. P(TMC-DLLA) co-polymers are biocompatible materials and induce a mild inflammatory response upon subcutaneous implantation in rats. During, 14 days of culturing, no adverse effects on viability of macrophages from the P(TMC-DLLA) co-polymer networks or from their degradation products were observed. In addition macrophages were not activated upon culturing on these surfaces. This suggests that PETA containing P(TMC-DLLA) networks are biocompatible materials. The effect of copolymer composition and of cross-linking was investigated in the presence of PETA on the macrophage-mediated erosion of the films. FIG. 10 shows the surfaces of co-polymer films after 14 days of macrophage culturing, the corresponding erosion rates are given in Table 4. It can be seen from FIG. 10 that all non-irradiated co-polymer films had eroded during macrophage culturing. With decreasing TMC content, the extent of surface erosion seemed to decrease, this observation can be corroborated with the mass loss and erosion rate values given in Table 4. The mass loss values in 14 days and the erosion rates ranged from 5.35±0.49 to 0% and from 276±23 to 0 µg/(cm$^2$×day), respectively. This shows that copolymers containing higher amounts of TMC are most prone to surface erosion by macrophage derived compounds. This could be due to the differences in chemical structure or due to their lower glass transition temperatures. Interestingly, even on PDLLA films signs of erosion were seen. Apparently, macrophage-derived compounds are able to degrade PDLLA to some extent. Although mass loss could not be detected, signs of erosion were not detected on the sides of the films that were not in contact with the cells.

TABLE 4

Effect of co-polymer composition on the surface erosion rates and mass loss of non-irradiated P(TMC-DLLA) co-polymer films and of P(TMC-DLLA) co-polymer films containing 5% PETA gamma irradiated at 25 kGy after 14 days of macrophage culture. Values are expressed as mean ± standard deviation (n = 3).

| TMC content (mol %) | DLLA content (mol %) | 0 kGy, 0% PETA | | 25 kGy, 5% PETA | |
|---|---|---|---|---|---|
| | | Erosion rate (µg/cm$^2$ × day) | Mass loss (wt %) | Erosion rate (µg/cm$^2$ × day) | Mass loss (wt %) |
| 100 | 0 | 276 ± 23 | 5.35 ± 0.49 | 31 ± 12 | 0.60 ± 0.20 |
| 72 | 28 | 74 ± 2 | 1.46 ± 0.04 | 13 ± 2 | 0.26 ± 0.04 |
| 60 | 40 | 14 ± 2 | 0.28 ± 0.05 | 12 ± 1 | 0.25 ± 0.01 |
| 48 | 52 | 18 ± 12 | 0.40 ± 0.26 | —[a] | —[a] |
| 0 | 100 | —[a] | —[a] | —[a] | —[a] |

[a]Mass loss could not be detected.

By irradiating co-polymer films that contained 5 wt % PETA, their erosion rates could be reduced to a large extent. For the films prepared from PTMC homopolymer, the erosion rate decreased from 276±23 to 31±12 µg/(cm$^2$×day) (Compare FIGS. 10A and 10B). This is probably due to the formation of a dense network. The erosion rate of gamma irradiated PTMC that did not contain PETA has a relatively low cross-link density (FIG. 10B) and showed erosion rates of 265±32 µg/(cm$^2$×day), this is comparable to the erosion rates of non-irradiated PTMC shown in Table 4. Also upon subcutaneous implantation in rats, in vivo erosion rates of gamma irradiated PTMC network films are comparable to those of non-irradiated linear PTMC. This indicates that macrophage culturing assay is a suitable model for initial assessment of the effect of structural variables on in vivo erosion of biomaterials. Erosion was also observed for copolymer network films containing 72% and 60% TMC (FIGS. 10D and 10F), while for 48% and 0% TMC-containing co-polymer networks no mass loss could be detected. Only few eroded spots were observed on these network films (FIGS. 10H and 10J).

The differences in erosion of different materials could also be related to the number of macrophages present on the surfaces of the films. Macrophage densities on non-irradiated and gamma irradiated P(TMC-DLLA) films can be seen in FIG. 11. The cell numbers were comparable for non-irradiated copolymer films ranging from 3537±137 to 4770±612 cells/mm$^2$, except for 72% TMC containing copolymer film which had higher number of cells (6010±405 cell/mm$^2$). This is reasonable as these co-polymers are hydrophobic materials with contact angles not differing much with composition. In the case of gamma irradiated networks, the values were very close ranging from 3317±815 to 42±215 cells/mm$^2$. Cell numbers were also not affected much by cross-linking (again with the exception of 72% TMC containing copolymer). These results indicate that structural effects (composition, glass transition temperature, cross-linking) are probably more influential in macrophage-mediated erosion of these materials. Copolymers of TMC and DLLA, and PDLLA homopolymers also degrade by non-enzymatic bulk hydrolysis, and the effect of copolymer composition on their degradation behaviour has been investigated previously. No non-enzymatic hydrolytic degradation experiments were performed on networks prepared by irradiating TMC and DLLA co-polymer films containing 5 wt % PETA, however other degradation experiments using have shown that onset of mass loss is postponed in the case of photocross-linked acrylate-functionalized DLLA oligomers compared to linear high molecular weight PDLLA.

Conclusion

Pentaerythritol triacrylate can be used as a crossslinking agent/reagent to efficiently cross-link P(TMC-DLLA) co-polymers by gamma irradiation. By adjusting the copolymer composition, the thermal- and mechanical properties of the networks can readily be tuned. In vitro assays showed that these PETA-containing co-polymer networks and their degradation products are compatible with cells. The macrophage-mediated erosion of the co-polymer films could significantly be reduced by increasing the DLLA contents of the co-polymers. Erosion was also much reduced by the cross-linking process. This cross-linking method can be used to minimize damage during sterilization of TMC and DLLA-based materials by gamma irradiation and it allows for the preparation of polymeric materials with widely tuneable properties.

Example 3

Materials

Polymer grade 1,3-trimethylene carbonate (TMC) (Boehringer Ingelheim, Germany) and the catalyst, stannous octoate (Sigma, U.S.A.), were used as received. 1,6-hexanediol (Aldrich, Germany) was used as initiator in the PTMC synthesis. Also commercially available α,ω-dihydroxy poly(ε-caprolactone) (PCL) (Aldrich, Germany) and poly(ethylene glycol) monomethoxy ether (mPEG) (Fluka, Germany) having number average molecular weights ($\overline{M}_n$) of 10000 g/mol and of 5800 g/mol, respectively, were used as initiators to synthesize TMC block copolymers. A PCL polymer (Aldrich, Germany) having a molecular weight of 46000 g/mol was used for cross-linking studies. Pentaerythritol triacrylate (PETA) (Aldrich, Germany) and Irgacure®-369 (2-Benzyl-2-dimethylamino-1-(4-morpholinophenyl)-butanone-1) (Ciba®, Switzerland) were used as the cross-linking agent and photoinitiator.

Cholesterol esterase (CE) from porcine pancreas (Sigma, U.K., 56.2 U/mg) was dissolved in phosphate buffered saline (PBS, pH=7.4, B. Braun Melsungen A.G., Germany) for the enzymatic erosion studies. Solvents (Merck, Germany or Biosolve, The Netherlands) were of analytical grade. For cell culturing, α-minimum essential proliferation medium (α-MEM, Gibco U.S.A.) was used. This medium contained fetal bovine serum (10%, Biowhitaker, Belgium), ascorbic acid-2-phosphate (0.2 mM, Sigma, U.S.A.), penicillin G (100 Units/ml, Invitrogen U.S.A.) and streptomycin (100 µg/ml, Invitrogen U.S.A.), L-glutamine (2 mM, Sigma, U.S.A.), and basic fibroblast growth factor (1 ng/mL, Instruchemie, The Netherlands).

Polymer Synthesis

Poly(1,3-trimethylene carbonate) (PTMC) homopolymers were synthesized by ring opening polymerization of the TMC monomer under vacuum at 130° C. for three days using stannous octoate as catalyst. To control molecular weight, varying amounts of hexanediol were used as initiator. Monomethoxy poly(ethylene glycol)-block-poly(trimethylene carbonate) (mPEG-PTMC) diblock copolymers and poly(trimethylene carbonate)-block-poly(ε-caprolactone)-block-poly(trimethylene carbonate) (PTMC-PCL-PTMC) triblock copolymers were also prepared by ring opening polymerization of TMC at 130° C. for three days. The mPEG and PCL initiators were dried under vacuum at 130° C. for 90 min. In both cases, the charged TMC contents were 60 mole %.

All polymers were purified by dissolution in chloroform and precipitation into ethanol or hexane, washing with fresh non-solvent and drying at room temperature under vacuum.

Polymer Characterisation

Residual monomer contents and compositions of the copolymers were determined by proton nuclear magnetic resonance ($^1$H-NMR) spectroscopy (300 MHz, Varian Innova, U.S.A.) using CDCl$_3$ (Merck, Germany).

Number average- and weight average molecular weights ($\overline{M}_n$ and $\overline{M}_w$, respectively), polydispersity indices (PDI) and intrinsic viscosities ([η]) of the PTMC homopolymers were determined by gel permeation chromatography (GPC, Viscotek U.S.A.) using chloroform as the eluent at a flow rate of 1.0 ml/min. The setup was equipped with ViscoGEL I-guard-0478, ViscoGEL I-MBHMW-3078, and ViscoGEL I-MBLMW-3078 columns placed in series and a TDA 302 Triple Detector Array with refractometer-, viscometer-, and light scattering detectors, allowing the determination of absolute molecular weights. Both GPC and NMR were used for the molecular weight determination of the PTMC-PCL-PTMC block copolymer, whereas the molecular weight of mPEG-PTMC was only determined using NMR.

Preparation of Polymer Films

Purified PTMC polymers were compression moulded at 140° C. using 500 µm thick stainless steel moulds (Fonteijne THB008 laboratory press, The Netherlands). The films were moulded at approximately 25 kg/cm$^2$ and quenched to room temperature using cold water.

Films of PTMC and PTMC blends with the block copolymers (at a 9:1 weight ratio) containing PETA (5 wt %) and Irgacure® 369 (0.025 wt %) were prepared by dissolving the components in DCM, casting the solutions in Petri dishes and drying. These steps were performed in the dark, and compression moulding was then done as described above.

Photocross-Linking and Network Characterization

Compression moulded films containing PETA and photoinitiator were vacuum sealed in laminated polyethylene/polyamide bags (Revel Vacuum B.V., The Netherlands) and exposed to short wave UV light (UltraLum cross-linking cabinet, U.S.A., wavelength 254 nm) at a distance of 7 cm. Both sides of the specimens were illuminated at room temperature, for different time periods. The light intensity at this distance was 10-14 mW/cm$^2$, the polyethylene/polyamide bags reduced the intensity to 5-7 mW/cm$^2$ as measured with an optical power meter (Newport 1916-C, U.S.A.).

The equilibrium swelling ratios and gel contents of the photocross-linked films were determined using chloroform.

Mechanical Properties

The tensile properties of melt pressed and photocross-linked PTMC-based networks films before and after extraction with ethanol were determined in triplicate according to ASTM-D 882-91. A Zwick 2020 tensile tester (Germany) equipped with a 500 N load cell was operated at a crosshead speed of 50 mm/min. The initial grip-to-grip separation was 50 mm and a preload of 0.01 N was applied. The specimen deformation was derived from the grip-to-grip separation; therefore the presented values of Young's modulus (calculated from the initial slope of the stress-strain curves) give only an indication of the stiffness of the polymers.

To assess their behaviour under dynamic loading conditions, the specimens (n=1) were repetitively (20×) elongated to 50% strain at 50 mm/min in cyclic tests. After a 2 h recovery period, the permanent deformation was estimated from the stress-strain diagram of the 21$^{st}$ cycle. In these experiments a preload of 0.01 N was applied, the deformation was derived from the grip to grip separation. The error in the values is approximately 0.5% strain.

Wettability and Water Uptake

Contact angle measurements were performed on films prepared by casting polymer solutions in dichloromethane (approximately 1 wt %) on glass discs (n=8 per material), drying under vacuum, and photocross-linking in an inert atmosphere. Measurements were done after extracting the photocross-linked films with ethanol. At room temperature, the static, advancing and receding contact angles of ultra-pure water (MilliQ Plus-Millipore, France) on the different surfaces were determined using a video-based system (OCA 20 DataPhysics Instruments GmbH, Germany) equipped with an electronic syringe module.

The equilibrium water uptake of the compression moulded and photocross-linked films was determined after extraction with ethanol. The specimens (n=4) were conditioned in PBS (pH=7.4) at 37° C. for one week. Water uptake was defined as the mass increase of the specimens.

In Vitro Enzymatic Erosion

Cholesterol esterase (CE) from porcine pancreas was used to study the enzymatic hydrolysis of PTMC-based photocross-linked films. Aqueous CE enzyme solutions were prepared at a concentration of 20 µg/mL using phosphate buffered saline (PBS, pH=7.4) containing 0.02 wt % NaN$_3$ (Sigma, U.S.A.) as a bactericide. Ethanol extracted, disk-shaped films (8 mm diameter, approximately 500 µm thickness, n=3 per time point) were placed in vials containing 1 ml of enzyme solution and conditioned at 37° C. The medium was refreshed once every two days. Control experiments without enzyme were performed using PBS (pH 7.4, n=1 per time point). At predetermined time points, the mass and thickness of wet specimens were determined after rinsing and blotting their surfaces. The measurements were performed again after drying the specimens to constant weight in vacuo at room temperature.

Fabrication of Tissue Engineering Scaffolds

Fused deposition modelling was used to fabricate three dimensional (3D) scaffolds with interconnected pores. Solutions were prepared by dissolving the PTMC homopolymer or the PTMC blends together with PETA and the photoinitiator in dichloromethane in the dark, and adding 80 wt % (based on the total polymer mass) of ethylene carbonate (melting temperature 35-38° C.). After evaporation of dichloromethane, the ethylene carbonate solution (containing polymer(s), PETA, and photoinitiator) was extruded at 100-120° C. and 4 bar nitrogen pressure using a Bioplotter device (Envisiontec GmbH, Germany).

Three dimensional scaffolds were plotted by deposition of up to 20 layers (each layer measured 12×12 mm) of fibres extruded through a stainless steel needle with internal diameter of 260 µm. The plotting parameters were: distance between the centres of neighbouring fibres: 500 µm, layer thickness: 130 µm. After each successive layer the plotting direction was changed by 90°. The fibre deposition speed was 100-200 mm/min. Cold air was blown over the built structure to crystallize ethylene carbonate. After plotting, the scaffolds were kept at 4° C. until further use.

The scaffolds were cross-linked by UV irradiation for 300 min. During irradiation, the temperature was maintained at approximately 20° C. by flowing cold nitrogen through the cross-linking chamber. This prevents melting of ethylene carbonate and provides an inert atmosphere. Subsequently, the scaffolds were placed in gently stirred Milli-Q water at 4° C. for 5 days to leach out ethylene carbonate (the water was refreshed twice a day). The scaffolds were then placed in ethanol to remove other possible leachables and dried to constant weight under vacuum. The porosity of the scaffolds was determined using the known densities of the polymers (Densities were 1.31 g/cm$^3$ and 1.29 cm$^3$ for PTMC homopolymer and the blends, respectively.) and by measuring the density of the fabricated scaffolds.

The surface and the cross-section of the scaffolds were analysed by scanning electron microscopy (SEM, Philips XL 30 ESEM-FEG, The Netherlands) at an operating voltage of 5 kV after sputter coating the surfaces with gold.

Human Mesenchymal Stem Cell (hMSCs) Seeding and Culturing in 3D Fabricated Tissue Engineering Scaffolds Photocross-linked and ethanol-extracted scaffolds (approximately 1 mm thick) prepared from the PTMC and the blends were sterilized by immersing in 70% ethanol for 15 min. Then, the scaffolds were washed and incubated three times at room temperature for two hours with sterile PBS. Prior to cell culturing, the scaffolds were incubated in cMEM proliferation media overnight at 37° C.

hMSCs were obtained from a donor undergoing total hip replacement surgery, who gave informed consent. Approval was obtained from the local medical ethical committee. The thawed cells (passage 2) were plated at 1,000 cells/cm$^2$ in 300 cm$^2$ T-flasks (T-300 flasks) in αMEM proliferation medium. hMSCs were expanded for one week with one refreshment of the αMEM proliferation medium. Cell numbers were determined with a particle count and size analyzer (Z2, Beckman Coulter, Fullerton, Calif.). A volume from the cell suspension equivalent to 5×10$^5$ hMSCs—passage 3—was placed on each scaffold with a pipette; these were then placed in wells of a 25-well non-tissue-culture treated plates (Nunc) for four hours in an incubator. After this time period, the medium in the wells was replaced with 2 ml fresh αMEM proliferation medium. The cell-seeded scaffolds were cultured for time periods of 5 or 10 days. In the 10 day culturing period the medium was refreshed at day 5. Directly after seeding, and at day 5 and 10, the cell-containing constructs were washed with PBS and the cells were fixated with 1.5% glutaraldehyde/0.14 M cacodylate buffer for 15 min. Methylene blue was used to stain the viable cells, which were observed using a stereomicroscope. Samples of medium were drawn from different wells (n=3) to obtain metabolic profiles of the cells. Glucose and lactate concentrations were determined using the Vitros DT60 II system (Ortho-Clinical Diagnostics, Tilburg, The Netherlands).

Results

To prepare elastomeric photocross-linked PTMC-based network films and scaffolds, PTMC homopolymers and block copolymers of PTMC with mPEG and PCL were synthesized.

Characteristics of PTMC-based Polymers

The characteristics of the synthesized high molecular weight PTMC homopolymers after purification and compression moulding are given in Table 5. The polymer molecular weights could be adjusted by varying the amount of hexanediol used as initiator in the polymerisation reaction. The molecular weights of the PTMC polymers after compression moulding did not differ much from the purified polymers.

Table 5 also shows the characteristics of the PTMC-PCL-PTMC and mPEG-PTMC block copolymers after purification. The monomer conversions in the block copolymer synthesis were higher than 99%. The TMC contents in the block copolymers were very close to the charged amounts.

TABLE 5

Characteristics of the purified TMC-based polymers used to prepare photocross-linked networks

| Polymer | Hexanediol content (mol %) | TMC content (mol %)$^a$ | $\overline{Mn}^a$ (kg/mol) | $\overline{Mn}^b$ (kg/mol) | $\overline{Mw}^b$ (kg/mol) | PDI$^b$ | [η]$^b$ (dl/g) |
|---|---|---|---|---|---|---|---|
| PTMC$_{45}$ | 0.2 | 100 | — | 45(47) | 75(80) | 1.7(1.7) | 1.3(1.2) |
| PTMC$_{183}$ | 0.03 | 100 | — | 183(159) | 227(196) | 1.2(1.2) | 2.6(2.4) |
| PTMC$_{373}$ | 0 | 100 | — | 373(366) | 474(471) | 1.3(1.3) | 5.7(5.2) |
| PTMC$_{443}$ $^c$ | | | | 443(436) | 620(698) | 1.5(1.6) | 6.6(7.1) |
| PTMC-PCL-PTMC | 0 | 60.4 | 24 | 15 | 26 | 1.7 | 0.5 |
| mPEG-PTMC | 0 | 60.7 | 27 | n.d. | n.d. | n.d. | n.d. |

$^a$Determined after purification by $^1$H NMR using CDCl$_3$ as the solvent.
$^b$Determined after purification by GPC at 30° C. using chloroform as the eluent. The values for compression moulded polymers are given in brackets.
n.d.: not determined UV Cross-Linking of PTMC-Based Films To photocross-link high molecular weight PTMC, compression moulded films containing PETA and a photoinitiator were irradiated with short-wave UV light (254 nm). Upon irradiation with UV light, PTMC could be effectively cross-linked with relative ease, resulting in transparent films. FIGS. 12A and 12B show the gel contents and swelling ratios determined using chloroform of the photocross-linked PTMC networks as a function of irradiation time. The gel contents initially increased rapidly with increasing irradiation time and then increased slowly. In accordance with the increasing gel contents the swelling ratios of the formed networks in chloroform decreased with increasing irradiation time, indicating that denser networks were formed at longer irradiation times.

At 300 minutes of UV exposure, depending on the initial molecular weight of the polymer the gel contents of the networks ranged from 57±1 to 98±1% and the swelling ratios ranged from 11.3±0.8 to 3.7±0.1.

Adjusting the PETA content in the PTMC films also allowed preparation of photocross-linked networks with varying gel contents and swelling ratios. For instance, irradiating the $PTMC_{183}$ polymer containing 1, 3, 5% PETA for 180 minutes lead to networks with gel contents of 41, 71, and 91% and with swelling ratios of 65, 14, 7 vol/vol, respectively. These results demonstrate that PETA content, UV irradiation time, and the initial polymer molecular weight can be varied to adjust the gel content of the networks and the network density. Photocross-linked PTMC networks can be prepared from three-armed PTMC-methacrylate macromers having molecular weights from 0.7 to 40.7 kg/mol. The swelling ratios of these networks in chloroform ranged from 3.1 to 16.9. By comparing these results with the swelling ratios of these PTMC-macromer-based networks, it can be estimated that the molecular between the cross-links of the PTMC networks (containing PETA and photoinitiator and irradiated with UV light for 300 min) range to a first approximation from 1100 to 7600 kg/mol depending on the initial molecular weight of the polymer.

Photocross-linking PTMC using only a cross-linking reagent and a photoinitiator is more practical than by using end-functionalized macromers of different arm lengths and to prepare networks of varying cross-link densities. Furthermore, it has been observed that (meth)acrylate end-functionalized PTMC oligomers can cross-link prematurely before processing even in the presence of radical sccavengers (unpublished data). The PETA containing polymer films used in this study were still soluble in chloroform, even after compression moulding implying that no cross-linking had occurred prior to UV exposure.

Interestingly, when PTMC homopolymer films that did not contain PETA and Irgacure® 369 were exposed to UV light, the number and weight average molecular weights of the polymers increased. After 300 minutes of irradiation, the $\overline{M}_n$ values of $PTMC_{45}$, $PTMC_{183}$, and $PTMC_{373}$ were 49, 244, and 435 kg/mol, respectively. The corresponding PDI values were 2.2, 1.9, and 1.3. We observed that, prolonged irradiation of very high molecular weight PTMC with short wave UV light, lead to cross-linking of the polymer. Upon 48 hours of irradiation of compression moulded films of $PTMC_{443}$, networks with gel contents of 53±13%, and swelling ratios of 84±10 vol/vol in chloroform were formed.

Irradiation of PTMC films which contained only Irgacure®-369 and no PETA resulted in network formation, but the gel contents were much lower than that of the films which contained both PETA and Irgacure®-369. Upon 300 minutes of UV irradiation, $PTMC_{183}$ and $PTMC_{373}$ films that contained 0.025 wt % photoinitiator only had gel contents of 25±3 and 50±2% and swelling ratios of 253±6 and 72±4 vol/vol, respectively. This difference between the gel contents of films that contained only photoinitiator or both photoinitiator and PETA could be due to efficient incorporation of the acrylate network to PTMC chains. $^1$H-NMR analysis of the sol fraction of photocross-linked PTMC films did not reveal any acrylate related peaks. This implies that all PETA had been incorporated to the formed networks.

In addition to PTMC polymers and blends, the photocross-linking of PCL films was investigated for films that contained the same amount of PETA and photoinitiator as the PTMC films. Initial results showed that PCL can also be photocross-linked in this manner. A relatively low molecular weight ($\overline{M}_n$=46 kg/mol) PCL homopolymer film had a gel percentage of 41±1 and swelling ratio of 11.3±0.7 vol/vol in chloroform.

Also blends of $PTMC_{373}$ with PTMC-PCL-PTMC or with mPEG-PTMC block copolymers which contained 5 wt % PETA and photoinitiator could be photocross-linked efficiently. Upon 300 minutes of UV irradiation the gel contents of the $PTMC_{373}$/PTMC-PCL-PTMC blend and the $PTMC_{373}$/mPEG-PTMC blend were 96±1 and 93±1, respectively. The corresponding swelling ratios in chloroform were 6.3±0.1 and 6.1±0.6 vol/vol. Prior to UV exposure, the blends contained 90 wt % $PTMC_{373}$. $^1$H-NMR analyses of the sol fractions of the networks revealed that the block copolymer contents were higher than in the initial film. It could be shown that approximately 75-80% of the block copolymers had been incorporated into the networks upon exposing the films to UV irradiation.

Mechanical Properties of Photocross-Linked PTMC-Based Networks

To evaluate the effect of photocross-linking on the tensile mechanical properties of PTMC polymers, measurements were performed on non-irradiated compression moulded PTMC films and on PTMC films that contained 5 wt % PETA and 0.025 wt % photoinitiator and irradiated with UV light for 300 min (the films irradiated by UV light for 300 min are abbreviated as $PTMC_x$-300). An overview of the tensile mechanical properties of noncross-linked and photocross-linked PTMC homopolymers, as well as photocross-linked $PTMC_{373}$/PTMC-PCL-PTMC and $PTMC_{373}$/mPEG-PTMC blends are given in Table 6.

All PTMC homopolymers are flexible materials with elastic moduli ranging from 3.7±0.1 to 7.7±0.3 MPa. Their yield strength, stress at break, and strain at break values increased with increasing polymer molecular weight. The photocross-linked PTMC network films were also flexible materials, although their elastic moduli were higher than of noncross-linked PTMC films. The values ranged from 7.2±0.2 to 9.6±0.3 MPa. The yield strength and the ultimate tensile strength of PTMC homopolymers increased significantly upon photocross-linking. Depending on the initial polymer molecular weight, the stress at break values of the noncross-linked films ranged from 0.2±0.1 MPa to 6.7±2.8 MPa. Upon cross-linking, the stress at break values of the films increased and ranged from 2.7±0.1 to 30±9 MPa. Moreover, the energy needed to break the photocross-linked PTMC network films was 3 to 9 times higher than the noncross-linked PTMC films, implying that the toughness of PTMC films can be improved significantly by photocross-linking in the presence of PETA. Table 6 clearly illustrates that, depending on the initial PTMC molecular weight, PTMC networks having a range of yield strength, ultimate tensile strength and toughness can be obtained.

The tensile measurements were also performed after extracting the sol fraction of the PTMC network films with ethanol, a relatively poor solvent for PTMC. The enhancement of properties was most pronounced for the networks prepared from $PTMC_{45}$ as the extracted films had higher elastic modulus, yield strength, stress at break, and energy to break values. In the case of the networks prepared from $PTMC_{183}$ and $PTMC_{373}$, these values also seemed to increase slightly.

Photocross-linked films prepared from blends of $PTMC_{373}$ with the relatively low molecular weight mPEG-PTMC block copolymer had only slightly lower elastic moduli and yield strength values than those of nonextracted networks prepared from $PTMC_{373}$ while their stress at break and energy to break values were comparable. This shows that blending $PTMC_{373}$ with up to 10% mPEG-PTMC does not deteriorate the tensile properties significantly in the dry state. Networks obtained from the blends with PTMC-PCL-PTMC block copolymer however had lower yield strength, ultimate tensile strength and toughness than networks prepared from $PTMC_{373}$ only. The tensile properties of the networks prepared from the blends were not affected much by extraction of the sol fraction with ethanol.

films after applying 20 cycles of 50% strain and a 2 h recovery period. It can be seen that the permanent deformation of PTMC homopolymers significantly decreased upon photocross-linking: Ethanol extracted PTMC networks showed comparable creep behaviour with the nonextracted networks in the cyclic tests, although permanent deformation seemed to be slightly lower for the extracted network films. Permanent deformation values were as low as 1.0% strain after photocross-linking and extraction of $PTMC_{373}$. Comparison of FIGS. 13A, 13B, 13C and the permanent set values in Table 6, shows that the photocross-linked networks prepared from $PTMC_{373}$ showed the least hysteresis, the least stress relaxation and the least permanent deformation in cyclic tests. This implies that high initial PTMC molecular weights allows preparation of networks with better elastomeric properties than those prepared from polymers of relatively lower initial molecular weights.

FIG. 13D and the permanent set values in Table 6 show that the photocross-linked blends also have excellent elastomeric properties. It can be seen that blending $PTMC_{373}$ with PTMC-PCL-PTMC or mPEG-PTMC does not have an adverse effect on the cyclic creep behaviour of the networks.

TABLE 6

The effect of photocross-linking in the presence of PETA on the mechanical properties of PTMC-based polymers. Values are expressed as mean ± standard deviation, (n = 3).

| Polymer-Irradiation time (min) | PETA content (wt %) | Ethanol extraction | E (MPa) | $\sigma_{yield}$ (MPa) | $\epsilon_{yield}$ (%) | $\sigma_{break}$ (MPa) | $\epsilon_{break}$ (%) | Energy to break (Joules) | Permanent Set [a] (%) |
|---|---|---|---|---|---|---|---|---|---|
| $PTMC_{45}$-0 | 0.0 | No | 3.7 ± 0.1 | 0.5 ± 0.1 | 71 ± 3 | 0.2 ± 0.1 | 479 ± 165 | 0.2 ± 0.05 | 22.0 |
| $PTMC_{45}$-300 | 5.0 | No | 7.2 ± 0.2 | 2.1 ± 0.1[b] | 107 ± 3[b] | 2.7 ± 0.1 | 530 ± 79 | 1.4 ± 0.3 | 3.0 |
| $PTMC_{45}$-300 | 5.0 | Yes | 9.8 ± 0.3 | 2.7 ± 0.1[b] | 93 ± 3[b] | 4.4 ± 0.5 | 515 ± 29 | 2.1 ± 0.2 | 2.0 |
| $PTMC_{183}$-0 | 0.0 | No | 6.9 ± 0.5 | 1.4 ± 0.1 | 116 ± 5 | 1.1 ± 0.1 | 532 ± 44 | 0.7 ± 0.1 | 8.0 |
| $PTMC_{183}$-300 | 5.0 | No | 9.2 ± 0.1 | 3.6 ± 0.2[b] | 98 ± 3[b] | 19 ± 5 | 706 ± 61 | 6.6 ± 1.6 | 1.5 |
| $PTMC_{183}$-300 | 5.0 | Yes | 9.5 ± 0.2 | 3.9 ± 0.1[b] | 97 ± 3[b] | 21 ± 3 | 610 ± 47 | 6.7 ± 0.3 | 1.3 |
| $PTMC_{373}$-0 | 0.0 | No | 7.7 ± 0.3 | 2.2 ± 0.1 | 126 ± 10 | 6.7 ± 2.8 | 847 ± 73 | 2.5 ± 0.6 | 2.2 |
| $PTMC_{373}$-300 | 5.0 | No | 9.6 ± 0.3 | 4.4 ± 0.3[b] | 93 ± 6[b] | 30 ± 9 | 560 ± 79 | 7.7 ± 2.7 | 1.5 |
| $PTMC_{373}$-300 | 5.0 | Yes | 10.5 ± 0.2 | 4.6 ± 0.2[b] | 102 ± 10[b] | 35 ± 4 | 622 ± 26 | 9.5 ± 1.4 | 1.0 |
| $PTMC_{373}$/PTMC-PCL-PTMC-300 | 5.0 | No | 9.9 ± 0.3 | 3.9 ± 0.1[b] | 87 ± 6[b] | 19 ± 2 | 513 ± 3 | 4.1 ± 0.4 | 1.1 |
| $PTMC_{373}$/PTMC-PCL-PTMC-300 | 5.0 | Yes | 10.3 ± 0.1 | 3.9 ± 0.1[b] | 95 ± 8[b] | 17 ± 3 | 608 ± 65 | 4.1 ± 0.9 | 1.1 |
| $PTMC_{373}$/mPEG-PTMC-300 | 5.0 | No | 8.8 ± 0.5 | 4.0 ± 0.1[b] | 103 ± 3[b] | 30 ± 6 | 630 ± 39 | 8.4 ± 1.9 | 1.2 |
| $PTMC_{373}$/mPEG-PTMC-300 | 5.0 | Yes | 10.0 ± 0.3 | 4.1 ± 0.2[b] | 96 ± 1[b] | 34 ± 1 | 645 ± 22 | 9.4 ± 0.3 | 1.3 |

[a] Single measurements. The permanent set is estimated from the 21$^{st}$ cycle, performed after a two hours recovery period. The error is approximately 0.5% strain.
[b] Estimated from the intersection of tangents to stress-strain diagrams as a distinct yield point could not be observed.

As these PTMC networks are intended to withstand repeated dynamic loadings in vitro as well as in vivo, cyclic tests were performed to assess the effect of photocross-linking on their creep behaviour under dynamic conditions. FIGS. 2A, 2B, and 2C show the hysteresis behaviour of PTMC polymers before and after photocross-linking. These figures clearly demonstrate that in all cases photocross-linking of PTMC in the presence of PETA and photoinitiator significantly reduces hysteresis with reduced extent of creep observed in each successive cycle. In the noncross-linked state, $PTMC_{45}$, $PTMC_{183}$ and $PTMC_{373}$ had creep values of 45, 29, 15%, respectively at the end of the 20$^{th}$ cycle. Upon photocross-linking in the presence of PETA and photoinitiator, the values significantly decreased: $PTMC_{45}$-300, $PTMC_{183}$-300 and $PTMC_{373}$-300 had creep values of 29, 12, and 8%, respectively. Moreover, the stress relaxation (the decrease in maximum stress reached in each cycle) of the PTMC films was also very much reduced upon photocross-linking. Table 6 shows the permanent deformation of these In Vitro Enzymatic Erosion and Wettability of Photocross-Linked PTMC-Based Networks The enzymatic erosion of photocross-linked networks based on $PTMC_{373}$ was investigated using aqueous cholesterol esterase solutions. This enzyme is one of the secretory products of macrophages, and is known to effectively degrade gamma irradiated and photocross-linked PTMC networks. The changes in relative mass and thickness of the incubated polymer films in time is given in FIG. 14. The erosion of linear $PTMC_{373}$ homopolymer was relatively fast in aqueous cholesterol esterase solutions. Upon 11 days of incubation, the mass loss of the $PTMC_{373}$ specimens was 84±2.5% corresponding to a rate of mass loss of 2.48±0.45 mg/(cm$^2$×day).

The mass loss of photocross-linked films of $PTMC_{373}$-300, $PTMC_{373}$/PTMC-PCL-PTMC-300, and PTMC373/mPEG-PTMC-300 after 28 days of incubation in aqueous enzyme solution were 24±2.7, 16±1.8, and 1.5±0.4%, respectively (FIG. 14A). The corresponding rates of mass loss were 0.41±0.11, 0.27±0.07, and 0.017±0.01 mg/(cm$^2$×day). Photocross-linking the PTMC$_{373}$ films resulted in networks with much reduced erosion rates allowing their use in long-term biomedical applications. The decrease in erosion rates could be due to hindered mobility of the chains as a result of dense network formation as the chains need to adopt the correct conformation for enzymatic attack. These results also show that the enzymatic erosion rates of PTMC networks can be tuned by blending and photocross-linking with block copolymers. Especially, when blended with the mPEG-PTMC block copolymer, enzymatic erosion was dramatically reduced. It is likely that the surface characteristics of mPEG-PTMC containing blends did not allow binding of the enzyme to the surface of the polymers, as it was suggested that this enzyme is most active at a hydrophilic-hydrophobic interface. Indeed in Table 7 it can be seen that the photocross-linked networks which contain mPEG-PTMC block copolymer have significantly lower contact angles and somewhat higher water uptake values than the photocross-linked networks prepared from PTMC$_{373}$ homopolymer or from its blends with the PTMC-PCL-PTMC block copolymer. It is clear that the surface characteristics of photocross-linked PTMC networks can be easily tailored by blending with a hydrophilic-hydrophobic block copolymer.

TABLE 7

Effect of photocross-linking and blending with block copolymers on water contact angles and water uptake values of PTMC$_{373}$-based films. Values are expressed as mean ± standard deviation.

| Polymer | Water contact angle (°)$^a$ | | | Water uptake (%)$^a$ |
| --- | --- | --- | --- | --- |
| | Static | Advancing | Receding | |
| PTMC$_{373}$ | 77.4 ± 0.8 | 80.4 ± 0.4 | 48.6 ± 3.5 | 1.4 ± 0.3 |
| PTMC$_{373}$-300 | 98.9 ± 3.4 | 101.5 ± 2.6 | 65.1 ± 1.8 | 1.2 ± 0.2 |
| PTMC$_{373}$/PTMC-PCL-PTMC-300 | 94.6 ± 2.8 | 95.9 ± 2.8 | 63.6 ± 2.3 | 1.3 ± 0.2 |
| PTMC$_{373}$/PTMC-mPEG-300 | 60.6 ± 1.0 | 63.1 ± 1.0 | 30.4 ± 1.2 | 1.8 ± 0.2 |

$^a$Performed on polymer films cast on glass discs (n = 8).
$^b$Compression moulded, photocross-linked, and exracted films were conditioned in PBS at 37° C. for one week (n = 4).

The non-irradiated PTMC$_{373}$ films had an average static contact angle of 77.4±0.8. Interestingly, the contact angles of UV irradiated PTMC$_{373}$ films which contained PETA and photoinitiator (PTMC$_{373}$-300) were significantly higher (98.9±3.4) than those of the non-irradiated. To assess the sole effect of UV irradiation, we irradiated PTMC$_{373}$ films which did not contain PETA or photoinitiator. After 300 min of irradiation, the static, advancing, and receding contact angles of PTMC$_{373}$ were 85.3±1.1°, 87.5±0.9°, and 52.0±1.4°, respectively, which were also higher than non-irradiated PTMC. This confirms that the cross-linking was done under inert conditions, as short wavelength ultraviolet irradiation in air would lead to oxidation of the surface of the polymer and increase hydrophilicity (lower contact angles). It was reported that, the contact angle of PMMA also increases approximately 20° upon vacuum UV irradiation (126 nm) at a reduced pressure of 2×10$^4$ Pa. This was related to increase in percentage of carbon at the polymer surface. FIG. 7B shows that the thickness of noncross-linked PTMC$_{373}$ films and of the photocross-linked PTMC$_{373}$-300 and PTMC$_{373}$/PTMC-PCL-PTMC-300 films also decreased in time during enzymatic degradation. This indicates that these polymer and network films eroded by a surface erosion process. No significant decrease in thickness of the PTMC$_{373}$/mPEG-PTMC-300 specimens could be determined but SEM analysis revealed surface pitting of these films to some extent, confirming their slow surface erosion (data not shown).

Photocross-Linked PTMC-Based Tissue Engineering Scaffolds

For the fabrication of TE scaffolds, solutions of the polymer (PTMC$_{373}$ homopolymer, PTMC$_{373}$/PTMC-PCL-PTMC or PTMC$_{373}$/mPEG-PTMC blend), PETA, photoinitiator, and ethylene carbonate were prepared. Photocross-linked three dimensional PTMC-based scaffolds were prepared by computer controlled extrusion of the polymer solutions using a bioplotter, photocross-linking, and extraction of ethylene carbonate and other possible leachables in water and ethanol.

The scaffolds prepared from flexible PTMC-based polymers had high porosities of 70±6% with interconnected pores. FIG. 4 shows SEM micrographs of the photocross-linked scaffolds prepared from PTMC$_{373}$ polymer. Similar structures were also obtained when PTMC$_{373}$/PTMC-PCL-PTMC or PTMC$_{373}$/mPEG-PTMC blends were used. It can be seen from FIGS. 15A and 15B that the distance between the fibres plotted in the x or y directions was approximately 200-250 μm and the diameter of the fibres ranged between 100-150 μm. The height of the pores ranged from 50 to 100 μm (FIG. 15D).

Use of ethylene carbonate (EC), as a solvent allowed the extrusion of high molecular weight PTMC polymers at relatively low temperatures of 100-120° C. Without the use of EC, temperatures higher than 220° C. are required even for the extrusion of the relatively low molecular weight PTMC$_{45}$ polymer. Moreover, cooling the extruded fibres with cold nitrogen induced crystallisation of ethylene carbonate. Crystallisation of EC not only provided the required form-stability to the extruded fibres of amorphous PTMC polymers, but also lead to formation of fibres with microporosity. These micropores (ranging from few microns to few tens of microns) in the fibres and the roughness of the surface of the fibres can be seen especially clearly in FIG. 15C. Microporosity of these PTMC scaffolds can be advantageous in tissue engineering as the attachment of cells to substrates and their viability has been shown to improve with surface roughness. This microporosity could also lead to an enhancement in the transport of nutrients to the cells and removal of waste products from the cells.

Human mesenchymal stem cells (hMSCs) were seeded in photocross-linked (300 min) PTMC-based scaffolds and cultured for 10 days. FIG. 16 shows the viable cells that were stained with methylene blue. It can be seen that the number of cells that are present on and in scaffolds prepared from PTMC$_{373}$ and PTMC$_{373}$/PTMC-PCL-PTMC increased from the day of seeding (FIGS. 16A, 16D) to day 5 (FIGS. 16B, 16E). After 10 days of culturing, these scaffolds contained very high numbers of viable cells as can be seen from extensive (blue) staining in FIGS. 16C and 16F. The amount of cells on and in the scaffolds prepared from PTMC$_{373}$/mPEG-PTMC blends was much less than the other two materials. The hydrophilic nature of this material probably did not allow adsorption of cell binding proteins that are present in the cell culture medium which hindered hMSC adhesion to these surfaces.

These observations were corroborated by SEM (FIG. 17). After 5 days of culturing, hMSCs with stretched fibroblast-like morphology were observed on the fibres (FIGS. 17A, 17D, 17G). FIGS. 17B and 17E show that the hMSCs proliferated and the surface of the photocross-linked scaffolds prepared from PTMC$_{373}$ and PTMC$_{373}$/PTMC-PCL-PTMC were almost completely covered with the cells. It can be seen from the cross sections in FIGS. 17C, and 17F that cells were also present inside the scaffolds and had produced extracellular matrix. This indicates that these materials were compatible with hMSCs. Also with SEM, low numbers of cells were seen on scaffolds prepared from $PTMC_{373}$/mPEG-PTMC blends.

During hMSC culturing, the metabolic profile of the cells were monitored by determining the glucose and lactate concentrations in the culture media. FIGS. 18A and 18B show the glucose and lactate concentrations on day 5, 8 and 10 (Note that the medium was refreshed on day 5.). In all cultures, glucose concentrations decreased whereas lactate concentrations increased in time. As higher numbers of cells were present in photocross-linked scaffolds prepared from $PTMC_{373}$ and $PTMC_{373}$/PTMC-PCL-PTMC, glucose consumption and lactate production were high in the wells containing these cell-seeded scaffolds. In the wells that contained cell-seeded scaffolds prepared from $PTMC_{373}$/mPEG-PTMC blends glucose consumption and lactate production were low, as there were significantly less cells in these scaffolds. The rates of glucose consumption for cultures using scaffolds of $PTMC_{373}$-300, $PTMC_{373}$/PTMC PCL PTMC-300, and $PTMC_{373}$/mPEG PTMC-300 were 23.3±1.7, 25.0±2.4, and 9.8±1.5 µM/h, respectively. The corresponding lactate production rates were 60.8±6.5, 63.2±8.1, and 34.1±3.9. These results suggest that the scaffolds of $PTMC_{373}$-300 and $PTMC_{373}$/PTMC-PCL-PTMC-300 were more suited for tissue engineering applications than those prepared from $PTMC_{373}$/mPEG-PTMC. (However, the networks containing mPEG-PTMC block copolymer might be used to improve the blood compatibility of biomaterials such as vascular grafts.)

Conclusion

This study shows that flexible and tough PTMC networks with excellent elastomeric properties and reduced enzymatic erosion rates can be obtained by efficient photocross-linking of PTMC films containing PETA and photoinitiator. The properties of these PTMC networks such as wettability and enzymatic erosion can be easily tailored by blending with PCL or PEG containing block copolymers. Tissue engineering scaffolds with interconnected pores and extensive microporosity can be obtained by fused deposition modelling of thermoplastic PTMC polymer and subsequent UV photo-cross-linking of the scaffolds. Photocross-linked scaffolds prepared from $PTMC_{373}$ polymer and $PTMC_{373}$/PTMC-PCL-PTMC blends are suitable for tissue engineering applications as they allowed adhesion and proliferation of human mesenchymal stem cells. This versatile cross-linking method offers interesting opportunities for the facile cross-linking of high molecular weight polymers and modification of their properties in this manner.

Example 4

Materials

Polymer grade 1,3-trimethylene carbonate (TMC, Boehringer Ingelheim, Germany), 1,3-propanediol, trimethylol propane, and stannous octoate (all from Sigma, U.S.A. or Germany) were used as received. Methacrylic anhydride and hydroquinone were purchased from Aldrich (Germany). (±)-☐-tocopherol was obtained from Fluka (Switzerland). Solvents (Merck, Germany or Biosolve, The Netherlands) were of analytical grade. Photoinitiators Irgacure® 2959 (1-[4[(2-hydroxyethoxy)-phenyl]-2-hydroxy-2-methyl-1-propane-1-one) Irgacure® 369 (2-Benzyl-2-dimethylamino-1-(4-morpholinophenyl)-butanone-1), Irgacure® 500 (50% 1-hydroxy-cyclohexyl-phenyl-ketone, 50% benzophenone) (Ciba®, Switzerland), benzophenone (Aldrich, Germany), and DMPA (2,2-dimethoxy-2-phenyl acetophenone) (Aldrich, Germany) were used as received.

J774A macrophages (ATCC-TIB-67) were obtained from the American Type Culture Collection. Culture media, fetal bovine serum, Glutamax™ and penicillin-streptomycin were obtained from Invitrogen (Gibco, U.S.A.). Culture disposables were from Nunc (U.S.A.) and Greiner (Germany).

For human mesenchymal stem cell culturing, α-minimum essential medium (α-MEM, Gibco U.S.A.) was used. This medium also contained fetal bovine serum (10%, Biowhitaker, Belgium), penicillin G (100 Units/ml, Invitrogen U.S.A.) and streptomycin (100 µg/ml, Invitrogen U.S.A.), L-glutamine (2 mM, Sigma, U.S.A.). Cholesterol esterase (CE) from porcine pancreas (Sigma, U.K., 56.2 U/mg) and potassium dioxide ($KO_2$, Sigma, U.S.A.) were dissolved in phosphate buffered saline (PBS, pH=7.4, B. Braun Melsungen A.G., Germany) and NaOH/NaCl buffer solution (pH=13, Scharlau Chemie, Spain), respectively prior to use.

Synthesis of PTMC Polymer and PTMC Macromer Cross-Linking Reagents

Linear high molecular weight poly(trimethylene carbonate) (PTMC) was synthesized by ring opening polymerization of the TMC monomer under vacuum at 130° C. for three days using stannous octoate as catalyst. The polymer was purified by dissolution in chloroform and precipitation into ethanol, washing with fresh ethanol and drying at room temperature under vacuum.

By using 1,3-propanediol (20 mol %) or trimethylol propane (14.3 mol %) as initiators, two-armed and three-armed hydroxyl-group terminated PTMC oligomers (see FIG. 19) were synthesized by ring-opening polymerization (oligomerization). The syntheses were conducted under argon at 130° C. for 48 h, using stannous octoate as catalyst. To obtain methacrylate-functionalized PTMC oligomers (macromers), the hydroxyl-group terminated oligomers were reacted with a 30 mol % excess of methacrylic anhydride at 120° C. for 8 h. To prevent premature cross-linking during this step, hydroquinone and (±)-α-tocopherol (0.06 wt %) were used as inhibitors. The excess methacrylic anhydride and the formed methacrylic acid were removed by distillation under reduced pressure. The PTMC macromers were further purified by dissolution in acetone, precipitation into water and freeze drying.

Characterisation

Conversion of TMC monomer was determined by proton nuclear magnetic resonance ($^1$H-NMR) spectroscopy (300 MHz, Varian Innova, U.S.A.) using $CDCl_3$.

Number average- and weight average molecular weights ($\overline{M}_n$ and $\overline{M}_w$, respectively), polydispersity index (PDI) and intrinsic viscosity ([η]) of PTMC was determined by gel permeation chromatography (GPC, Viscotek, U.S.A.). The setup was equipped with ViscoGEL I-guard-0478, ViscoGEL I-MBHMW-3078, and ViscoGEL I-MBLMW-3078 columns placed in series and a TDA 302 Triple Detector Array with refractometer-, viscometer-, and light scattering detectors, allowing the determination of absolute molecular weights. All determinations were performed at 30° C., using chloroform as the eluent at a flow rate of 1.0 ml/min.

Molecular weights of the two- and three-armed macromers (dimethacrylate oligocarbonate, DMAC, and trimethacrylate oligocarbonate, TMAC, respectively) were determined by $^1$H-NMR spectroscopy.

Preparation of PTMC Films

The PTMC homopolymer was mixed with different amounts of photoinitiator and macromer cross-linking reagents by dissolving and mixing the compounds in dichloromethane in the dark. After evaporation of the solvent, compression moulded films were prepared using 500 μm thick stainless steel moulds and a laboratory press (Fonteijne THB008, The Netherlands). The films were moulded at approximately 25 kg/cm², at 140° C. and quenched to room temperature using cold water.

Photocross-Linking and Network Characterization

Compression moulded films containing macromers (DMAC or TMAC) and photoinitiator were vacuum sealed in laminated polyethylene/polyamide bags (Revel Vacuum B.V., The Netherlands) and exposed to short wave UV light (UltraLum cross-linking cabinet, U.S.A., wavelength 254 nm) at a distance of 7 cm. Both sides of the specimens were illuminated at room temperature for different time periods. The light intensity at this distance was 10-14 mW/cm², the polyethylene/polyamide bags reduced the intensity to 5-7 mW/cm² as measured with an optical power meter (Newport 1916-C, U.S.A.).

To determine equilibrium swelling ratios and gel contents, disk-shaped specimens (500 μm thick, 10 mm in diameter) were punched out from the irradiated films and placed in 30 mL $CHCl_3$ for 1 week, the solvent was refreshed once after 3 days. This procedure ensured complete removal of the sol fraction. Then the swollen gels were weighed, dried to constant weight at room temperature in vacuo and weighed again. The gel and the sol fractions were calculated according to equations (1) and (2) respectively:

$$\text{Gel fraction (\%)} = \frac{m_d}{m_0} \times 100 \quad (1)$$

$$\text{Sol fraction (\%)} = \left(1 - \frac{m_d}{m_0}\right) \times 100 \quad (2)$$

where $m_d$ is the mass of dried (extracted) samples and $m_0$ is the mass of the specimens before swelling.

The volume swelling ratio (q) was calculated according to equation (3).

$$q = 1 + \rho_p \times \left(\frac{m_s}{m_d \times \rho_s} - \frac{1}{\rho_s}\right) \quad (3)$$

where $m_s$ is the mass of the extracted and swollen samples, and $\rho_s$ and $\rho_p$ are the densities of chloroform (1.48 g/cm³) and PTMC (1.31 g/cm³), respectively.

Mechanical Properties

The tensile properties of photocross-linked PTMC films measuring approximately 100×5×0.5 mm³ were determined in triplicate after extraction in ethanol according to ASTM-D 882-91. A Zwick 2020 tensile tester (Ulm, Germany) equipped with a 500 N load cell was operated at a crosshead speed of 50 mm/min. The initial grip-to-grip separation was 50 mm and a preload of 0.01 N was applied. The specimen deformation was derived from the grip-to-grip separation; therefore the presented values of Young's modulus (calculated from the initial slope of the stress-strain curves) give only an indication of the stiffness of the polymers.

To assess their behaviour under dynamic loading conditions, the specimens (n=1) were repeatedly (20×) elongated to 50% strain at 50 mm/min in cyclic tests. After a 2 h recovery period, the permanent deformation was estimated from the stress-strain diagram of the $21^{St}$ cycle. In these experiments a preload of 0.01 N was applied, the deformation was derived from the grip to grip separation. The error in the values is approximately 0.5% strain.

Human Mesenchymal Stem Cell Culturing

Human mesenchymal stem cells (hMSCs) were cultured on disk-shaped photocross-linked and ethanol-extracted PTMC films (15 mm in diameter and approximately 200 μm thick). Prior to cell culturing, the films were sterilized by immersing in 70% ethanol for 15 min and then washing with sterile PBS. hMSCs were obtained from a donor undergoing total hip replacement surgery, who gave informed consent. Approval was obtained from the local medical ethical committee. The cells (passage 2) were cultured at an initial seeding density of $5 \times 10^4$ cells/cm² using cMEM. The medium was refreshed twice every week.

After four weeks of culturing, the cells on the films were fixed with 3.7% paraformaldehyde. Half the specimens were sputter-coated with gold and their surfaces were analysed by scanning electron microscopy (SEM, Philips XL 30 ESEM-FEG, The Netherlands) at an operating voltage of 5 kV. The remaining half was used for fluorescence staining of cell nuclei using 4',6-diamidino-2-phenylindole (DAPI). The actin cytoskeleton of the cells was stained using mouse monoclonal α-sarcomeric actin as primary antibody and fluorescein isothiocyanate (FITC) labelled isotype-specific goat anti-mouse secondary antibody. These specimens were then analysed by confocal laser scanning microscopy (CLSM).

In Vitro Erosion Studies

J774A macrophages that were used in macrophage mediated erosion studies were maintained in DMEM containing 4.5 g/L D-glucose, pyruvate, 10% fetal bovine serum, 100 U/mL penicillin, 100 μg/mL streptomycin and 100 μg/mL 2 mM Glutamax™. Cells were passaged every 4 to 7 days by scraping.

The erosion of photocross-linked and ethanol-extracted polymer films in macrophage cultures was investigated by directly culturing J774A macrophages on the surface of the films. The test specimens were 15 mm in diameter and approximately 500 μm in thickness. The seeding density was approximately $8 \times 10^4$ cells/cm². After 8 days of culturing cells on the different surfaces, fresh aliquots of cells were added to the culture. Cells were cultured on six disks of each material. Medium was refreshed once a week.

After 14 days of culturing, three specimens of each material were first placed in Milli-Q water to lyse the cells, and then thoroughly rinsed and weighed. After drying the films to constant weight in vacuo at room temperature, the samples were weighed again. Evaluation of the surfaces of the specimens was performed by SEM as described earlier. The remaining disks of each material (n=3) were fixed with 3.7% para-formaldehyde in cytoskeletal stabilizing (CS) buffer (0.1 M piperazine-1,4-bis(2-ethanesulfonic acid) (PIPES) buffer, 1 mM ethylene glycol tetraacetic acid (EGTA), pH=6.9) for 15 min and then transferred to PBS. The specimens were used for fluorescence staining of cell nuclei using DAPI and of the actin cytoskeleton using tetramethyl rhodamine iso-thiocyanide-phalloidin (TRITC-phalloidin). Samples were analysed using CLSM (Leica TCS SP2 equipped with a 40×NA0.80 full immersion water lens) to allow in depth visualisation of adhered cells.

Cholesterol esterase (CE) from porcine pancreas was used to study the enzymatic hydrolysis of noncross-linked and photocross-linked PTMC films. Aqueous CE enzyme solutions were prepared at a concentration of 20 μg/mL using phosphate buffered saline (PBS, pH=7.4) containing 0.02 wt % $NaN_3$ (Sigma, U.S.A.) as a bactericide. Ethanol extracted, disk-shaped films (8 mm diameter, approximately 500 μm thickness, n=8) were placed in vials containing 1 ml of freshly prepared enzyme solution and conditioned at 37° C. The medium was refreshed once every two days. After 14 days of incubation, the mass of the wet specimens was determined after rinsing and blotting their surfaces. Measurements were performed again after drying the specimens to constant weight in vacuo at room temperature.

In vitro erosion of PTMC (network) films having the same dimensions was also investigated by incubation in aqueous $KO_2$ solutions [5M] that were prepared using a NaOH/NaCl buffer (pH=13). Specimens (n=4) were placed in vials containing 1 mL of the freshly prepared superoxide solutions. The solutions were refreshed daily. After one week incubation at 37° C., mass loss was determined as described earlier.

Wettability and Water Uptake

Contact angle measurements were performed on films prepared by casting polymer solutions in dichloromethane (approximately 1 wt %) on glass discs (n=6 per material), drying under vacuum, and photocross-linking in an inert atmosphere. At room temperature, the static, advancing and receding contact angles of ultra-pure water (MilliQ Plus-Millipore, France) on the different surfaces were determined using a video-based system (OCA 20 DataPhysics Instruments GmbH, Germany) equipped with an electronic syringe module. The equilibrium water uptake of the compression moulded and photocross-linked films was determined after extraction with ethanol. The specimens (n=4) were conditioned in PBS (pH=7.4) at 37° C. for one week. Water uptake was defined as the mass increase of the specimens.

Results

Linear high molecular weight PTMC with $\overline{M}_n$=291 kg/mol was synthesized by ring opening polymerisation of TMC. PTMC macromers were prepared by initiating the ring opening polymerization of TMC with small amounts of 1,3-propanediol or trimethylol propane, and subsequent reaction of the two-armed and three-armed oligomers with methacrylic anhydride. The methacrylate-functionalized DMAC- and TMAC macromers were used as cross-linking reagents during the irradiation of high molecular weight PTMC with UV light.

$^1$H NMR analyses showed that in the ring opening polymerization (oligomerization) reactions the conversion of TMC was higher than 95%, and that in the macromers more than 99% of the hydroxyl endgroups had been converted to methacrylates. The number average molecular weights of the purified DMAC and TMAC macromers were also determined by NMR, the respective values were 810 g/mol and 1100 g/mol (or 2.9 and 2.5 TMC units/arm).

Photocross-Linking of PTMC Films Using Photoinitiators

In preliminary experiments, films of linear high molecular weight PTMC containing different photoinitiators (PI) were prepared and irradiated with short wave UV light for 30 to 120 min. (The PI to TMC repeating unit in the polymer molar ratios were 1:1000). It was surprisingly found that when Irgacure® 2959, Irgacure® 500, or benzophenone were used as PI, PTMC networks with high gel contents were obtained. With these PIs, networks with 84-87% gel were obtained after 120 min irradiation. When PTMC films that contained DMPA, or Irgacure® 369 were irradiated for 120 min, the gel contents were much lower: 62 and 0%, respectively.

Polyethylene and poly(ethylene oxide) also have been shown to cross-link upon UV irradiation in the presence of a photoinitiator that undergoes Norrish type II photolysis, like benzophenone, and acts as a hydrogen abstracting agent. It was proposed for both polymers that cross-linking occurs by combination of two macroradicals to form H-type cross-linkages. In addition, poly(ethylene oxide) could also be cross-linked in the presence of photoinitiators that undergo Norrish type I photolysis (α-cleavage), less efficiently. This was also the case in the experiments with PTMC, where photoinitiators that undergo Norrish type I photolysis (DMPA and Irgacure® 369) gave lowest network gel contents. Irgacure® 2959 was as efficient as benzophenone, and considering its good compatibility with a broad range of mammalian cell types, it was used as PI in further experiments.

The effect of the PI concentration on the gel content and network density was assessed by irradiating PTMC films containing varying amounts of Irgacure® 2959 for durations ranging from 30 min up to 300 min. For all irradiation times (30, 60, 120, 180, 240, and 300 min), increasing the PI content of the PTMC films initially increased the gel contents and decreased the swelling ratios of the formed PTMC networks. FIG. 20 illustrates this for an irradiation time of 120 min. For all irradiation times, the optimal PI/TMC ratio (where the highest gel contents and lowest swelling ratios were obtained) was found to be 1/1000. The decrease in gel contents at PI concentrations higher than 1/1000 is probably due to a decrease in the quantum yield.

This can be due to competing reactions: the photoinitiating radicals can either react with PTMC chains or the phototinitiating radicals can react with each other or with PTMC macroradicals.

For all PI concentrations, irradiating the films for less than 120 min resulted in lower network gel contents and higher swelling ratios. Increasing the irradiation time beyond 120 min did not yield networks with higher gel contents or higher network densities.

Photocross-Linking of PTMC Films Using Irgacure® 2959 Photoinitiator and PTMC Macromers as Cross-Linking Reagents To investigate their cross-linking properties, high molecular weight PTMC films containing varying amounts of Irgacure® 2959 photoinitiator and varying amounts of PTMC macromers were exposed to UV light. In all cases, upon UV irradiation, transparent PTMC networks were formed.

At a constant concentration of PTMC macromers (1/50 methacrylate/TMC repeating unit in the polymer), the gel contents of the formed networks increased and the swelling ratios decreased with increasing PI concentration (1/8000, 1/4000, 1/2000, 1/1000 PI/TMC repeating unit in the polymer). This was observed when both DMAC and TMAC were used as the cross-linking reagent. For instance when DMAC containing films were irradiated for 30 min, the gel content of the formed networks increased from 53±2% to 89±1% as the PI/TMC ratio was increased from 1/8000 to 1/1000. The corresponding swelling ratios in chloroform were 23.2±0.6 and 13.9±0.2 vol/vol. Therefore, the highest PI/TMC ratio of 1/1000 was used in further experiments. When the PTMC films were irradiated for 60 min or 120 min, the same trend was observed: increasing the irradiation time also yielded networks with higher gel contents and lower swelling ratios. The effect of irradiation time and the cross-linking reagent used on the gel content and swelling ratio of the PTMC network films is shown in FIG. 21. The PTMC films had PI/TMC ratios of 1/1000, and methacrylate/TMC ratios of 1/50 for DMAC or TMAC containing films. Depending UV irradiation time, the gel contents and swelling ratios of networks prepared from PTMC films that did not contain a PTMC macromer (PTMC-PI) ranged from 64±3 to 87±2% and from 48±1 to 14.6±1.2 vol/vol, respectively. For the networks prepared from films that contained PTMC macromers, the gel contents ranged from 89±1 to 95±1% for PTMC-PI-DMAC and from 91±1 to 94±1% for PTMC-PI-TMAC. Importantly, the density of these networks could be tuned by adjusting the irradiation time while maintaining high gel contents. The swelling ratios in chloroform ranged from 13.9±0.2 to 8.5±0.1 vol/vol.

It can also be seen in FIG. 2 that using a PTMC macromer in the films as a cross-linking reagent significantly increases the rate of cross-linking, yielding high gel contents and low swelling ratios much faster than PTMC films containing only photoinitiator: After 30 min UV irradiation, PTMC-PI, PTMC-PI-DMAC, and PTMC-PI-TMAC had gel contents of 64±3, 89±1, 91±1%, respectively. The corresponding swelling ratios were 48±1, 13.9±0.2, 12.2±0.3 vol/vol. Differences in characteristics of networks prepared from PTMC films containing a dimethacrylate- or a trimethacrylate cross-linking reagent were minimal, although the TMAC network films seemed to be slightly more densely cross-linked. We also investigated the effect of macromer content in the films on PTMC network formation. At a constant PI/TMC ratio (1/1000), we varied the TMAC content of the films. We could readily tune the network density of these films in this manner as well: The swelling ratios of the networks were 14.6±1.2, 12.4±0.3, 11.4±0.3, 8.5±0.1 vol/vol for methacrylate/TMC ratios of 0, 1/200, 1/100, 1/50, respectively. All abovementioned networks had high gel contents ranging from 87±2 to 94±1%.

The high gel contents and network densities observed, suggest that the macromer is incorporated into the PTMC network.

dynamic conditions in vivo. Therefore, the materials to be used in such applications should be able to withstand and recover from applied repetitive cyclic stresses. We evaluated the creep resistance of the network films by applying 20 cycles of extension to 50% strain. The stress-strain curves showing these 20 cycles for different materials are given in FIG. 23. Non-irradiated PTMC films had the highest creep after 20 cycles (15.3%). After a 2 h recovery period, their permanent set was 1.6% strain (Table 7). The photocross-linked network films showed significantly improved elastic behaviour with much less creep in the cyclic tests. After the 20$^{th}$ cycle, PTMC-PI, PTMC-PI-DMAC, and PTMC-PI-TMAC had creep values of 9.9, 7.5, and 7.6% strain, respectively. The permanent set values for these networks were as low as 0.6% strain.

Another phenomenon observed in the cyclic testing, was decrease in the maximum stress value that is reached at the end of the loading cycle due to stress relaxation. Stress relaxation is undesired, as it would lead to dilatation and failure of constructs such as blood vessel tissue engineering scaffolds and grafts when cyclic stresses are applied. By photo-crosslinking, the stress relaxation of PTMC could also be reduced. For non-cross-linked PTMC, the maximum stress decreased from 3.2 to 2.4 MPa, while in the case of photo-cross-linked films this decrease was only 0.3-0.4 MPa.

TABLE 7

Mechanical properties of PTMC and of PTMC networks prepared by UV photocross-linking of PTMC films containing only photoinitiator or photoinitiator and PTMC macromers. Values are expressed as mean ± standard deviation, (n = 3).

| Network | Irradiation time (min) | PI/TMC$^a$ (mol/mol) | Methacrylate/TMC$^a$ (mol/mol) | E (MPa) | $\sigma_{yield}$ (MPa) | $\epsilon_{yield}$ (%) | $\sigma_{break}$ (MPa) | $\epsilon_{break}$ (%) | Energy to break (Joule) | Permanent Set $^b$ (%) |
|---|---|---|---|---|---|---|---|---|---|---|
| PTMC$^c$ | non-irradiated | | 0 | 6.6 ± 0.5 | 2.1 ± 0.1 | 143 ± 5 | 4.6 ± 0.7 | 892 ± 47 | 2.2 ± 0.2 | 1.6 |
| PTMC-PI$^d$ | 120 | 1/1000 | 0 | 7.1 ± 0.1 | 2.2 ± 0.1$^e$ | 95 ± 7$^e$ | 16 ± 1 | 878 ± 7 | 4.0 ± 0.1 | 0.8 |
| PTMC-PI-DMAC$^d$ | 120 | 1/1000 | 1/50 | 7.1 ± 0.6 | 2.3 ± 0.1$^e$ | 90 ± 5$^e$ | 22 ± 2 | 749 ± 28 | 4.7 ± 0.6 | 1.0 |
| PTMC-PI-TMAC$^d$ | 120 | 1/1000 | 1/50 | 7.5 ± 0.2 | 2.3 ± 0.1$^e$ | 90 ± 8$^e$ | 24 ± 3 | 731 ± 28 | 5.2 ± 0.7 | 0.6 |

$^a$Based on TMC repeating units in the polymer
$^b$Single measurements. The permanent set is estimated from the 21$^{st}$ cycle, after a two hours recovery period. The error is approximately 0.5% strain.
$^c$Linear PTMC polymer, purified by precipitation and drying in vacuo, and compression molded
$^d$Networks were extracted with ethanol and dried in vacuo.
$^e$Estimated from the intersection of tangents to stress-strain diagrams, as a distinct yield point could not be observed.

Mechanical Properties of Photocross-Linked PTMC Networks

The tensile properties of compression moulded films prepared from linear PTMC and from photocross-linked and extracted PTMC network films are given in Table 7, while representative stress-strain curves are shown in FIG. 22. PTMC photocross-linking has lead to significantly higher stress at break values, while the strain at break values remained very high. Photocross-linking results in films with much higher toughness. PTMC networks prepared from high molecular weight PTMC films containing TMAC as cross-linking reagent had stress at break values as high as 24±3 MPa. Moreover, the flexible character of PTMC was not influenced much by the cross-linking. The E-modulus values of films prepared from linear PTMC was 6.6±0.5 MPa, whereas the values ranged from 7.1±0.1 to 7.5±0.2 for the photocross-linked PTMC films. This is most important, as these networks are intended to be used in medical applications involving soft tissues.

When culturing cells in tissue engineering scaffolds bioreactors are often used, as this allows to closely match the Human Mesenchymal Stem Cell Culturing To assess the compatibility of photocross-linked and extracted PTMC networks with cells, human mesenchymal stem cells (hMSCs) were cultured on PTMC-PI-TMAC (1/50 methacrylate/TMC repeating unit in the polymer) surfaces.

The hMSCs remained viable during culturing; FIG. 24 shows hMSCs on the surface of the films after four weeks. At this time point, a dense population of hMSCs having an elongated morphology was present on the network films. This initial assay showed that these photocross-linked PTMC networks are suitable materials for the preparation of tissue engineering scaffolds as hMSCs remain viable and in a healthy state on these surfaces for a long time. Differentiation of hMSCs on these PTMC based network films is a topic of further investigation.

In Vitro Erosion and Wettability of Photocross-Linked PTMC Networks

After implantation of a resorbable polymer, macrophages become the predominant cells at the tissue-biomaterial interface. Macrophages can engage in the events of the foreign body reaction as well as in the events of biomaterial degradation and erosion. Macrophage culturing has been used as an initial in vitro assay for biocompatibility and biodegradation of degradable polymers. With such an assay, it was shown that small crystalline particles of short chain poly(3-hydroxy butyric acid) can cause damage to macrophages in a dose dependent manner indicating the importance of degradation products and the rate of degradation on biocompatibility of biodegradable polymers. To assess the erosion behaviour of photocross-linked PTMC networks, we cultured macrophages on extracted network films and compared their erosion with that of linear PTMC films. All network films contained 1/1000 PI/TMC repeating unit, varying amounts of TMAC (methacrylate/TMC repeating unit 0, 1/200, 1/100, 1/50) and were photocross-linked by 120 min UV-irradiation.

After 14 days of macrophage culturing, all PTMC films were found to have eroded. Their mass had decreased and the formation of pits on the surface of the films was observed, indicating erosion of the surfaces during macrophage culture (FIG. 25). An overview of the erosion rates of the films in macrophage cultures is given in Table 8. It is worth noting that neither from the used PTMC based materials nor from their degradation products no cytotoxic effect on macrophages was observed during the culturing period. Moreover, neither the materials nor their degradation products induced activation of macrophages. This is an indication of biocompatibility of these materials and corroborates observations with mesenchymal stem cells.

sion rate of films having methacrylate to TMC ratios of 0, 1/200, 1/100, and 1/50 were respectively 28±4, 16±4, 12±1, 11±3 ($\mu g/cm^2 \times day$) (corresponding to mass losses ranging from 0.7 to 0.3%). In FIGS. 25C to 25J, the reduction in the extent of erosion of the films with increasing amounts of cross-linking reagent is very clear; the pits on the surface of the films had become much shallower.

The observed reduction in macrophage-mediated erosion of photocross-linked films could be due to (a denser) network formation that makes the bonds less accessible for (enzymatic) hydrolysis. The swelling ratios of these networks in chloroform ranged from 14.6±1.2 to 8.5±0.1 vol/vol. Another reason could be differences in adhesion and proliferation of macrophages on different surfaces. We determined the number of cells on different network films after 14 days of culturing. It appears from FIG. 26 that the network films containing TMAC as cross-linking reagent had lower number of macrophages (ranging from 2607±1033 to 4082±681) than that on noncross-linked PTMC films (5657±755 cell/mm$^2$) or PTMC-PI network films (6574±1433 cell/mm$^2$). However, the reduction in cell numbers on different surfaces was much less than the reduction in erosion of different films. Therefore, even after normalizing the erosion rates to cell numbers, a decrease in erosion rate of PTMC films upon cross-linking was obvious.

The adhesion of cells on biomaterials to large extent depends on protein adsorption which is dictated by surface

TABLE 8

Surface erosion rates of non-cross-linked and photocross-linked PTMC films in macrophage culture, or incubated in aqueous cholesterol esterase or potassium dioxide solution.

| Network | PI/TMC[a] (mol/mol) | MA/TMC[a] (mol/mol) | Erosion rate in MQ cultures ($\mu g/(cm^2 \times day)$) | Erosion rate in CE solutions ($\mu g/(cm^2 \times day)$) | Erosion rate in KO$_2$ solutions ($\mu g/(cm^2 \times day)$) |
|---|---|---|---|---|---|
| PTMC[b] | Non-irradiated | | 159 ± 8 | 2160 ± 610 | 2040 ± 360 |
| PTMC-PI | 1/1000 | 0 | 28 ± 4 | 137 ± 38 | 1280 ± 130 |
| PTMC-PI-TMAC[c] | 1/1000 | 1/200 | 16 ± 4 | 20 ± 5 | 670 ± 50 |
| PTMC-PI-TMAC[c] | 1/1000 | 1/100 | 12 ± 3 | 13 ± 4 | 670 ± 15 |
| PTMC-PI-TMAC[c] | 1/1000 | 1/50 | 11 ± 3 | 15 ± 3 | 740 ± 50 |

[a]Based on TMC repeating units in the polymer
[b]Linear PTMC polymer, purified by precipitation and drying in vacuo.
[c]Networks were extracted with ethanol and dried in vacuo.

Macrophages were most effective on films prepared from linear PTMC. The erosion rate of these films was 159±8 ($\mu g/(cm^2 \times day)$), which corresponds to a mass loss of 3.8±0.2%. SEM revealed that the surfaces had been extensively eroded (FIGS. 25A and 25B). Erosion of PTMC films could be reduced by photocross-linking, as erosion of the PTMC-PI network films was much less than that of the non-cross-linked PTMC films. This is of great importance, as linear or lightly cross-linked PTMC films erode relatively rapidly in vivo, hindering their use in long term biomedical applications. The erosion rate could be reduced further by using PTMC macromers as cross-linking reagents. The eroproperties of biomaterials. The water in air contact angles and the amount of water uptake for noncross-linked and photo-cross-linked PTMC films are given in Table 9. The values indicate that PTMC and its networks are hydrophobic. All films gained approximately 1% weight upon incubation in PBS for one week. Upon cross-linking and with increasing amounts of TMAC, the contact angles increased from 80° to 97°. The very high hydrophobicity of TMAC containing network films probably lead to adhesion of macrophages to a lesser degree on these surfaces compared to linear PTMC as cell adhesion is not promoted by very hydrophobic or very hydrophilic surfaces.

TABLE 9

Effect of photocross-linking and macromer content on water contact angles and water uptake values of PTMC films. Values are expressed as mean ± standard deviation.

| Network | PI/TMC (mol/mol) | MA/TMC (mol/mol) | Water uptake (%)[a] | Water contact angle (°)[b] | | |
|---|---|---|---|---|---|---|
| | | | | Static | Advancing | Receding |
| PTMC | 0 | 0 | 1.2 ± 0.3 | 80.1 ± 2.7 | 83.3 ± 1.4 | 48.6 ± 1.7 |
| PTMC-PI | 1/1000 | 0 | 0.9 ± 0.2 | 87.9 ± 2.0 | 89.7 ± 2.3 | 51.8 ± 1.3 |
| PTMC-PI-TMAC | 1/1000 | 1/200 | 1.3 ± 0.3 | 91.1 ± 0.7 | 93.1 ± 0.6 | 53.8 ± 0.4 |
| PTMC-PI-TMAC | 1/1000 | 1/100 | 0.9 ± 0.2 | 97.3 ± 1.6 | 99.9 ± 1.6 | 60.9 ± 0.7 |
| PTMC-PI-TMAC | 1/1000 | 1/50 | 0.8 ± 0.2 | 97.2 ± 2.1 | 99.4 ± 1.32 | 60.5 ± 1.2 |

[a]Compression moulded films were conditioned in PBS at 37° C. for one week (n = 4).
[b]Performed on polymer films cast on glass discs (n = 6).

Further, the erosion of the photocross-linked PTMC networks have been investigated according to the present invention using aqueous cholesterol esterase (CE) and aqueous $KO_2$ solutions. Table 8 shows erosion rates of non-cross-linked and photocross-linked PTMC films determined upon incubation in these solutions.

Upon incubation in aqueous cholesterol esterase solutions, non-cross-linked PTMC films eroded linearly in time. Surface erosion of non-cross-linked PTMC specimens proceeded at a rate of 2160±600 ($\mu g/cm^2 \times day$) leading to a mass loss of 87.9±1.6% mass loss in 14 days. In this case, photo-cross-linking had a more dramatic effect on enzymatic erosion of PTMC than that observed in the macrophage-mediated erosion. Upon 15 days of incubation in CE solutions, mass loss of the network films having 0 to 1/50 methacrylate to TMC ratios ranged from 6.6±1.8% to 0.6±0.2% (corresponding to rates from 137±38 to 15±3 ($\mu g/cm^2 \times day$)).

Upon incubation in superoxide anion radical containing buffers, the mass of non-cross-linked and cross-linked PTMC films decreased at a constant rate, implying their surface erosion in these media. The erosion rate of non-cross-linked PTMC was 2040±360 ($\mu g/cm^2 \times day$), which is comparable to that observed when these films were incubated in CE solutions (2160±610 ($\mu g/cm^2 \times day$)). Upon one week incubation in aqueous $KO_2$ solutions, the mass loss of non-cross-linked films was 48.7±8.5%. The degradation of PTMC by oxidative species was also reduced by photocross-linking in the presence of photoinitiator only. Upon one week incubation, the mass loss of PTMC-PI networks was 30.8±3.7, whereas PTMC-PI-TMAC networks had a mass loss of approximately 16±0.5%.

Conclusion

High molecular weight PTMC can be photocross-linked using low molecular weight PTMC macromers and Irgacure® 2959 photoinitiator as cross-linking reagents. The characteristics (network properties, mechanical properties, in vitro erosion behaviour, water contact angles and wettability) of the obtained networks can be tuned by adjusting the amounts of the cross-linking reagent incorporated. These surface eroding elastomeric PTMC networks have excellent mechanical properties. Moreover, initial in vitro assays showed that these materials and their degradation products are biocompatible. These materials are very most suited for biomedical applications such as (soft-) tissue engineering and controlled release of biologically active compounds.

The invention claimed is:

1. A method for preparing a degradable polymer network comprising:
    a) preparing a polymer composition by polymerization of monomers obtained from cyclic carbonates, cyclic esters, cyclic ethers, linear carbonates, linear esters, linear ethers, linear hydroxycarboxylic acids, or any combination thereof, at a temperature between 20° C. and 200° C., wherein the cyclic carbonates are selected from a group consisting of trimethylene carbonate, ethylene carbonate, diethylene glycol-bis-allyl-carbonate, and derivatives thereof;
    b) adding a cross-linking reagent comprising at least one double or triple C—C bond;
    c) processing the polymer composition into a desired shape;
    d) crosslinking by irradiating the mixture.

2. The method according to claim 1, wherein the crosslinking reagent is selected from a group consisting of an acrylate, a methacrylate, a multi-acrylate, a multi-methacrylate, fumarate, a multi-fumarate, a maleate, a multimaleate, a maleic anhydride, an itaconate, a multi-itaconate, and derivatives thereof.

3. The method according to claim 1, wherein the cross-linking reagent comprises: ethylene diacrylate, ethylene glycoldiacrylate, tetraethylene glycol diacrylate, polyethylene glycol diacrylate, trimethylolpropane triacrylate, pentaerythritol triacrylate, pentaerythritol tetra-acrylate, ethylene glycoldimethacrylate, tetraethylene glycol dimethacrylate, polyethylene glycol dimethacrylate, acrylate-functionalized poly(trimethylenecarbonate)-based oligomer, an methacrylatefunctionalized poly(trimethylenecarbonate)-based oligomer, a fumarate-functionalized poly(trimethylenecarbonate)-based oligomer, an acrylate-functionalized poly(D,L-lactide)-based oligomer, methacrylate-functionalized poly(D,L-lactide)based oligomer, a fumarate-functionalized poly(D,L-lactide)-based oligomer, an acrylate-functionalized poly(L-lactide)-based oligomer, a methacrylate-functionalized poly(L-lactide)-based oligomer, a fumarate-functionalized poly(L-lactide)-based oligomer, an acrylate-functionalized poly($\epsilon$-caprolactone)-based oligomer, a methacrylate functionalized poly(E-caprolactone)-based oligomer, a fumarate-functionalized poly($\epsilon$-caprolactone)-based oligomer, an acrylate-functionalized poly(ethylene glycol)-based oligomer, a methacrylate-functionalized poly(ethylene glycol)-based oligomer, a fumarate-functionalized poly(ethylene glycol)-based oligomer, or derivatives thereof.

4. The method according to claim 1, wherein the cross-linking reagent comprises 0.01% wt to 15% wt of the cross-linking reagent by weight percentage of the total weight of the polymer composition.

5. The method according to claim 1, wherein the monomers in step a) are obtained from cyclic esters selected from a group consisting of L-lactide, D-lactide, D,L-lactide, ε-caprolactone, dioxanone, glycolide, and derivatives thereof.

6. The method according to claim 1, wherein the monomers in step a) are obtained from linear carbonates selected from a group consisting of diethyl carbonate and diphenylcarbonate.

7. The method according to claim 1, wherein the monomers in step a) are obtained from linear esters selected from a group consisting of fumaric acid monoethyl ester, fumaric acid diethylester, and dimethylterephtalate, diethylterephtalate.

8. The method according to claim 1, wherein the monomers in step a) are obtained from linear ethers comprising polyethylene glycol.

9. The method according to claim 1, wherein the polymer composition in step a) comprises a cyclic or linear carbonate content in mol percentage of the total copolymer, of 40% mol to 85% mol.

10. The method according to claim 1, wherein step b) further comprises adding a cross-linking radical initiator.

11. The method according to claim 10, wherein step b) further comprises 0.001% wt to 0.1% wt of the crosslinking radical initiator by weight percentage of the total weight of the polymer composition.

12. The method according to claim 1, wherein step b) further comprises adding a solvent which is acetone, dichloromethane, chloroform, carbontetrachloride, ethylene carbonate, propylene carbonate, dimethylsulfoxide, toluene, benzene, tetrahydrofuran or 1,4-dioxane.

13. The method according to claim 1, wherein the irradiation in step d) is ultraviolet, visible, infrared, microwave, or gamma irradiation.

14. The method according to claim 13, wherein the gamma irradiation comprises a radiation of 10 to 150 kGy.

15. The method according to claim 1, wherein the desired shape of the polymer composition in step c) is obtained by compression molding, extrusion, injection molding or casting, each at a temperature from 20° C. to 200° C.

16. The method according to claim 1, wherein the desired shape in step c) are films which have a thickness of 1 μm to 1000 μm.

17. The method according to claim 1, wherein the preparation of the polymer composition comprises a ring-opening polymerization and/or a polycondensation.

18. The method according to claim 1, wherein the preparation of the polymer composition is carried out at a temperature between 100° C. and 160° C.

19. A degradable polymer network obtainable by the method according to claim 1.

20. The method according to claim 10, wherein the cross-linking radical initiator is selected from a group consisting of a photo-initiator, thermal initiator, and a redoxinitiator.

* * * * *